(12) United States Patent
Choi et al.

(10) Patent No.: US 8,809,060 B2
(45) Date of Patent: Aug. 19, 2014

(54) ETHANOL-RESISTANT YEAST GENE, AND USE THEREOF

(75) Inventors: Won Ja Choi, Seoul (KR); Wan Kee Kim, Suwon-si (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 16 days.

(21) Appl. No.: 13/643,015

(22) PCT Filed: Nov. 24, 2010

(86) PCT No.: PCT/KR2010/008340
§ 371 (c)(1),
(2), (4) Date: Jan. 4, 2013

(87) PCT Pub. No.: WO2011/132836
PCT Pub. Date: Oct. 27, 2011

(65) Prior Publication Data
US 2013/0137181 A1 May 30, 2013

(30) Foreign Application Priority Data

Apr. 23, 2010 (KR) .................. 10-2010-0037818
Oct. 19, 2010 (KR) .................. 10-2010-0101739
Oct. 19, 2010 (KR) .................. 10-2010-0101765
Nov. 24, 2010 (KR) .................. 10-2010-0117208

(51) Int. Cl.
*C12N 15/11* (2006.01)
*C12N 15/31* (2006.01)
*C12N 15/19* (2006.01)
*C07K 14/395* (2006.01)
*C12P 7/06* (2006.01)
*C12N 15/10* (2006.01)

(52) U.S. Cl.
CPC .............. *C07K 14/395* (2013.01); *C12P 7/06* (2013.01); *C12N 15/1034* (2013.01)
USPC ............... 435/471; 435/254.2; 435/254.21; 435/476; 435/477; 435/483

(58) Field of Classification Search
None
See application file for complete search history.

(56) References Cited

U.S. PATENT DOCUMENTS

2010/0291648 A1* 11/2010 Alper et al. .................. 435/161

FOREIGN PATENT DOCUMENTS

CN 101270156 A * 9/2008
WO WO 2008133665 A2 * 11/2008

OTHER PUBLICATIONS

Kou et al., Structural and functional analysis of mutations along the crystallographic dimer interface of the yeast TATA binding protein, Mol. Cell. Biol., 2003, 23, 3186-3201.*
Machine Translation of CN 101270156 A, Sep. 2008, www.epo.org/searching/asian/translation.html.*
Poon et al., Genetic and biochemical analyses of yeast TATA-binding protein mutants, J. Biol. Chem., 1993, 268, 5005-13.*
Cormack et al., Regional codon randomization: defining a TATA-binding protein surface required for RNA polymerase III transcription, Science, 1993, 262, 244-248.*
Lee et al., Multiple functions of the nonconserved N-terminal domain of yeast TATA-binding protein, Genetics, 2001, 158, 87-93.*
Cang et al., A new regulatory domain on the TATA-binding protein, EMBO J., 1999, 18, 6662-71.*
Alper et al., "Engineering Yeast Transcription Machinery for Improved Ethanol Tolerance and Production," Science 314:1565-1568, 2006.
International Search Report and Written Opinion from PCT/KR2010/00830, dated Oct. 25, 2011.

* cited by examiner

*Primary Examiner* — Rebecca Prouty
*Assistant Examiner* — Todd M Epstein
(74) *Attorney, Agent, or Firm* — Clark & Elbing LLP

(57) ABSTRACT

The present invention relates to a gene associated with ethanol tolerance, and yeast strains and uses using the same. The yeast strain of this invention may growth under the condition not only with high-concentration ethanol, preferably 6-15% ethanol, but also in high osmotic pressure, preferably 30-40% glucose or sucrose. The present inventors developed yeast strains resistant to high-concentration glucose and ethanol, suggesting that they would be valuably applied to much effective ethanol production, and also be utilized as a superbacteria having tolerance to various stresses for ethanol production with high efficiency.

10 Claims, 10 Drawing Sheets

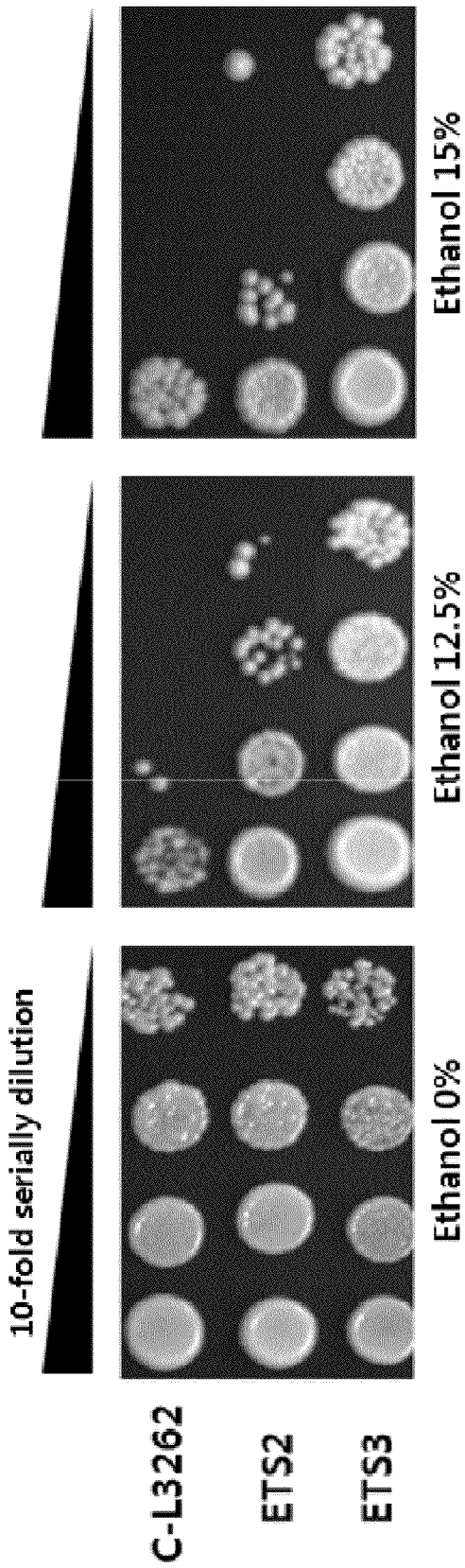

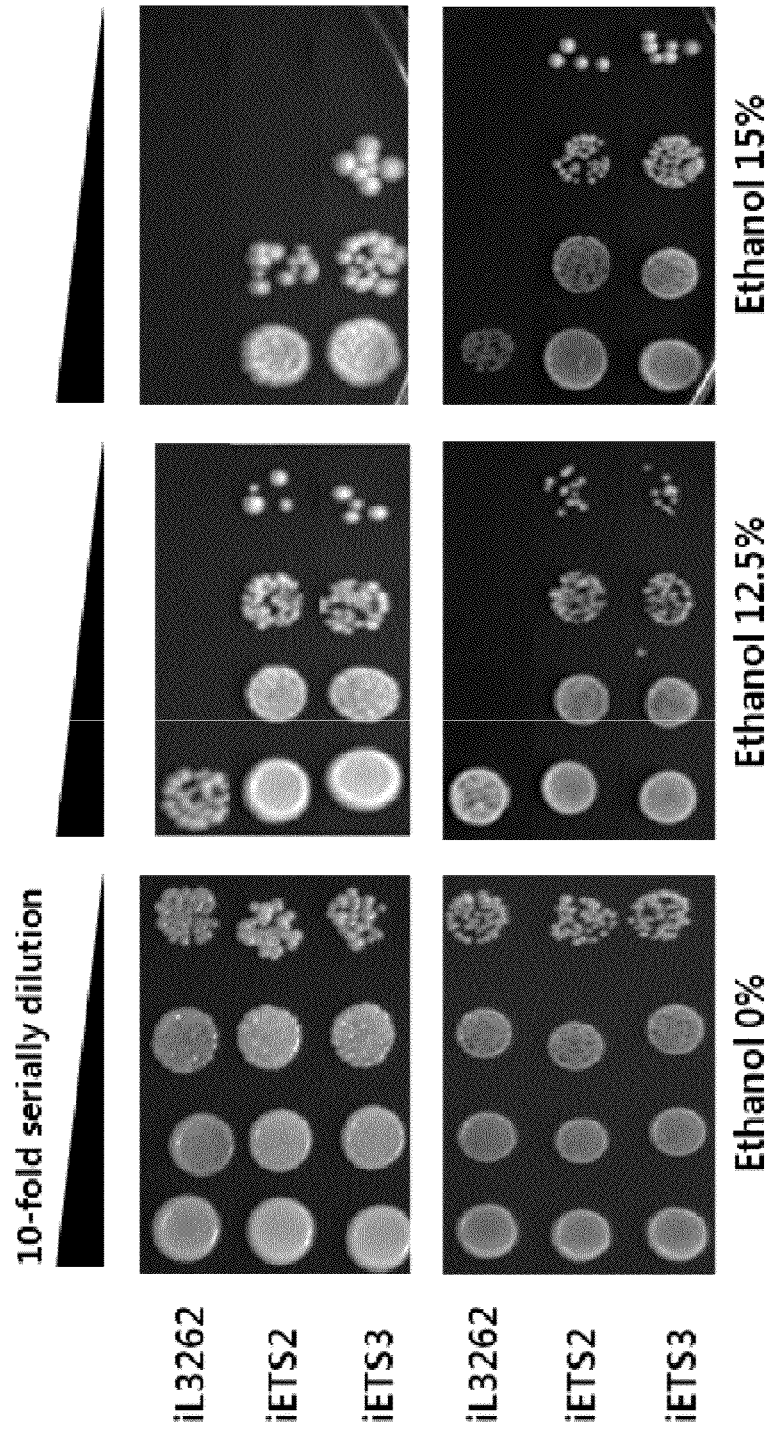

Fig. 5
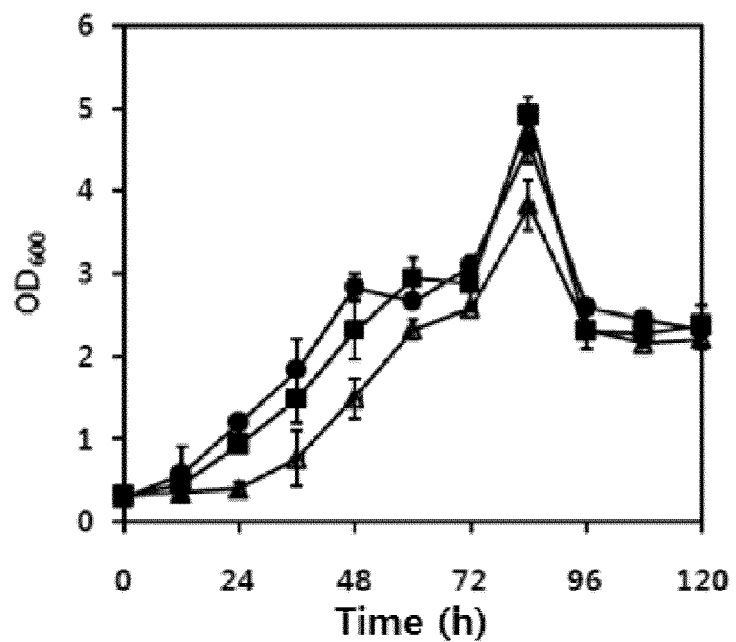
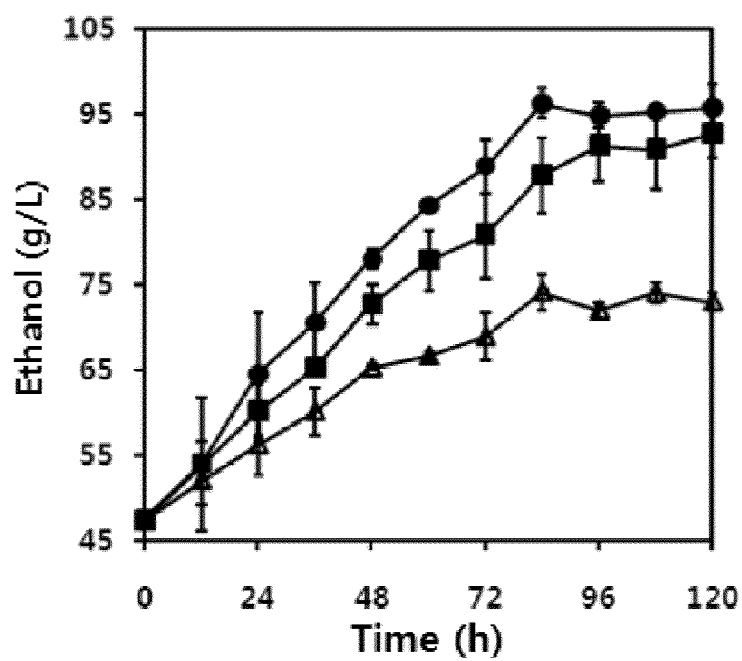

Fig. 6
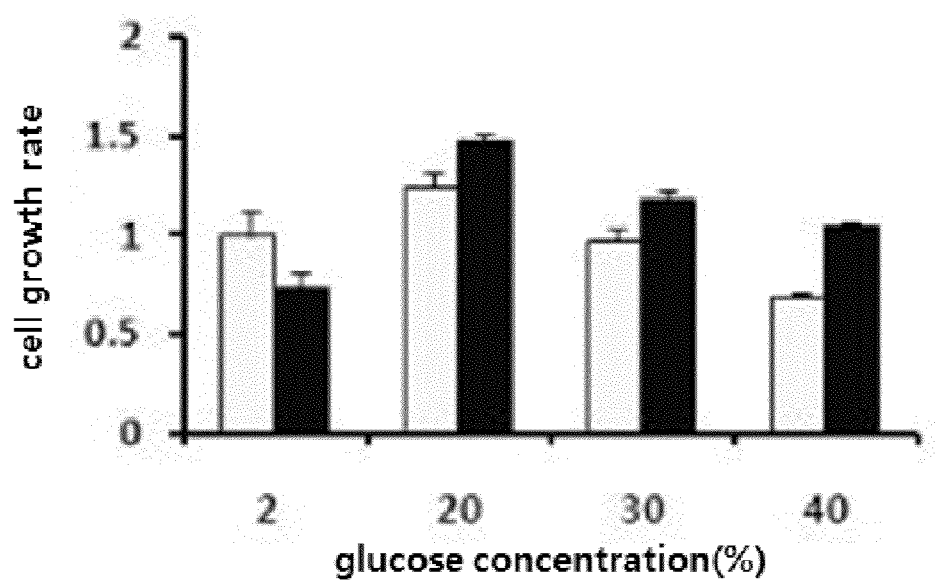
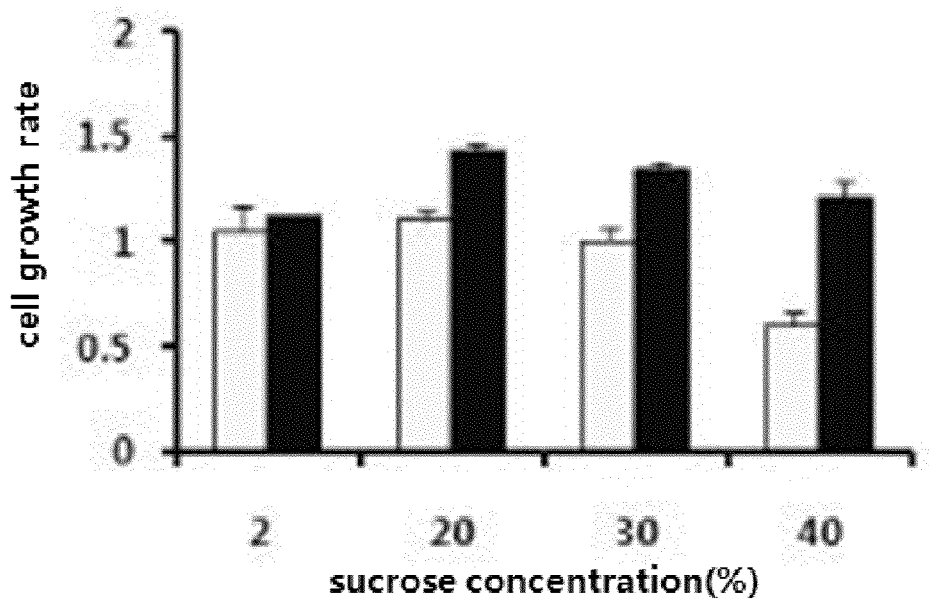

SEQUENCE LISTING

```
<160> NUMBER OF SEQ ID NOS: 46

<210> SEQ ID NO 1
<211> LENGTH: 672
<212> TYPE: DNA
<213> ORGANISM: Artificial Sequence
<220> FEATURE:
<223> OTHER INFORMATION: SPT15_M1

<400> SEQUENCE: 1
atggccgatg aggaacgttt aaaggagttt aaagaggcaa acaagatagt gtttgatcca      60
aataccagac aagtatggga aaaccagaat cgagatggta caaaaccagc aactactttc     120
cagagtgaag aggacataaa aagagctgcc ccagaatctg aaaaagacac ctccgccaca     180
tcaggtattg ttccaacact acaaaacatt gtggcaactg tgactttggg gtgcaggtta     240
gatctgaaaa cagttgcgct acatgcccgt aatgcagaat ataaccccaa gcgttttgct     300
gctgtcatca tgcgtattag agagccaaaa actacagctt taattttgtc ctcagggaaa     360
atggttgtta ccggtgcaaa aagtgaggat gactcaaagc tggccagtag aaaatatgca     420
agaattatcc aaaaaatcgg gtttgctgct aaattcacag acttcaaaat acaaaatatt     480
gtcggttcgt gtgacgttaa attccctata cgtctagaag ggttagcatt cagtcatggt     540
actttctcct cctatgagcc agaattgttt cctggtttga tctatagaat ggtgaagccg     600
```

```
caaattgtgt tgttaatttt tgtttcagga aagattgttc ttactagtgc aaagcaaagg    660
gaagaaattt ac                                                        672
```

<210> SEQ ID NO 2
<211> LENGTH: 720
<212> TYPE: DNA
<213> ORGANISM: Artificial Sequence
<220> FEATURE:
<223> OTHER INFORMATION: SPT15_M2

<400> SEQUENCE: 2

```
atggccgatg aggaacgttt aaaggagttt aaagaggcaa acaagatagt gtttgatcca     60
aataccagac aagtatggga aaaccagaat cgagatggta caaaaccagc aactactttc    120
cagagtgaag aggacataaa aagagctgcc ccagaatctg aaaagacac ctccgccaca    180 tcaggtattg ttccaacact acaaaacatt gtggcaactg taactgtggg gtgcaggtta    240
gatctgaaaa cagttgcgct acatgcccgt aatgcagaat ataaccccaa gcgttttgct    300
gctgtcatca tgcgtattag agagccaaaa actacagctt taattttttgc ctcagggaaa    360 atggttgtta ccggtgcaaa aagtgaggat gactcaaagc tggccagtag aaaatatgca    420
agaattatcc aaaaaatcgg gtttgctgct aaattcacag acttcaaaat acaaaatatt    480
gtcggttcgt gcgacgttaa attccctata cgtctagaag ggtcagcatt cagtcatggt    540
actttctcct cctatgagcc agaattgttt cctggtttga tctatagaat ggtgaagccg    600
aaaattgtgt tgttaatttt tgtttcagga aagattgttc ttactggtgc aaagcaaagg    660
gaagaaattt accaagcttt tgaagctata taccccgtgc taagtgaatt tagaaaaatg    720
```

<210> SEQ ID NO 3
<211> LENGTH: 720
<212> TYPE: DNA
<213> ORGANISM: Artificial Sequence
<220> FEATURE:
<223> OTHER INFORMATION: SPT15_M3

<400> SEQUENCE: 3

```
atggccgatg aggaacgttt aaaggagttt aaagaggcaa acaagatagt gtttgatcca     60
aataccagac aagtatggga aaaccagaat cgagatggta caaaaccagc aactactttc    120
cagaatgaag aggacataaa aagagctgcc ccagaatctg aaaagacac ctccgccaca    180 tcaggtattg ttccaacact acaaaacatt gtggcaactg tgactttggg gcgcaggtta    240
gatctgaaaa cagttgcgct acatgcccgt aatgcagaat ataaccccaa gcgttttgct    300
gctgtcatca tgcgtattag agagccaaaa actacagctt taattttttgc ctcagggaaa    360 atggttgtta ccggtgcaaa aagtgaggat gactcaaagc tggccagtag aaaatatgca    420
agaattatcc aaaaaatcgg gtttgctgct aaattcacag acttcaaaat acaaaatatt    480
gtcggtccgt gtgacgttaa attccctata cgtctagaag ggttagcatt cagtcatggt    540
actttctcct cctatgagcc agaattgttt cctggtttga tctatagaat ggtgaagccg    600
aaaattgtgt tgttaatttt tgtttcagga agaatgttc ttactggtgc aaagcaaagg    660
gaagaaattt accaagcttt tgaagctata taccctgtgc taagtgaatt tagaaaaatg    720
```

<210> SEQ ID NO 4
<211> LENGTH: 720
<212> TYPE: DNA
<213> ORGANISM: Artificial Sequence
<220> FEATURE:
<223> OTHER INFORMATION: SPT15_M4

<400> SEQUENCE: 4

```
atggccgatg aggaacgttt aaaggagtct aaagaggcaa acaagatagt gtttgatcca      60
aataccagac aagtatggga aaccagaat cgagatggta caaaaccagc aactactttc     120
cagagtgaag aggacataaa aagagctgcc ccagaatctg aaaagacac ctccgccaca     180
tcaggtattg ttccaacact acaaaacatt gtggcaactg tgactttggg gtgcaggtta     240
gatctgaaaa cagttgcgct acatgcccgt aatgcagaat ataaccccaa gcgttttgct     300
gctgtcatca tgcgtattag agagccaaaa actacagctt taattttgc ctcagggaaa     360
atggttgtta ccggtgcaaa aagtgaggat gactcaaagc tggccagtag aaaatatgca     420
agaattatcc aaaaaatcgg gtttgctgct aaattcacag acttcaaaat acaaaatatt     480
gtcggttcgt gtgacgttaa attccctata cgtctggaag ggttagcatt cagtcatggt     540
actttctcct cctatgagcc agaattgttt cctggtttga tctatagaaa ggtgaagccg     600
aaaattgtgt tgttaatttt tgtttcagga aagattgttc ttactggtgc aaagcaaagg     660
gaagaaattt accaagcttt tgaagctata taccctgtgc taagtgaatt tagaaaaatg     720
```

<210> SEQ ID NO 5
<211> LENGTH: 720
<212> TYPE: DNA
<213> ORGANISM: Artificial Sequence
<220> FEATURE:
<223> OTHER INFORMATION: SPT15_M5

<400> SEQUENCE: 5

```
atggccgatg aggaacgttt aaaggagttt aaagaggcaa acacgatagt gtttgatcca      60
aataccagac aagtatgtga aaccagaat cgagatggta caaaaccagc aactactttc     120
cagagtgaag aggacataaa aagagctgcc ccagaatctg aaaagacac ctccgccaca     180
tcaggtattg ttccaacact acaaaacatt gtggcaactg tgactttggg gtgcaggtta     240
gatctgaaaa cagttgcgct acatgcccgt aatgcagaat ataaccccaa gcgttttgct     300
gctgtcatca tgcgtattag agagccaaaa actacagctt taattttgc ctcagggaaa     360
atggttgtta ccggtgcaaa aagtgaggat gactcaaagc tggccagtag aaaatatgca     420
agaattatcc aaaaaatcgg gtttgctgct aaattcacag acttcaaaat acaaaatatt     480
gtcggttcgt gtgacgttaa attccctata cgtctagaag ggttagcatt cagtcatggt     540
actttctcct cctatgagcc agaattgttt cctgatttga tctatagaat ggtgaagccg     600
aaaattgtgt tgttaatttt tgtttcagga aagattgttc ttactggtgc aaagcaaagg     660
gaagaaattt accaagcttt tgaagctata taccctgtgc taagtgaatt tagaaaaatg     720
```

<210> SEQ ID NO 6
<211> LENGTH: 224
<212> TYPE: PRT
<213> ORGANISM: Artificial Sequence
<220> FEATURE:
<223> OTHER INFORMATION: SPT15_M1

<400> SEQUENCE: 6

Met Ala Asp Glu Glu Arg Leu Lys Glu Phe Lys Glu Ala Asn Lys Ile
1               5                   10                  15

Val Phe Asp Pro Asn Thr Arg Gln Val Trp Glu Asn Gln Asn Arg Asp
            20                  25                  30

Gly Thr Lys Pro Ala Thr Thr Phe Gln Ser Glu Glu Asp Ile Lys Arg
        35                  40                  45

```
Ala Ala Pro Glu Ser Glu Lys Asp Thr Ser Ala Thr Ser Gly Ile Val
     50                  55                  60

Pro Thr Leu Gln Asn Ile Val Ala Thr Val Thr Leu Gly Cys Arg Leu
 65                  70                  75                  80

Asp Leu Lys Thr Val Ala Leu His Ala Arg Asn Ala Glu Tyr Asn Pro
                 85                  90                  95

Lys Arg Phe Ala Ala Val Ile Met Arg Ile Arg Glu Pro Lys Thr Thr
             100                 105                 110

Ala Leu Ile Phe Ala Ser Gly Lys Met Val Val Thr Gly Ala Lys Ser
         115                 120                 125

Glu Asp Asp Ser Lys Leu Ala Ser Arg Lys Tyr Ala Arg Ile Ile Gln
     130                 135                 140

Lys Ile Gly Phe Ala Ala Lys Phe Thr Asp Phe Lys Ile Gln Asn Ile
145                 150                 155                 160

Val Gly Ser Cys Asp Val Lys Phe Pro Ile Arg Leu Glu Gly Leu Ala
                 165                 170                 175

Phe Ser His Gly Thr Phe Ser Ser Tyr Glu Pro Glu Leu Phe Pro Gly
             180                 185                 190

Leu Ile Tyr Arg Met Val Lys Pro Gln Ile Val Leu Leu Ile Phe Val
         195                 200                 205

Ser Gly Lys Ile Val Leu Thr Ser Ala Lys Gln Arg Glu Glu Ile Tyr
     210                 215                 220
```

<210> SEQ ID NO 7
<211> LENGTH: 240
<212> TYPE: PRT
<213> ORGANISM: Artificial Sequence
<220> FEATURE:
<223> OTHER INFORMATION: SPT15_M2

<400> SEQUENCE: 7

```
Met Ala Asp Glu Glu Arg Leu Lys Glu Phe Lys Glu Ala Asn Lys Ile
 1               5                  10                  15

Val Phe Asp Pro Asn Thr Arg Gln Val Trp Glu Asn Gln Asn Arg Asp
             20                  25                  30

Gly Thr Lys Pro Ala Thr Thr Phe Gln Ser Glu Glu Asp Ile Lys Arg
         35                  40                  45

Ala Ala Pro Glu Ser Glu Lys Asp Thr Ser Ala Thr Ser Gly Ile Val
     50                  55                  60

Pro Thr Leu Gln Asn Ile Val Ala Thr Val Thr Val Gly Cys Arg Leu
 65                  70                  75                  80

Asp Leu Lys Thr Val Ala Leu His Ala Arg Asn Ala Glu Tyr Asn Pro
                 85                  90                  95

Lys Arg Phe Ala Ala Val Ile Met Arg Ile Arg Glu Pro Lys Thr Thr
             100                 105                 110

Ala Leu Ile Phe Ala Ser Gly Lys Met Val Val Thr Gly Ala Lys Ser
         115                 120                 125

Glu Asp Asp Ser Lys Leu Ala Ser Arg Lys Tyr Ala Arg Ile Ile Gln
     130                 135                 140

Lys Ile Gly Phe Ala Ala Lys Phe Thr Asp Phe Lys Ile Gln Asn Ile
145                 150                 155                 160

Val Gly Ser Cys Asp Val Lys Phe Pro Ile Arg Leu Glu Gly Ser Ala
                 165                 170                 175

Phe Ser His Gly Thr Phe Ser Ser Tyr Glu Pro Glu Leu Phe Pro Gly
             180                 185                 190
```

Leu Ile Tyr Arg Met Val Lys Pro Lys Ile Val Leu Leu Ile Phe Val
            195                 200                 205

Ser Gly Lys Ile Val Leu Thr Gly Ala Lys Gln Arg Glu Glu Ile Tyr
    210                 215                 220

Gln Ala Phe Glu Ala Ile Tyr Pro Val Leu Ser Glu Phe Arg Lys Met
225                 230                 235                 240

<210> SEQ ID NO 8
<211> LENGTH: 240
<212> TYPE: PRT
<213> ORGANISM: Artificial Sequence
<220> FEATURE:
<223> OTHER INFORMATION: SPT15_M3

<400> SEQUENCE: 8

Met Ala Asp Glu Glu Arg Leu Lys Glu Phe Lys Glu Ala Asn Lys Ile
1               5                   10                  15

Val Phe Asp Pro Asn Thr Arg Gln Val Trp Glu Asn Gln Asn Arg Asp
            20                  25                  30

Gly Thr Lys Pro Ala Thr Thr Phe Gln Asn Glu Glu Asp Ile Lys Arg
        35                  40                  45

Ala Ala Pro Glu Ser Glu Lys Asp Thr Ser Ala Thr Ser Gly Ile Val
    50                  55                  60

Pro Thr Leu Gln Asn Ile Val Ala Thr Val Thr Leu Gly Arg Arg Leu
65                  70                  75                  80

Asp Leu Lys Thr Val Ala Leu His Ala Arg Asn Ala Glu Tyr Asn Pro
                85                  90                  95

Lys Arg Phe Ala Ala Val Ile Met Arg Ile Arg Glu Pro Lys Thr Thr
            100                 105                 110

Ala Leu Ile Phe Ala Ser Gly Lys Met Val Val Thr Gly Ala Lys Ser
        115                 120                 125

Glu Asp Asp Ser Lys Leu Ala Ser Arg Lys Tyr Ala Arg Ile Ile Gln
    130                 135                 140

Lys Ile Gly Phe Ala Ala Lys Phe Thr Asp Phe Lys Ile Gln Asn Ile
145                 150                 155                 160

Val Gly Pro Cys Asp Val Lys Phe Pro Ile Arg Leu Glu Gly Leu Ala
                165                 170                 175

Phe Ser His Gly Thr Phe Ser Ser Tyr Glu Pro Glu Leu Phe Pro Gly
            180                 185                 190

Leu Ile Tyr Arg Met Val Lys Pro Lys Ile Val Leu Leu Ile Phe Val
            195                 200                 205

Ser Gly Lys Asn Val Leu Thr Gly Ala Lys Gln Arg Glu Glu Ile Tyr
    210                 215                 220

Gln Ala Phe Glu Ala Ile Tyr Pro Val Leu Ser Glu Phe Arg Lys Met
225                 230                 235                 240

<210> SEQ ID NO 9
<211> LENGTH: 240
<212> TYPE: PRT
<213> ORGANISM: Artificial Sequence
<220> FEATURE:
<223> OTHER INFORMATION: SPT15_M4

<400> SEQUENCE: 9

Met Ala Asp Glu Glu Arg Leu Lys Glu Ser Lys Glu Ala Asn Lys Ile
1               5                   10                  15

Val Phe Asp Pro Asn Thr Arg Gln Val Trp Glu Asn Gln Asn Arg Asp

```
                    20                  25                  30

Gly Thr Lys Pro Ala Thr Thr Phe Gln Ser Glu Glu Asp Ile Lys Arg
            35                  40                  45

Ala Ala Pro Glu Ser Glu Lys Asp Thr Ser Ala Thr Ser Gly Ile Val
 50                  55                  60

Pro Thr Leu Gln Asn Ile Val Ala Thr Val Thr Leu Gly Cys Arg Leu
 65                  70                  75                  80

Asp Leu Lys Thr Val Ala Leu His Ala Arg Asn Ala Glu Tyr Asn Pro
                85                  90                  95

Lys Arg Phe Ala Ala Val Ile Met Arg Ile Arg Glu Pro Lys Thr Thr
            100                 105                 110

Ala Leu Ile Phe Ala Ser Gly Lys Met Val Val Thr Gly Ala Lys Ser
            115                 120                 125

Glu Asp Asp Ser Lys Leu Ala Ser Arg Lys Tyr Ala Arg Ile Ile Gln
            130                 135                 140

Lys Ile Gly Phe Ala Ala Lys Phe Thr Asp Phe Lys Ile Gln Asn Ile
145                 150                 155                 160

Val Gly Ser Cys Asp Val Lys Phe Pro Ile Arg Leu Glu Gly Leu Ala
                165                 170                 175

Phe Ser His Gly Thr Phe Ser Ser Tyr Glu Pro Glu Leu Phe Pro Gly
            180                 185                 190

Leu Ile Tyr Arg Lys Val Lys Pro Lys Ile Val Leu Leu Ile Phe Val
            195                 200                 205

Ser Gly Lys Ile Val Leu Thr Gly Ala Lys Gln Arg Glu Glu Ile Tyr
            210                 215                 220

Gln Ala Phe Glu Ala Ile Tyr Pro Val Leu Ser Glu Phe Arg Lys Met
225                 230                 235                 240

<210> SEQ ID NO 10
<211> LENGTH: 240
<212> TYPE: PRT
<213> ORGANISM: Artificial Sequence
<220> FEATURE:
<223> OTHER INFORMATION: SPT15_M5

<400> SEQUENCE: 10

Met Ala Asp Glu Glu Arg Leu Lys Glu Phe Lys Glu Ala Asn Thr Ile
 1               5                  10                  15

Val Phe Asp Pro Asn Thr Arg Gln Val Cys Glu Asn Gln Asn Arg Asp
            20                  25                  30

Gly Thr Lys Pro Ala Thr Thr Phe Gln Ser Glu Glu Asp Ile Lys Arg
            35                  40                  45

Ala Ala Pro Glu Ser Glu Lys Asp Thr Ser Ala Thr Ser Gly Ile Val
 50                  55                  60

Pro Thr Leu Gln Asn Ile Val Ala Thr Val Thr Leu Gly Cys Arg Leu
 65                  70                  75                  80

Asp Leu Lys Thr Val Ala Leu His Ala Arg Asn Ala Glu Tyr Asn Pro
                85                  90                  95

Lys Arg Phe Ala Ala Val Ile Met Arg Ile Arg Glu Pro Lys Thr Thr
            100                 105                 110

Ala Leu Ile Phe Ala Ser Gly Lys Met Val Val Thr Gly Ala Lys Ser
            115                 120                 125

Glu Asp Asp Ser Lys Leu Ala Ser Arg Lys Tyr Ala Arg Ile Ile Gln
            130                 135                 140

Lys Ile Gly Phe Ala Ala Lys Phe Thr Asp Phe Lys Ile Gln Asn Ile
```

```
              145                 150                 155                 160
Val Gly Ser Cys Asp Val Lys Phe Pro Ile Arg Leu Glu Gly Leu Ala
            165                 170                 175

Phe Ser His Gly Thr Phe Ser Ser Tyr Glu Pro Glu Leu Phe Pro Asp
        180                 185                 190

Leu Ile Tyr Arg Met Val Lys Pro Lys Ile Val Leu Leu Ile Phe Val
    195                 200                 205

Ser Gly Lys Ile Val Leu Thr Gly Ala Lys Gln Arg Glu Glu Ile Tyr
210                 215                 220

Gln Ala Phe Glu Ala Ile Tyr Pro Val Leu Ser Glu Phe Arg Lys Met
225                 230                 235                 240

<210> SEQ ID NO 11
<211> LENGTH: 1518
<212> TYPE: DNA
<213> ORGANISM: Saccharomyces cerevisiae

<400> SEQUENCE: 11
atgcctacct tgtatactga tatcgaaatc ccacaattga aaatctcttt aaagcaaccg      60
ctagggttgt ttatcaacaa tgagttttgt ccatcatcag atggaaagac catcgaaact     120
gtgaacccag ctactggcga accgataaca tccttccaag cagctaacga aaaggatgta     180
gacaaagctg tgaaagctgc cagggctgct tttgataacg tttggtcgaa gacatcttct     240
gagcaacgtg gtatttatct ttcaaactta ttaaaactta ttgaggagga gcaagacaca     300
cttgccgcat tagagacttt agacgctggt aagcctttcc attccaatgc taaacaagac     360
ttagcccaga ttatagaact tacaagatac tatgcggggg cggtcgacaa gttcaatatg     420
ggtgaaacca ttccattgac ttttaacaag tttgcatata ctctaaaagt tcctttggc      480 gttgttgctc aaatcgttcc atggaattat cctctagcta tggcttgtag aaaaatgcaa     540
ggtgccttag cggccggtaa cacggttatc atcaaacctg ctgaaaatac ctctctatct     600
ctactttatt ttgctacttt aattaaaaaa gcaggttttc cacctggtgt tgtcaatgtc     660
attcctggtt atggttccgt tgtggggaaa gctttaggaa cccacatgga tatcgacaaa     720
atatctttta cgggaagtac taaggttggc ggctcagtat tggaagcttc cggccaatcg     780
aaccttaagg atatcacact agaatgcggt ggtaagtctc ctgctcttgt atttgaagat     840
gcagaccttg ataggctat agaatgggta gcaaatggta ttttttttaa ttcgggacag     900
atctgcactg caaactcaag agtttatgtt caaagttcga tctacgacaa gtttgttgaa     960
aagtttaaag aaactgcaaa gaaggagtgg gatgttgcag gaaaatttga tccgtttgat    1020
gagaaatgca tcgttggtcc agtatatca agtacacagt atgaccgcat caaaagttac    1080
atagaacgtg gtaaaaagga ggaaaagttg gacatgttcc agacctctga atttcctatt    1140
ggtggagcta aaggctactt cattccccca accatcttca ctgatgtacc agaaacatct    1200
aagttgctgc gtgatgaaat atttggcccg gttgtggttg ttagcaagtt cacaaattat    1260
gatgacgctc tgaagctggc taatgatact tgctacgggc tcgcctctgc ggtcttcacc    1320
aaagatgtca agaaagcgca catgtttgct cgcgatatta agcaggaac tgtttggatc    1380 aatcaaacca atcaagaaga agctaaagtt ccttttggcg gatttaagat gagtggtatt    1440
ggtagagaat caggcgacac cggcgttgat aactatttac aaataaaatc agtccatgtg    1500
gatctttcat tggataaa                                                   1518

<210> SEQ ID NO 12
```

<211> LENGTH: 1173
<212> TYPE: DNA
<213> ORGANISM: Saccharomyces cerevisiae

<400> SEQUENCE: 12

| | | | | | |
|---|---|---|---|---|---|
| atggaaaata | ccacgaatcg | taatactgca | ggcgttctta | cgagcagcaa | tggtaacttt | 60 |
| gccaccaata | gtgtagcggc | atcaactccg | aagaggtcca | aaagtgctcg | aaggaaaacg | 120 |
| ttcaaatgca | ccggatatga | cggttgtacg | atgtccttca | ctagagcgga | acatcttgca | 180 |
| cgtcatataa | gaaagcacac | tggtgaaaag | ccgttccagt | gtcctgcatg | tttgaaattc | 240 |
| ttcagtagag | ttgataattt | gaaacagcat | cgggaatcgg | tccatgcaca | taaaaaccac | 300 |
| cattctacca | gctcgcacca | gcgtaagcct | tcctcttcat | ctttatcctc | ctcttcttct | 360 |
| gcatcttctt | cgtcttctgc | ttcatcatct | acatcatata | gtgatcctta | caggaaaact | 420 |
| aatattaata | gcgggaacat | gccgatgatg | gcagaaaacg | aaaaagcgcc | ccaaataata | 480 |
| cattcttcgc | cggagttcat | tactagcacg | agaagcatcc | cacccatctc | tccaaggtcc | 540 |
| atttataata | cccaacgaca | gcaacaacac | caacaacaac | agcatcaaca | ggctccctat | 600 |
| tattttcctt | cccatccaat | cactgatagt | tactaccagt | atcctcttcc | cagtaataat | 660 |
| aacaccatca | attatttacc | atcagtagat | gtgcagtatc | ctttgaatgt | gagcccctcc | 720 |
| tcaacgagcc | atccggcctc | tgaggtaatc | atatcgtcct | ttcctccgag | gtccatgcca | 780 |
| agtacttcct | tcaaatataa | agattctgcc | gactttcaag | cacggacaac | tatgaacaaa | 840 |
| tacaatatta | gaccaagcaa | tatcaatgtc | aatactagta | atatcaataa | ccatcttgat | 900 |
| tcattctccc | cgccgttttc | tccgtcaacg | acagttgctg | aagcaaaacc | aattatttta | 960 |
| ccacagtatc | agcaggcatt | tagccaacca | ccaaatggaa | ataaaaacaa | taatatgtct | 1020 |
| tcctcgaaga | atggcggcaa | aggggagaa | aatttcaaga | atactgatga | tcgcaatgat | 1080 |
| aataataaca | aaaagaggtc | ggaaacttta | tcagagtctg | atatttcggt | caacaccaat | 1140 |
| aagaaaaggc | ttagtgttga | ttacatattg | act | | | 1173 |

<210> SEQ ID NO 13
<211> LENGTH: 279
<212> TYPE: DNA
<213> ORGANISM: Saccharomyces cerevisiae

<400> SEQUENCE: 13

| | | | | | |
|---|---|---|---|---|---|
| atgttgagaa | ccactttttt | gcgcactcca | agacaattga | tgcgtaaatc | gccaagggcg | 60 |
| tctttctcaa | tcgtcactag | ggccgccttt | cctcacctaa | agaacaatca | agatgaagct | 120 |
| gagaaaaaag | aacagggttt | gtttgatagc | aacaagaaga | ggttggacac | tttggaacac | 180 |
| ggcaagaatc | cagattataa | gcaacctgga | atggaagatt | tgaaaaaaaa | gggagatgac | 240 |
| gctagaatcg | aacaaaacag | gccagatgac | ggtgtttat | | | 279 |

<210> SEQ ID NO 14
<211> LENGTH: 483
<212> TYPE: DNA
<213> ORGANISM: Saccharomyces cerevisiae

<400> SEQUENCE: 14

| | | | | | |
|---|---|---|---|---|---|
| atgacaaaga | aggataagaa | ggaagtaaaa | gttcaaacgg | ttaccacgga | ggatggtgaa | 60 |
| accgtgaaag | tttttgaaga | cctgcagggt | tttgaaactt | tcattgccaa | tgaaactgaa | 120 |
| gatgatgatt | tcgatcattt | gcactgtaaa | ttaaattact | acccaccatt | tgtgctacac | 180 |
| gagtcgcacg | aggaccctga | aaaaattagt | gatgctgcaa | attctcattc | taagaagttc | 240 |

```
gtgcgtcacc tgcaccagca tattgaaaag catcttttga aagatattaa gcaagccgtt   300
aggaaacctg agcttaaatt tcacgaaaaa tcgaaggaag agacatttga taaaatcacc   360
tggcattacg gtgaggaaac tgaataccat ggtagacctt tcaagataga cgttcaagta   420
gtttgcacac atgaagatgc tatggtattt gtcgattaca aaacacatcc tgtaggcgca   480
aat                                                                 483
```

<210> SEQ ID NO 15
<211> LENGTH: 1230
<212> TYPE: DNA
<213> ORGANISM: Saccharomyces cerevisiae

<400> SEQUENCE: 15

```
atgtttttcca tattcaattc accatgtgtt tttgaacagc tgccatcttt tagtcagccc    60
ctacattcgc gttattttga ttgcagttct ccagtgagct attatccaga atgtaaaagg   120
aggaaagcaa taaagctaa cctaagagct ccaaaaaaaa gcgatgcaaa ttgttcagaa    180
cctttgaggt atgcacttgc tgaaacacca atggttata cattaagctt gtctaagcgg    240
attccatatg aactttttc aaagtacgtt aatgagaaat taggtgagct aaaggagaac    300
cattacagac caacttacca tgttgtccaa gatttttttg gaaaccagta ttatgttgaa   360
gatgaagcgg atgaagatgc tctattgaga tctgcattga aagatctgga ttttagagcc   420
ataggaaaga aaattgctaa ggatcttttc caagactacg aaatagaatt gaatcataga   480
ggtgatgaat tgagcatatt gagtaagaag gataaaatct ttaaggaatt ctctctagac   540
caagtgtttg aagatgtttt tgttattggc tgtggagttg aaaacataga tgatggctcg   600
agagaaaaat atgcactttt aaagattggt ttagttaagc atgaggaaga aatttccgaa   660
ggtggcatca acgaaccaaa gatgccaata attgaatcca aaatagacga gtctcacgat   720
gatgttaaca tgtctgaatc tttgaaggag gaagaagcgg agaaagcgaa agaaccacta   780
accaaagaag accaaataaa aaaatggata gaggaagaaa gattgatgca ggaggaaagc   840
agaaaatcag aacaggaaaa agctgccaag gaagatgaag aaaggcaaaa gaaagagaag   900
gaagccagat tgaaggcaag gaaagaatct ttgataaata gcaaaaaaac caagaggtcc   960
cagcaaaaaa aattgcaaaa ttccaaatca ttgcctatct ctgagattga ggccagcaat  1020
aaaaataata atagcaattc tggttcagca gaaagtgata atgaaagtat aaacagtgat  1080
tctgatacga ctttggattt ctctgtgtct ggtaatacac taaaaaaca cgcttcacccc  1140 ctattagaag acgttgagga tgaggaagtt gacagataca acgagtccct aagcagatct  1200
cccaagggaa actctattat tgaggagata                                   1230
```

<210> SEQ ID NO 16
<211> LENGTH: 333
<212> TYPE: DNA
<213> ORGANISM: Saccharomyces cerevisiae

<400> SEQUENCE: 16

```
atgtctactg taaccaaata cttttacaag ggtgaaaata cagatttgat tgtcttcgct    60
gcatccgaag agcttgtaga cgaatatttg aaaaatccat caattggtaa gctatctgaa   120
gttgtcgaac tcttcgaagt tttcactcct caggacggta ggggtgccga gggtgagttg   180
ggcgctgcct ccaaggccca agtggaaaat gagttcggta agggcaagaa gatcgaagaa   240
gttatcgatt tgatattgag aaatggtaag ccaaactcta ccacctctag tctcaaaacc   300
```

```
aaaggggta acgccggaac caaagcctac aat                                 333
```

<210> SEQ ID NO 17
<211> LENGTH: 996
<212> TYPE: DNA
<213> ORGANISM: Saccharomyces cerevisiae

<400> SEQUENCE: 17

```
atgaacgata cgctatcaag cttttaaat cgtaacgagg ctttagggct taatccacca    60
catggcctgg atatgcacat taccaagaga ggttcggatt ggttatgggc agtgtttgca  120
gtctttggct ttatattgct atgctatgtt gtgatgttct tcattgcgga gaacaagggc  180
tccagattga ctagatatgc cttagctcct gcatttttga tcactttctt tgaatttttt  240
gctttcttca cttatgcttc tgatttaggt tggactggtg ttcaagctga atttaaccac  300
gtcaaggtta gcaagtctat cacaggtgaa gttcccggta ttagacaaat cttttactcg  360
aaatatattg cctggttctt gtcctggcca tgccttttat ttttaatcga gttagccgct  420
agtactactg gtgagaatga cgacatttcc gccttggata tggtacattc gctgttaatt  480
caaatcgtgg gtaccttatt ctgggttgtt tcgctattag ttggttcatt gatcaagtcc  540
acctacaagt ggggttatta caccattggt gctgtcgcta tgttggttac ccaaggtgtg  600
atatgccaac gtcaattctt caatttgaaa actagagggt tcaatgcact tatgctgtgt  660
acctgcatgg taatcgtttg gttgtacttt atctgttggg gtctaagtga tggtggtaac  720
cgtattcaac cagacggtga ggctatcttt tatggtgttt tggatttatg tgtatttgcc  780
atttatccat gttacttgct aattgcagtc agccgtgatg gcaaattgcc aaggctatct  840
ttgacaggag gattctctca tcaccatgct acggacgatg tggaagatgc ggctcctgaa  900
acaaaagaag ctgttccaga gagcccaaga gcatctggag agactgcaat ccacgaaccc  960
gaacctgaag cagagcaagc tgtcgaagat actgct                            996
```

<210> SEQ ID NO 18
<211> LENGTH: 1686
<212> TYPE: DNA
<213> ORGANISM: Saccharomyces cerevisiae

<400> SEQUENCE: 18

```
atgaacgtgt tcggtaaaaa agaagaaaag caagaaaaag tttactctct acaaaacggt    60
tttccgtact ctcatcaccc atacgcttct caatactcaa gaccagacgg ccctatctta   120
ctgcaagact tccatctgct ggaaaatatt gcaagtttcg atagagaaag agttccggag   180
cgtgtagtcc atgccaaagg tggtggttgt agactggagt tcgaactaac agattctttg   240
agtgatatta catacgccgc tccataccag aatgtggggtt acaaatgtcc tggtcttgtt   300
cgttttttcca ccgttggtgg tgaaagtggt acaccagaca ctgcaagaga cccaagaggt   360
gtttcttttta aattctatac cgagtggggg aaccatgact gggtcttcaa caatactccc   420
gtcttcttcc tcagagacgc tattaagttt cccgtatttta tcattcgca aaagagagac   480
cctcagtctc atctgaatca gtttcaggac actaccatat actgggatta tctaacattg   540
aatccggaat caatccatca ataacttacc atgtttggtg atagaggtac tcctgcttcg   600
tgggctagta tgaacgcgta ctctggtcat tccttcatca tggtcaacaa agaaggtaag   660
gacacatatg tgcaattcca cgtcttgtcg gatactggtt tgaaaccctt gactggagat   720
aaggctgcta actgtcaggg ctcccacccct gattataatc aggcaaagct gttcactcaa   780
ttgcaaaatg gcgaaaagcc aaaatttaac tgttatgtgc aaacaatgac acccgaacaa   840
```

-continued

```
gcaactaagt tcaggtattc ggtaaatgac ctaacgaaaa tatggccaca caaggaattc    900
cctttgagaa aatttggtac catcacccta acggagaatg ttgacaatta tttccaagaa    960

attgaacaag ttgcattcag tccaacgaac acttgtatcc caggtattaa gccttctaat   1020
gattccgttc tacaagccag acttttctcc tatccagaca ctcaacgtca tagattggga   1080
gccaactatc agcaattgcc cgtcaacaga ccaagaaact tgggatgtcc atactccaaa   1140
ggtgattccc aatacactgc cgaacagtgt ccatttaaag cagtgaactt ccaaagggac   1200
ggcccaatga gttactacaa tttcggtcct gagccaaatt atatttccag tttaccaaat   1260
caaactctga aattcaaaaa tgaagacaac gacgaagtat ctgataagtt caaagggata   1320
gttcttgacg aagtaacaga agtttctgtg agaaaacagg aacaagacca aatcagaaac   1380
gagcatattg ttgatgccaa aattaatcaa tattactacg tttatggtat tagtccacta   1440
gacttcgaac agccaagagc tctatatgaa aaggtataca acgatgaaca gaagaaatta   1500
ttcgttcata acgttgtttg ccacgcttgt aagatcaaag atcctaaagt caaaaagaga   1560
gttacgcaat actttggttt gctaaacgaa gatttgggta aagtcattgc agaatgcttg   1620
ggagttcctt gggaacctgt tgaccttgaa ggttatgcca agacttggtc cattgcaagt   1680
gccaat                                                              1686
```

<210> SEQ ID NO 19
<211> LENGTH: 1395
<212> TYPE: DNA
<213> ORGANISM: Saccharomyces cerevisiae

<400> SEQUENCE: 19

```
atgctaagat caaatttatg cagaggatct cgaatccttg caagactgac cactacacca     60
aggacataca catctgcggc gacagctgcg gctgcgaatc ggggacatat catcaaaaca    120
tacttcaata gagattctac gacaattacg ttctccatgg aggagtccag caagccggtt    180
tccgtttgct ttaacaacgt ttttcttaga gatgcctccc atagtgccaa gctggtgacc    240
acgggagaac tgtatcataa cgagaaattg accgctcctc aggacattca aatttctgag    300
gacggaaaat ctctagtggt gaaatggaaa gatggcggtc atcaccagtt ccctttacaa    360
ttctttatcg actataaagg ttccagtttt gtttcgccag caacaagaaa acaagaatcc    420
agatatagac cccagttatg gaataagcgc atcctgaaag ataacgtcaa ggacttactt    480
tctgtgagct acaacgagtt tattgatcct aaggatgact ccaagctttt ccaaacgctg    540
gtcaacctac aaaagtttgg tatcgctttc atttccggta ctccttcatc ctcctctgaa    600
ggccttacca tacaaaagat ctgtgaaagg atcggaccca taagatcgac tgtacatggt    660
gaaggtacat ttgacgtgaa tgcatcccaa gcgacaagtg ttaatgccca ttatgccaat    720
aaagacttgc cgctacatac ggatttacca tttttagaaa atgtgccagg tttccagatt    780
ctacaatctc tacctgctac agaaggggaa gatcccaata ctagacccat gaattacttc    840
gtggacgcat tttatgctac ccgtaatgtt agagaatcgg attttgaggc ttatgaggct    900
ttacaaattg ttcctgtaaa ttatatatat gaaaacggcg ataagaggta ctaccaatcc    960
aaacctttaa tcgaacatca cgacattaac gaggacaata ctcttctggg taattatgag   1020
gccttgatta aatgcattaa ctactctcca ccataccaag cacctttcac tttcggaatt   1080
tatgataagc cctcagatct aaataataat ctggacttga atttaattac caccccagca   1140
aaactaacag agagattttt gtttaagtct ttcattaggg ggttgaactt gttcgagagt   1200
```

-continued

| | |
|---|---|
| catatcaatg acttcaacaa tcaatttaga ttgcagttgc ccgaaaactg ttgtgttatc | 1260 |
| tttaacaaca ggagaatttt gcatgctaac tctttaacaa gctcaaacca gcaatggtta | 1320 |
| aagggttgct atttcgattc tgatactttc aagagtaaat taaagttctt ggaagagaag | 1380 |
| tttcctcatg acaaa | 1395 |

<210> SEQ ID NO 20
<211> LENGTH: 252
<212> TYPE: DNA
<213> ORGANISM: Saccharomyces cerevisiae

<400> SEQUENCE: 20

| | |
|---|---|
| atgacgagaa caaacaagtg gaccgaacgt gaaggaaagg ctgatccaaa gtacttttcg | 60 |
| cacactggta actacggtga atctccaaat cacatcaaga agcaaggttc cggcaagggt | 120 |
| aattggggta agccaggcga tgagattgat gacttaattg ataatggtga ataccccca | 180 |
| gtgttcaaga agatagaag aggctcaaat ttgcaatcgc atgaacaaaa gtttgaaaac | 240 |
| gtccaaaagg aa | 252 |

<210> SEQ ID NO 21
<211> LENGTH: 2706
<212> TYPE: DNA
<213> ORGANISM: Saccharomyces cerevisiae

<400> SEQUENCE: 21

| | |
|---|---|
| atgccgccag ctagtactag tactaccaat gatatgataa ccgaagaacc tacttctcca | 60 |
| caccaaatcc caaggcttac aaggagactt acggggttc ttccccaaga atcaagtca | 120 |
| attgacacga tgattccttt aaagtcaaga gcgttatgga ataagcatca agtcaaaaaa | 180 |
| tttaacaagg cagaagattt tcaagataga ttcattgacc atgtgaaaac tacattagca | 240 |
| cgttccctat ataattgtga tgacatggct gcttatgaag ctgcttcgat gagtattcgt | 300 |
| gacaatttgg tcattgactg gaacaaaact cagcagaaat tcaccacaag agacccaaag | 360 |
| agagtttact atttgtcttt ggagttttg atgggtaggg cttggataa tgccctgatt | 420 |
| aatatgaaga ttgaagatcc ggaagaccct gctgcctcaa agggaaaacc aagagaaatg | 480 |
| attaagggg ctttggatga tttaggtttc aagttagagg atgtcttgga ccaagaaccg | 540 |
| gacgcaggtt taggtaatgg tggtctaggt cgtcttgcag cttgcttcgt cgactcaatg | 600 |
| gcaacggaag gcatccctgc ctggggttat ggtctacgtt atgagtatgg tatctttgct | 660 |
| caaaagatta ttgacggtta ccaggtggaa actccagatt actggttaaa ttctggtaat | 720 |
| ccatgggaaa ttgaacgtaa cgaagtgcaa attcctgtca cctttatgg ttatgttgat | 780 |
| agaccagaag gcggtaaaac tacactgagt gcgtcacaat ggatcggtgg ggaaagagtt | 840 |
| cttgctgtcg cgtatgattt cccagttccg ggtttcaaga cttccaatgt aaataactta | 900 |
| agactatggc aagcaaggcc aacaacagaa tttgattttg caaaattcaa taatggtgac | 960 |
| tataaaaact ctgtggctca gcaacaacgc gcagagtcta taaccgctgt gttgtatcca | 1020 |
| aacgataact ttgctcaagg taaggagttg aggttgaaac agcagtactt ctggtgtgct | 1080 |
| gcatccttac acgacatctt aagaagattc aaaaaatcca agaggccatg gactgaattt | 1140 |
| cctgaccaag tggctattca gttgaatgat actcatccaa ctttagccat cgttgaatta | 1200 |
| cagagagttt tggtcgatct agaaaaacta gattggcacg aggcttggga catcgtgacc | 1260 |
| aagactttg cttatactaa ccacactgtt atgcaagagg ccctggaaaa atggccgtc | 1320 |
| ggcctctttg gccatttgct acccagacat ttggaaatta tatatgatat caactggttc | 1380 |

```
ttcttgcaag atgtggccaa aaaattcccc aaggatgttg atcttttgtc tcgtatatcc    1440
atcatcgaag aaaactctcc agaaagacag atcagaatgg ccttttggc tattgttggt    1500 tcacacaagg ttaatggtgt tgctgaattg cactctgaat taatcaaaac gaccatattt    1560
aaagattttg tcaagttcta tggtccatca agtttgtca atgtcactaa cggtatcaca    1620
ccaaggagat ggttgaagca agctaaccct tcattggcta aactgatcag tgaaacccctt   1680 aacgatccaa cagaggagta tttgttggac atggccaaac tgacccagtt gggaaaatat    1740
gttgaagata aggagttttt gaaaaatgg aaccaagtca agcttaataa taagatcaga    1800
ttagtagatt taatcaaaaa ggaaaatgat ggagtagaca tcattaacag agagtatttg    1860
gacgacacct tgtttgatat gcaagttaaa cgtattcatg aatataagcg tcaacagcta    1920
aacgtctttg gtattatata ccgttacctg gcaatgaaga atatgctgaa gaacggtgct    1980
tcgatcgaag aagttgccaa gaaatatcca cgcaaggttt caatctttgg tggtaagagt    2040
gctcctggtt actacatggc taagctgatc ataaaattga tcaactgtgt tgctgacatt    2100
gttaataacg acgagtcaat tgagcatttg ttgaaggttg tctttgttgc tgattataat    2160
gtttctaagg ctgaaatcat tattccagca agtgacttga gtgagcatat ttctactgct    2220
ggtactgaag cgtctggtac ttctaatatg aagtttgtta tgaacggtgg tttgattatt    2280
ggtactgttg atggtgccaa tgtggaaatc acaagggaaa ttggtgaaga taatgtcttc    2340
ttgtttggta acctaagtga aaatgtcgaa gaattgagat acaaccatca ataccatcca    2400
caagatttac catctagttt ggattctgtt ttatcctaca ttgaaagtgg acaattttct    2460
ccagaaaatc caaatgaatt caaacccttta gtcgacagta ttaagtacca cggcgattat    2520
tacctggtca gtgatgactt tgaatccttat ctggccaccc atgaattagt ggaccaggag    2580
ttccacaatc aaaggtcaga atggttaaaa aagagtgtcc tgagcgttgc aaacgtcggc    2640
ttctttagca gtgatcgttg tatcgaggaa tactccgata ccatttggaa cgttgaacca    2700
gtgact                                                              2706
```

<210> SEQ ID NO 22
<211> LENGTH: 585
<212> TYPE: DNA
<213> ORGANISM: Saccharomyces cerevisiae

<400> SEQUENCE: 22

```
atgacagatc cccacttgaa cacgccccaa gtgagcacgt cacccacatt tgaaagatca    60
caggacttcc tcaacatcga cgaaccgccc tgtgcacagg aaacacctag tgtttctaca   120
ttcaacctcc cgggtccaag cgctcccgct caaagcgtag acaagccagt ccccatgatt   180
agacggcggt ctaccaatta tatggacgca ctaaattcca gggaacaagc ccgggaacgc   240
gaaagcagta tcggggagca cgccccggga gccgaacgta ggagtagcgg acccatggat   300
ttccagaata ctatccacaa tatgcaatac aggaccacta cgactctga cctgagccac   360 gctggcgtgg atatgggtga ctccatctcc catacaccga tctgttctcg tgctggcaac   420
agacccattt tcaaaaactc gtaccttgac aacaacagca atggtaacag cgcaagagtc   480
ccacacggct ctcctccaca gttgggcacg cgtagaaagt cgtctttta gtacgaggac   540 tttaagaagg acatctataa ccagcttcac atgtttggag agaag                  585
```

<210> SEQ ID NO 23
<211> LENGTH: 765
<212> TYPE: DNA

<213> ORGANISM: Saccharomyces cerevisiae

<400> SEQUENCE: 23

```
atggtgaaat tacaaaggtt tagcgaaaag aaaagcctca tacacgaatt cggcaagttt       60
atccttgaaa agcaagaatc ggcgttaacg ggcgacgctg atgcagtgtt caatatcgcc      120
atcagtggag gatcgatgaa ccaagcgctg tacgaaagtt tggtaaatga caaaaacatt      180
tttccacata ttaagtggcc acaatggaga atcttcttct gtgacgaaag attggttcca      240
tttgaggatc cgcaaagtaa ctatggtcag ttcaaaaaaa cagttttgga cccgctagtg      300
catcagggca accaattgaa cttaggcccc actgtataca ctatcaacga atcattaatc      360
ggtggcggtg aaacggccaa tagaaagatt gccgaagaat acgcttccat gctgcctgca      420
tcattcgacc taatcttact cggatgcgga gaagatggac atacatgctc gttgtttccc      480
ggggttgaat ttaattacct tgtagaagag atggaccgca aggttttatg gtgtaataat      540
tcgcccaagg cacccaagga caggatcacc tttacattag cagtagtagc cgaggctaaa      600
agtgtgtgct ttctcgttag gggagctgct aaaaaggcta tcatgcatga cgtgttaatc      660
gtaaaaaata gcgaactacc tagtgtgctg gttaatgaaa tggtcggaac caaagtaact      720
tggtttctcg acgacgaagc tggcgccttg attcctgaaa actgc                      765
```

<210> SEQ ID NO 24
<211> LENGTH: 963
<212> TYPE: DNA
<213> ORGANISM: Saccharomyces cerevisiae

<400> SEQUENCE: 24

```
atgactatcg ctaaagatta cagaacaatt tatagaaacc aaatcaaaaa gcagatacga       60
ctaaatcagg agcatttgca aagcttgaca catctaggct cacaaatcaa tttcgaggtg      120
gatcctccca aattaccgga tccggatcct gctcgaaaag tattttttctt tgatatcgat      180
aacactttgt acagaaaatc tacgaaggta caattgctca tgcaacaatc attatcaaat      240
ttctttaaat acgaattggg gtttgacgac gatgaggcag aacgcctaat cgaatcgtat      300
tatcaagaat atggattatc cgtgaaaggt ttaataaaga ataaacaaat tgatgacgtc      360
ctacaatata atacattcat cgatgattcc ttaccttttgc aagactattt aaagcctgat      420
tggaagttaa gggagctgct gatcaattta agaaaaaga agctcggcaa atttgacaaa      480
ctatggctgt ttacaaactc gtacaaaaat catgccatca gatgtgttaa aatattaggt      540
attgctgatc tatttgacgg cataacctat tgccactacg acagacccat cgaggaagaa      600
ttcatttgca agccagatcc aaaattcttc gaaacagcta aattgcaaag tgggttgtcg      660
agctttgcaa atgcctggtt tattgatgac aacgaaagca atgtgcggag cgcgttgagc      720
atggggatgg ccatgttatc ccatttgata gaggattacc aatatgagtc agaaaatatt      780
gttactaagg accacaaaaa taagcaacaa ttttccatat tgaaagatat ccttgagatt      840
ccattgataa tggacgttga agtttaccgt ccatcctcta ttgccataaa ggaaatggaa      900
gagttggaag aggaaggggca agcagtcaac tggtcaaatc aacagatcaa tgttcagtca      960
tca                                                                   963
```

<210> SEQ ID NO 25
<211> LENGTH: 327
<212> TYPE: DNA
<213> ORGANISM: Saccharomyces cerevisiae

<400> SEQUENCE: 25

```
atgtctgacg caggtagaaa aggattcggt gaaaaagctt ctgaagcttt gaagccagac      60
tctcaaaagt catacgctga acaaggtaag gaatacatca ctgacaaggc cgacaaggtc     120
gctggtaagg ttcaaccaga agacaacaag ggtgtcttcc aaggtgtcca cgactctgcc     180
gaaaaaggca aggataacgc tgaaggtcaa ggtgaatctt ggcagaccaa gctagagat      240 tacatgggag ccgccaagtc caagttgaac gatgccgtcg aatatgtttc cggtcgtgtc     300
cacggtgaag aagacccaac caagaag                                         327
```

<210> SEQ ID NO 26
<211> LENGTH: 1926
<212> TYPE: DNA
<213> ORGANISM: Saccharomyces cerevisiae

<400> SEQUENCE: 26

```
atgtcaaaag ctgttggtat tgatttaggt acaacctatt catgtgttgc tcattttgca      60
aacgataggg ttgaaattat cgctaacgat caaggtaata aacgacgcc ttcttatgtg      120 gcttttactg acacagaaag gctaattggt gacgctgcga agaatcaagc tgcgatgaac     180
ccacataata cagtattcga tgctaagcgt ctgatcggac gtaaattcga tgatccagaa     240
gtgacgaacg atgctaagca ttacccattc aaagtgattg acaagggagg taaaccggta     300
gtgcaagtgg aatataaagg cgagacaaag acatttactc agaagaaat ttcctcaatg      360 atcttgacaa agatgaagga gactgctgag aacttttag gaacagaagt gaaagatgct      420
gtagtaacgt ttccagccta tttcaacgat tcacaaaggc aagcaacaaa agatgccggt     480
acaatcgcgg gcttgaacgt tcttcgtatc attaatgaac ctacagctgc cgctattgcg     540
tatgggctgg acaagaaatc gcagaaggag cacaacgtct tgatctttga tttaggtggt     600
ggtacttttg atgtctctct gctatccata gatgaaggtg tctttgaggt taaggctact     660
gctggtgaca ctcacttggg tggtgaagat ttcgatagta ggctggttaa ctttctagcc     720
gaggagttca aaagaaaaaa taaaaaggat ctaacaacta ccaaaggtc cctaaggagg      780 ttaaggaccg ccgctgaaag ggccaagaga actctgtctt cgtctgctca gacatctata     840
gaaatagatt cattatttga gggtatcgat ttctatactt ccattacaag ggcaagattt     900
gaagaattat gtgctgattt gtttagatct acattggagc cagtggaaaa agttttggct     960
gattcaaaat tagataagtc acaaattgat gaaattgtac ttgttggtgg ttcaacaaga    1020
attccaaaag tacaaaaact ggtttctgat tttttcaatg gtaaagaacc aaaccgttcg    1080
attaaccctg atgaggccgt cgcttatggt gctgccgtac aggctgccat cttaacgggt    1140
gaccagtcgt cgacgaccca agatttactg ttgctggatg ttgcaccatt atctctaggt    1200
attgaaactg caggtggtat tatgacaaag ttgatcccaa gaaattcgac tatcccaaca    1260
aaaaaatcgg aagtgttttc cacctacgct gacaaccaac ctggtgtgtt gatacaagtt    1320
tttgagggtg aaaggacaag gacaaaagac aacaatctac tgggtaaatt tgagttgagc    1380
ggtattccac ccgctccaag aggcgtacca caaattgaag ttacatttga tatcgatgca    1440
aatggtattc tgaacgtatc tgccgttgaa aaaggtactg gtaaatctaa caagattaca    1500
attactaacg ataagggaag attatcgaag gaagatatcg ataaaatggt tgctgaggca    1560
gaaaagttca aggccgaaga tgaacaagaa gctcaacgtg ttcaagctaa gaatcagcta    1620
gaatcgtacg cgtttactt gaaaaattct gtgagcgaaa ataacttcaa ggagaaggtg    1680
ggtgaagagg atgccaggaa attggaagcc gccgcccaag atgctataaa ttggttagat    1740
```

```
gcttcgcaag cggcctccac cgaggaatac aaggaaaggc aaaaggaact agaaggtgtt    1800 gcaaaccccca ttatgagtaa attttacgga gctgcaggtg gtgccccagg agcaggccca    1860
gttccgggtg ctggagcagg ccccactgga gcaccagaca acggcccaac ggttgaagag    1920
gttgat                                                                1926

<210> SEQ ID NO 27
<211> LENGTH: 444
<212> TYPE: DNA
<213> ORGANISM: Saccharomyces cerevisiae

<400> SEQUENCE: 27
atgttgtcta acgctaagct ccttctatca ttggccatgg cctctacggc tctcggattg      60
gtatctaatt ctagttcctc tgtaatcgtg gtaccatcaa gcgatgctac tattgccggt     120
aacgatacag ccacgccagc accagagcca tcatccgccg ctccaatatt ctacaactcg     180
actgctactg caacacagta cgaagttgtc agtgaattca ctacttactg cccagaacca     240
acgactttcg taacgaatgg cgctacattc actgttactg ccccaactac gttaacaatt     300
accaactgtc cttgcactat cgagaagcct acttcagaaa catcggtttc ttctacacat     360
gatgtggaga caaattctaa tgctgctaac gcaagagcaa tcccaggagc cctaggtttg     420
gctggtgcag ttatgatgct ttta                                           444

<210> SEQ ID NO 28
<211> LENGTH: 1179
<212> TYPE: DNA
<213> ORGANISM: Saccharomyces cerevisiae

<400> SEQUENCE: 28
atgtcatcaa gaataattgt cggcagtgca gcattggcag ctgccatcac agctagcatc      60
atggtcagag aacagaaggc caagggtcag agaagagagg gcaacgtctc cgcttactac     120
aacggccagg agtacggcag ttcagcaccc ccacagttgg gaaagctaca taacataaag     180
caaggcataa aggaagatgc cttgtcgtta aaagacgcgc ttctgggcgt atctcaaaag     240
gctagggaag aggctccaaa ggtaactaag cgtgtgatat caccggaaga ggatgctcag     300
acacgcaagc agctaggcca aaaagccaag gattcttcct cgcaaagcat cttcaattgg     360
gggtttagtg aggctgaaag aaggaaagcc atagccatcg gggaatttga tactgctaag     420
aagcgtttcg aagaggcagt ggatcgtaat gagaaggagc tcttgtccac ggtgatgaga     480
gagaagaagg ccgctctgga cagagcatcc attgagtacg aaaggtacgg agagccagag     540
gactttaatg agctttcgga caagctagac caacaggaaa ggaacagtaa tcctttgaaa     600
cgcctgttga agaataacac gggtgacgct aatactgaag aagccgctgc aagaagtgtc     660
caaggctggg gtgatacggc acaggagttt ggtagagaag agttggagga agccaagaga     720
aatgcttctt cagagccaag cgaggcgcaa aaacgtcttg acgagctgaa gaagatcaag     780
gaaaagggct ggtttggtta caacaaaggg gagcaaagcg agcaacagat tgctgaacgg     840
gtagccagag gttagaagg atggggtgaa acagccgctc aacttttccaa ggacgaaatg     900 gacgatttaa gatggaatta tgagaattca agaaacaac tggataagaa cgtgtccgat     960
gccatggact cgttatctaa ggcgaaggag gacttgaaac agtacggcag ccactggtgg    1020
tctggatgga cttccaaggt cgacaatgac aagcaggctt taaagatgga ggcccaaaag    1080
aagtacgatg aagcgttgaa aaagtacgat gaagccaaga caaattcaa agaatggaat    1140 gataagggtg atggtaaatt ctggagctcg aaaaaggac                            1179
```

<210> SEQ ID NO 29
<211> LENGTH: 506
<212> TYPE: PRT
<213> ORGANISM: Saccharomyces cerevisiae

<400> SEQUENCE: 29

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
            20                  25                  30

Ser Asp Gly Lys Thr Ile Glu Thr Val Asn Pro Ala Thr Gly Glu Pro
        35                  40                  45

Ile Thr Ser Phe Gln Ala Ala Asn Glu Lys Asp Val Asp Lys Ala Val
    50                  55                  60

Lys Ala Ala Arg Ala Ala Phe Asp Asn Val Trp Ser Lys Thr Ser Ser
65                  70                  75                  80

Glu Gln Arg Gly Ile Tyr Leu Ser Asn Leu Leu Lys Leu Ile Glu Glu
                85                  90                  95

Glu Gln Asp Thr Leu Ala Ala Leu Glu Thr Leu Asp Ala Gly Lys Pro
            100                 105                 110

Phe His Ser Asn Ala Lys Gln Asp Leu Ala Gln Ile Ile Glu Leu Thr
        115                 120                 125

Arg Tyr Tyr Ala Gly Ala Val Asp Lys Phe Asn Met Gly Glu Thr Ile
    130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Arg Lys Met Gln Gly Ala Leu Ala Ala Gly Asn Thr Val Ile Ile Lys
            180                 185                 190

Pro Ala Glu Asn Thr Ser Leu Ser Leu Leu Tyr Phe Ala Thr Leu Ile
        195                 200                 205

Lys Lys Ala Gly Phe Pro Pro Gly Val Val Asn Val Ile Pro Gly Tyr
    210                 215                 220

Gly Ser Val Val Gly Lys Ala Leu Gly Thr His Met Asp Ile Asp Lys
225                 230                 235                 240

Ile Ser Phe Thr Gly Ser Thr Lys Val Gly Gly Ser Val Leu Glu Ala
                245                 250                 255

Ser Gly Gln Ser Asn Leu Lys Asp Ile Thr Leu Glu Cys Gly Gly Lys
            260                 265                 270

Ser Pro Ala Leu Val Phe Glu Asp Ala Asp Leu Asp Lys Ala Ile Glu
        275                 280                 285

Trp Val Ala Asn Gly Ile Phe Phe Asn Ser Gly Gln Ile Cys Thr Ala
    290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
                325                 330                 335

Asp Pro Phe Asp Glu Lys Cys Ile Val Gly Pro Val Ile Ser Ser Thr
            340                 345                 350

Gln Tyr Asp Arg Ile Lys Ser Tyr Ile Glu Arg Gly Lys Lys Glu Glu
        355                 360                 365

Lys Leu Asp Met Phe Gln Thr Ser Glu Phe Pro Ile Gly Gly Ala Lys

```
              370                 375                 380
Gly Tyr Phe Ile Pro Pro Thr Ile Phe Thr Asp Val Pro Glu Thr Ser
385                 390                 395                 400

Lys Leu Leu Arg Asp Glu Ile Phe Gly Pro Val Val Val Ser Lys
            405                 410                 415

Phe Thr Asn Tyr Asp Asp Ala Leu Lys Leu Ala Asn Asp Thr Cys Tyr
                420                 425                 430

Gly Leu Ala Ser Ala Val Phe Thr Lys Asp Val Lys Lys Ala His Met
            435                 440                 445

Phe Ala Arg Asp Ile Lys Ala Gly Thr Val Trp Ile Asn Gln Thr Asn
450                 455                 460

Gln Glu Glu Ala Lys Val Pro Phe Gly Gly Phe Lys Met Ser Gly Ile
465                 470                 475                 480

Gly Arg Glu Ser Gly Asp Thr Gly Val Asp Asn Tyr Leu Gln Ile Lys
            485                 490                 495

Ser Val His Val Asp Leu Ser Leu Asp Lys
            500                 505

<210> SEQ ID NO 30
<211> LENGTH: 391
<212> TYPE: PRT
<213> ORGANISM: Saccharomyces cerevisiae

<400> SEQUENCE: 30

Met Glu Asn Thr Thr Asn Arg Asn Thr Ala Gly Val Leu Thr Ser Ser
1               5                   10                  15

Asn Gly Asn Phe Ala Thr Asn Ser Val Ala Ala Ser Thr Pro Lys Arg
            20                  25                  30

Ser Lys Ser Ala Arg Arg Lys Thr Phe Lys Cys Thr Gly Tyr Asp Gly
        35                  40                  45

Cys Thr Met Ser Phe Thr Arg Ala Glu His Leu Ala Arg His Ile Arg
    50                  55                  60

Lys His Thr Gly Glu Lys Pro Phe Gln Cys Pro Ala Cys Leu Lys Phe
65                  70                  75                  80

Phe Ser Arg Val Asp Asn Leu Lys Gln His Arg Glu Ser Val His Ala
                85                  90                  95

His Lys Asn His His Ser Thr Ser Ser His Gln Arg Lys Pro Ser Ser
            100                 105                 110

Ser Ser Leu Ser Ser Ser Ser Ala Ser Ser Ser Ser Ala Ser
        115                 120                 125

Ser Ser Thr Ser Tyr Ser Asp Pro Tyr Arg Lys Thr Asn Ile Asn Ser
    130                 135                 140

Gly Asn Met Pro Met Met Ala Glu Asn Glu Lys Ala Pro Gln Ile Ile
145                 150                 155                 160

His Ser Ser Pro Glu Phe Ile Thr Ser Thr Arg Ser Ile Pro Pro Ile
                165                 170                 175

Ser Pro Arg Ser Ile Tyr Asn Thr Gln Arg Gln Gln His Gln
            180                 185                 190

Gln Gln His Gln Gln Ala Pro Tyr Tyr Phe Pro Ser His Pro Ile Thr
        195                 200                 205

Asp Ser Tyr Tyr Gln Tyr Pro Leu Pro Ser Asn Asn Asn Thr Ile Asn
    210                 215                 220

Tyr Leu Pro Ser Val Asp Val Gln Tyr Pro Leu Asn Val Ser Pro Ser
225                 230                 235                 240
```

```
Ser Thr Ser His Pro Ala Ser Glu Val Ile Ile Ser Ser Phe Pro Pro
                245                 250                 255

Arg Ser Met Pro Ser Thr Ser Phe Lys Tyr Lys Asp Ser Ala Asp Phe
            260                 265                 270

Gln Ala Arg Thr Thr Met Asn Lys Tyr Asn Ile Arg Pro Ser Asn Ile
        275                 280                 285

Asn Val Asn Thr Ser Asn Ile Asn Asn His Leu Asp Ser Phe Ser Pro
    290                 295                 300

Pro Phe Ser Pro Ser Thr Val Ala Glu Ala Lys Pro Ile Ile Leu
305                 310                 315                 320

Pro Gln Tyr Gln Gln Ala Phe Ser Gln Pro Pro Asn Gly Asn Lys Asn
            325                 330                 335

Asn Asn Met Ser Ser Ser Lys Asn Gly Gly Lys Gly Gly Glu Asn Phe
        340                 345                 350

Lys Asn Thr Asp Asp Arg Asn Asp Asn Asn Lys Lys Arg Ser Glu
    355                 360                 365

Thr Leu Ser Glu Ser Asp Ile Ser Val Asn Thr Asn Lys Lys Arg Leu
            370                 375                 380

Ser Val Asp Tyr Ile Leu Thr
385                 390

<210> SEQ ID NO 31
<211> LENGTH: 93
<212> TYPE: PRT
<213> ORGANISM: Saccharomyces cerevisiae

<400> SEQUENCE: 31

Met Leu Arg Thr Thr Phe Leu Arg Thr Pro Arg Gln Leu Met Arg Lys
1               5                   10                  15

Ser Pro Arg Ala Ser Phe Ser Ile Val Thr Arg Ala Ala Phe Pro His
            20                  25                  30

Leu Lys Asn Asn Gln Asp Glu Ala Glu Lys Lys Glu Gln Gly Leu Phe
        35                  40                  45

Asp Ser Asn Lys Lys Arg Leu Asp Thr Leu Glu His Gly Lys Asn Pro
    50                  55                  60

Asp Tyr Lys Gln Pro Gly Met Glu Asp Leu Lys Lys Gly Asp Asp
65                  70                  75                  80

Ala Arg Ile Glu Gln Asn Arg Pro Asp Asp Gly Val Tyr
            85                  90

<210> SEQ ID NO 32
<211> LENGTH: 161
<212> TYPE: PRT
<213> ORGANISM: Saccharomyces cerevisiae

<400> SEQUENCE: 32

Met Thr Lys Lys Asp Lys Lys Glu Val Lys Val Gln Thr Val Thr Thr
1               5                   10                  15

Glu Asp Gly Glu Thr Val Lys Val Phe Glu Asp Leu Gln Gly Phe Glu
            20                  25                  30

Thr Phe Ile Ala Asn Glu Thr Glu Asp Asp Asp Phe Asp His Leu His
        35                  40                  45

Cys Lys Leu Asn Tyr Tyr Pro Pro Phe Val Leu His Glu Ser His Glu
    50                  55                  60

Asp Pro Glu Lys Ile Ser Asp Ala Ala Asn Ser His Ser Lys Lys Phe
65                  70                  75                  80
```

```
Val Arg His Leu His Gln His Ile Glu Lys His Leu Leu Lys Asp Ile
             85                  90                  95

Lys Gln Ala Val Arg Lys Pro Glu Leu Lys Phe His Gly Lys Ser Lys
        100                 105                 110

Glu Glu Thr Phe Asp Lys Ile Thr Trp His Tyr Gly Glu Glu Thr Glu
        115                 120                 125

Tyr His Gly Arg Pro Phe Lys Ile Asp Val Gln Val Cys Thr His
        130                 135                 140

Glu Asp Ala Met Val Phe Val Asp Tyr Lys Thr His Pro Val Gly Ala
145                 150                 155                 160

Asn

<210> SEQ ID NO 33
<211> LENGTH: 410
<212> TYPE: PRT
<213> ORGANISM: Saccharomyces cerevisiae

<400> SEQUENCE: 33

Met Phe Ser Ile Phe Asn Ser Pro Cys Val Phe Glu Gln Leu Pro Ser
1               5                   10                  15

Phe Ser Gln Pro Leu His Ser Arg Tyr Phe Asp Cys Ser Ser Pro Val
            20                  25                  30

Ser Tyr Tyr Pro Glu Cys Lys Arg Arg Lys Ala Ile Lys Ala Asn Leu
        35                  40                  45

Arg Ala Pro Lys Lys Ser Asp Ala Asn Cys Ser Glu Pro Leu Arg Tyr
    50                  55                  60

Ala Leu Ala Glu Thr Pro Asn Gly Tyr Thr Leu Ser Leu Ser Lys Arg
65                  70                  75                  80

Ile Pro Tyr Glu Leu Phe Ser Lys Tyr Val Asn Glu Lys Leu Gly Glu
                85                  90                  95

Leu Lys Glu Asn His Tyr Arg Pro Thr Tyr His Val Val Gln Asp Phe
            100                 105                 110

Phe Gly Asn Gln Tyr Tyr Val Glu Asp Glu Ala Asp Glu Asp Ala Leu
        115                 120                 125

Leu Arg Ser Ala Leu Lys Asp Leu Asp Phe Arg Ala Ile Gly Lys Lys
    130                 135                 140

Ile Ala Lys Asp Leu Phe Gln Asp Tyr Glu Ile Glu Leu Asn His Arg
145                 150                 155                 160

Gly Asp Glu Leu Ser Ile Leu Ser Lys Lys Asp Lys Ile Phe Lys Glu
                165                 170                 175

Phe Ser Leu Asp Gln Val Phe Glu Asp Val Phe Val Ile Gly Cys Gly
            180                 185                 190

Val Glu Asn Ile Asp Asp Gly Ser Arg Glu Lys Tyr Ala Leu Leu Lys
        195                 200                 205

Ile Gly Leu Val Lys His Glu Glu Ile Ser Glu Gly Gly Ile Asn
    210                 215                 220

Glu Pro Lys Met Pro Ile Ile Glu Ser Lys Ile Asp Glu Ser His Asp
225                 230                 235                 240

Asp Val Asn Met Ser Glu Ser Leu Lys Glu Glu Ala Glu Lys Ala
                245                 250                 255

Lys Glu Pro Leu Thr Lys Glu Asp Gln Ile Lys Lys Trp Ile Glu Glu
            260                 265                 270

Glu Arg Leu Met Gln Glu Glu Ser Arg Lys Ser Glu Gln Glu Lys Ala
        275                 280                 285
```

Ala Lys Glu Asp Glu Glu Arg Gln Lys Lys Glu Ala Arg Leu
290                 295                 300

Lys Ala Arg Lys Glu Ser Leu Ile Asn Lys Gln Lys Thr Lys Arg Ser
305                 310                 315                 320

Gln Gln Lys Lys Leu Gln Asn Ser Lys Ser Leu Pro Ile Ser Glu Ile
            325                 330                 335

Glu Ala Ser Asn Lys Asn Asn Ser Asn Ser Gly Ser Ala Glu Ser
            340                 345                 350

Asp Asn Glu Ser Ile Asn Ser Asp Ser Asp Thr Thr Leu Asp Phe Ser
            355                 360                 365

Val Ser Gly Asn Thr Leu Lys Lys His Ala Ser Pro Leu Leu Glu Asp
370                 375                 380

Val Glu Asp Glu Glu Val Asp Arg Tyr Asn Glu Ser Leu Ser Arg Ser
385                 390                 395                 400

Pro Lys Gly Asn Ser Ile Ile Glu Glu Ile
            405                 410

<210> SEQ ID NO 34
<211> LENGTH: 111
<212> TYPE: PRT
<213> ORGANISM: Saccharomyces cerevisiae

<400> SEQUENCE: 34

Met Ser Thr Val Thr Lys Tyr Phe Tyr Lys Gly Glu Asn Thr Asp Leu
1               5                   10                  15

Ile Val Phe Ala Ala Ser Glu Glu Leu Val Asp Glu Tyr Leu Lys Asn
            20                  25                  30

Pro Ser Ile Gly Lys Leu Ser Glu Val Val Glu Leu Phe Glu Val Phe
        35                  40                  45

Thr Pro Gln Asp Gly Arg Gly Ala Glu Gly Leu Gly Ala Ala Ser
    50                  55                  60

Lys Ala Gln Val Glu Asn Glu Phe Gly Lys Gly Lys Lys Ile Glu Glu
65                  70                  75                  80

Val Ile Asp Leu Ile Leu Arg Asn Gly Lys Pro Asn Ser Thr Thr Ser
                85                  90                  95

Ser Leu Lys Thr Lys Gly Gly Asn Ala Gly Thr Lys Ala Tyr Asn
            100                 105                 110

<210> SEQ ID NO 35
<211> LENGTH: 332
<212> TYPE: PRT
<213> ORGANISM: Saccharomyces cerevisiae

<400> SEQUENCE: 35

Met Asn Asp Thr Leu Ser Ser Phe Leu Asn Arg Asn Glu Ala Leu Gly
1               5                   10                  15

Leu Asn Pro Pro His Gly Leu Asp Met His Ile Thr Lys Arg Gly Ser
            20                  25                  30

Asp Trp Leu Trp Ala Val Phe Ala Val Phe Gly Phe Ile Leu Leu Cys
        35                  40                  45

Tyr Val Val Met Phe Phe Ile Ala Glu Asn Lys Gly Ser Arg Leu Thr
    50                  55                  60

Arg Tyr Ala Leu Ala Pro Ala Phe Leu Ile Thr Phe Phe Glu Phe Phe
65                  70                  75                  80

Ala Phe Phe Thr Tyr Ala Ser Asp Leu Gly Trp Thr Gly Val Gln Ala
                85                  90                  95

```
Glu Phe Asn His Val Lys Val Ser Lys Ser Ile Thr Gly Glu Val Pro
                100                 105                 110

Gly Ile Arg Gln Ile Phe Tyr Ser Lys Tyr Ile Ala Trp Phe Leu Ser
            115                 120                 125

Trp Pro Cys Leu Leu Phe Leu Ile Glu Leu Ala Ala Ser Thr Thr Gly
130                 135                 140

Glu Asn Asp Asp Ile Ser Ala Leu Asp Met Val His Ser Leu Leu Ile
145                 150                 155                 160

Gln Ile Val Gly Thr Leu Phe Trp Val Val Ser Leu Leu Val Gly Ser
                165                 170                 175

Leu Ile Lys Ser Thr Tyr Lys Trp Gly Tyr Tyr Thr Ile Gly Ala Val
            180                 185                 190

Ala Met Leu Val Thr Gln Gly Val Ile Cys Gln Arg Gln Phe Phe Asn
        195                 200                 205

Leu Lys Thr Arg Gly Phe Asn Ala Leu Met Leu Cys Thr Cys Met Val
210                 215                 220

Ile Val Trp Leu Tyr Phe Ile Cys Trp Gly Leu Ser Asp Gly Gly Asn
225                 230                 235                 240

Arg Ile Gln Pro Asp Gly Glu Ala Ile Phe Tyr Gly Val Leu Asp Leu
                245                 250                 255

Cys Val Phe Ala Ile Tyr Pro Cys Tyr Leu Leu Ile Ala Val Ser Arg
            260                 265                 270

Asp Gly Lys Leu Pro Arg Leu Ser Leu Thr Gly Gly Phe Ser His His
        275                 280                 285

His Ala Thr Asp Asp Val Glu Asp Ala Ala Pro Glu Thr Lys Glu Ala
290                 295                 300

Val Pro Glu Ser Pro Arg Ala Ser Gly Glu Thr Ala Ile His Glu Pro
305                 310                 315                 320

Glu Pro Glu Ala Glu Gln Ala Val Glu Asp Thr Ala
                325                 330

<210> SEQ ID NO 36
<211> LENGTH: 562
<212> TYPE: PRT
<213> ORGANISM: Saccharomyces cerevisiae

<400> SEQUENCE: 36

Met Asn Val Phe Gly Lys Lys Glu Glu Lys Gln Glu Lys Val Tyr Ser
1               5                   10                  15

Leu Gln Asn Gly Phe Pro Tyr Ser His His Pro Tyr Ala Ser Gln Tyr
            20                  25                  30

Ser Arg Pro Asp Gly Pro Ile Leu Leu Gln Asp Phe His Leu Leu Glu
        35                  40                  45

Asn Ile Ala Ser Phe Asp Arg Glu Arg Val Pro Glu Arg Val Val His
    50                  55                  60

Ala Lys Gly Gly Gly Cys Arg Leu Glu Phe Glu Leu Thr Asp Ser Leu
65                  70                  75                  80

Ser Asp Ile Thr Tyr Ala Ala Pro Tyr Gln Asn Val Gly Tyr Lys Cys
                85                  90                  95

Pro Gly Leu Val Arg Phe Ser Thr Val Gly Gly Glu Ser Gly Thr Pro
            100                 105                 110

Asp Thr Ala Arg Asp Pro Arg Gly Val Ser Phe Lys Phe Tyr Thr Glu
        115                 120                 125

Trp Gly Asn His Asp Trp Val Phe Asn Asn Thr Pro Val Phe Phe Leu
    130                 135                 140
```

```
Arg Asp Ala Ile Lys Phe Pro Val Phe Ile His Ser Gln Lys Arg Asp
145                 150                 155                 160

Pro Gln Ser His Leu Asn Gln Phe Gln Asp Thr Thr Ile Tyr Trp Asp
                165                 170                 175

Tyr Leu Thr Leu Asn Pro Glu Ser Ile His Gln Ile Thr Tyr Met Phe
            180                 185                 190

Gly Asp Arg Gly Thr Pro Ala Ser Trp Ala Ser Met Asn Ala Tyr Ser
        195                 200                 205

Gly His Ser Phe Ile Met Val Asn Lys Glu Gly Lys Asp Thr Tyr Val
    210                 215                 220

Gln Phe His Val Leu Ser Asp Thr Gly Phe Glu Thr Leu Thr Gly Asp
225                 230                 235                 240

Lys Ala Ala Glu Leu Ser Gly Ser His Pro Asp Tyr Asn Gln Ala Lys
                245                 250                 255

Leu Phe Thr Gln Leu Gln Asn Gly Glu Lys Pro Lys Phe Asn Cys Tyr
            260                 265                 270

Val Gln Thr Met Thr Pro Glu Gln Ala Thr Lys Phe Arg Tyr Ser Val
        275                 280                 285

Asn Asp Leu Thr Lys Ile Trp Pro His Lys Glu Phe Pro Leu Arg Lys
290                 295                 300

Phe Gly Thr Ile Thr Leu Thr Glu Asn Val Asp Asn Tyr Phe Gln Glu
305                 310                 315                 320

Ile Glu Gln Val Ala Phe Ser Pro Thr Asn Thr Cys Ile Pro Gly Ile
                325                 330                 335

Lys Pro Ser Asn Asp Ser Val Leu Gln Ala Arg Leu Phe Ser Tyr Pro
            340                 345                 350

Asp Thr Gln Arg His Arg Leu Gly Ala Asn Tyr Gln Gln Leu Pro Val
        355                 360                 365

Asn Arg Pro Arg Asn Leu Gly Cys Pro Tyr Ser Lys Gly Asp Ser Gln
370                 375                 380

Tyr Thr Ala Glu Gln Cys Pro Phe Lys Ala Val Asn Phe Gln Arg Asp
385                 390                 395                 400

Gly Pro Met Ser Tyr Tyr Asn Phe Gly Pro Glu Pro Asn Tyr Ile Ser
                405                 410                 415

Ser Leu Pro Asn Gln Thr Leu Lys Phe Lys Asn Glu Asp Asn Asp Glu
            420                 425                 430

Val Ser Asp Lys Phe Lys Gly Ile Val Leu Asp Glu Val Thr Glu Val
        435                 440                 445

Ser Val Arg Lys Gln Glu Gln Asp Gln Ile Arg Asn Glu His Ile Val
450                 455                 460

Asp Ala Lys Ile Asn Gln Tyr Tyr Tyr Val Tyr Gly Ile Ser Pro Leu
465                 470                 475                 480

Asp Phe Glu Gln Pro Arg Ala Leu Tyr Glu Lys Val Tyr Asn Asp Glu
                485                 490                 495

Gln Lys Lys Leu Phe Val His Asn Val Val Cys His Ala Cys Lys Ile
            500                 505                 510

Lys Asp Pro Lys Val Lys Lys Arg Val Thr Gln Tyr Phe Gly Leu Leu
        515                 520                 525

Asn Glu Asp Leu Gly Lys Val Ile Ala Glu Cys Leu Gly Val Pro Trp
530                 535                 540

Glu Pro Val Asp Leu Glu Gly Tyr Ala Lys Thr Trp Ser Ile Ala Ser
545                 550                 555                 560
```

Ala Asn

<210> SEQ ID NO 37
<211> LENGTH: 465
<212> TYPE: PRT
<213> ORGANISM: Saccharomyces cerevisiae

<400> SEQUENCE: 37

```
Met Leu Arg Ser Asn Leu Cys Arg Gly Ser Arg Ile Leu Ala Arg Leu
1               5                   10                  15

Thr Thr Thr Pro Arg Thr Tyr Thr Ser Ala Ala Thr Ala Ala Ala Ala
            20                  25                  30

Asn Arg Gly His Ile Ile Lys Thr Tyr Phe Asn Arg Asp Ser Thr Thr
        35                  40                  45

Ile Thr Phe Ser Met Glu Glu Ser Ser Lys Pro Val Ser Val Cys Phe
    50                  55                  60

Asn Asn Val Phe Leu Arg Asp Ala Ser His Ser Ala Lys Leu Val Thr
65                  70                  75                  80

Thr Gly Glu Leu Tyr His Asn Glu Lys Leu Thr Ala Pro Gln Asp Ile
                85                  90                  95

Gln Ile Ser Glu Asp Gly Lys Ser Leu Val Val Lys Trp Lys Asp Gly
            100                 105                 110

Gly His His Gln Phe Pro Leu Gln Phe Phe Ile Asp Tyr Lys Gly Ser
        115                 120                 125

Ser Phe Val Ser Pro Ala Thr Arg Lys Gln Glu Ser Arg Tyr Arg Pro
    130                 135                 140

Gln Leu Trp Asn Lys Arg Ile Leu Lys Asp Asn Val Lys Asp Leu Leu
145                 150                 155                 160

Ser Val Ser Tyr Asn Glu Phe Ile Asp Pro Lys Asp Ser Lys Leu
                165                 170                 175

Phe Gln Thr Leu Val Asn Leu Gln Lys Phe Gly Ile Ala Phe Ile Ser
            180                 185                 190

Gly Thr Pro Ser Ser Ser Ser Glu Gly Leu Thr Ile Gln Lys Ile Cys
        195                 200                 205

Glu Arg Ile Gly Pro Ile Arg Ser Thr Val His Gly Glu Gly Thr Phe
    210                 215                 220

Asp Val Asn Ala Ser Gln Ala Thr Ser Val Asn Ala His Tyr Ala Asn
225                 230                 235                 240

Lys Asp Leu Pro Leu His Thr Asp Leu Pro Phe Leu Glu Asn Val Pro
                245                 250                 255

Gly Phe Gln Ile Leu Gln Ser Leu Pro Ala Thr Glu Gly Glu Asp Pro
            260                 265                 270

Asn Thr Arg Pro Met Asn Tyr Phe Val Asp Ala Phe Tyr Ala Thr Arg
        275                 280                 285

Asn Val Arg Glu Ser Asp Phe Glu Ala Tyr Glu Ala Leu Gln Ile Val
    290                 295                 300

Pro Val Asn Tyr Ile Tyr Glu Asn Gly Asp Lys Arg Tyr Tyr Gln Ser
305                 310                 315                 320

Lys Pro Leu Ile Glu His His Asp Ile Asn Glu Asp Asn Thr Leu Leu
                325                 330                 335

Gly Asn Tyr Glu Ala Leu Ile Lys Cys Ile Asn Tyr Ser Pro Pro Tyr
            340                 345                 350

Gln Ala Pro Phe Thr Phe Gly Ile Tyr Asp Lys Pro Ser Asp Leu Asn
        355                 360                 365
```

```
Asn Asn Leu Asp Leu Asn Leu Ile Thr Thr Pro Ala Lys Leu Thr Glu
        370             375             380

Arg Phe Leu Phe Lys Ser Phe Ile Arg Gly Leu Asn Leu Phe Glu Ser
385             390             395                 400

His Ile Asn Asp Phe Asn Asn Gln Phe Arg Leu Gln Leu Pro Glu Asn
                405             410             415

Cys Cys Val Ile Phe Asn Asn Arg Arg Ile Leu His Ala Asn Ser Leu
            420             425             430

Thr Ser Ser Asn Gln Gln Trp Leu Lys Gly Cys Tyr Phe Asp Ser Asp
        435             440             445

Thr Phe Lys Ser Lys Leu Lys Phe Leu Glu Gly Lys Phe Pro His Asp
450             455             460

Lys
465

<210> SEQ ID NO 38
<211> LENGTH: 84
<212> TYPE: PRT
<213> ORGANISM: Saccharomyces cerevisiae

<400> SEQUENCE: 38

Met Thr Arg Thr Asn Lys Trp Thr Glu Arg Glu Gly Lys Ala Asp Pro
1               5                   10                  15

Lys Tyr Phe Ser His Thr Gly Asn Tyr Gly Glu Ser Pro Asn His Ile
            20                  25                  30

Lys Lys Gln Gly Ser Gly Lys Gly Asn Trp Gly Lys Pro Gly Asp Glu
        35                  40                  45

Ile Asp Asp Leu Ile Asp Asn Gly Glu Ile Pro Pro Val Phe Lys Lys
    50                  55                  60

Asp Arg Arg Gly Ser Asn Leu Gln Ser His Glu Gln Lys Phe Glu Asn
65                  70                  75                  80

Val Gln Lys Glu

<210> SEQ ID NO 39
<211> LENGTH: 902
<212> TYPE: PRT
<213> ORGANISM: Saccharomyces cerevisiae

<400> SEQUENCE: 39

Met Pro Pro Ala Ser Thr Ser Thr Thr Asn Asp Met Ile Thr Glu Glu
1               5                   10                  15

Pro Thr Ser Pro His Gln Ile Pro Arg Leu Thr Arg Arg Leu Thr Gly
            20                  25                  30

Phe Leu Pro Gln Glu Ile Lys Ser Ile Asp Thr Met Ile Pro Leu Lys
        35                  40                  45

Ser Arg Ala Leu Trp Asn Lys His Gln Val Lys Lys Phe Asn Lys Ala
    50                  55                  60

Glu Asp Phe Gln Asp Arg Phe Ile Asp His Val Glu Thr Thr Leu Ala
65                  70                  75                  80

Arg Ser Leu Tyr Asn Cys Asp Asp Met Ala Ala Tyr Glu Ala Ala Ser
                85                  90                  95

Met Ser Ile Arg Asp Asn Leu Val Ile Asp Trp Asn Lys Thr Gln Gln
            100                 105                 110

Lys Phe Thr Thr Arg Asp Pro Lys Arg Val Tyr Tyr Leu Ser Leu Glu
        115                 120                 125

Phe Leu Met Gly Arg Ala Leu Asp Asn Ala Leu Ile Asn Met Lys Ile
```

```
            130                 135                 140
Glu Asp Pro Glu Asp Pro Ala Ala Ser Lys Gly Lys Pro Arg Glu Met
145                 150                 155                 160

Ile Lys Gly Ala Leu Asp Asp Leu Gly Phe Lys Leu Glu Asp Val Leu
                165                 170                 175

Asp Gln Glu Pro Asp Ala Gly Leu Gly Asn Gly Gly Leu Gly Arg Leu
            180                 185                 190

Ala Ala Cys Phe Val Asp Ser Met Ala Thr Glu Gly Ile Pro Ala Trp
        195                 200                 205

Gly Tyr Gly Leu Arg Tyr Glu Tyr Gly Ile Phe Ala Gln Lys Ile Ile
    210                 215                 220

Asp Gly Tyr Gln Val Glu Thr Pro Asp Tyr Trp Leu Asn Ser Gly Asn
225                 230                 235                 240

Pro Trp Glu Ile Glu Arg Asn Glu Val Gln Ile Pro Val Thr Phe Tyr
                245                 250                 255

Gly Tyr Val Asp Arg Pro Glu Gly Gly Lys Thr Thr Leu Ser Ala Ser
            260                 265                 270

Gln Trp Ile Gly Gly Glu Arg Val Leu Ala Val Ala Tyr Asp Phe Pro
        275                 280                 285

Val Pro Gly Phe Lys Thr Ser Asn Val Asn Asn Leu Arg Leu Trp Gln
    290                 295                 300

Ala Arg Pro Thr Thr Glu Phe Asp Phe Ala Lys Phe Asn Asn Gly Asp
305                 310                 315                 320

Tyr Lys Asn Ser Val Ala Gln Gln Arg Ala Glu Ser Ile Thr Ala
                325                 330                 335

Val Leu Tyr Pro Asn Asp Asn Phe Ala Gln Gly Lys Glu Leu Arg Leu
            340                 345                 350

Lys Gln Gln Tyr Phe Trp Cys Ala Ala Ser Leu His Asp Ile Leu Arg
        355                 360                 365

Arg Phe Lys Lys Ser Lys Arg Pro Trp Thr Glu Phe Pro Asp Gln Val
    370                 375                 380

Ala Ile Gln Leu Asn Asp Thr His Pro Thr Leu Ala Ile Val Glu Leu
385                 390                 395                 400

Gln Arg Val Leu Val Asp Leu Glu Lys Leu Asp Trp His Glu Ala Trp
                405                 410                 415

Asp Ile Val Thr Lys Thr Phe Ala Tyr Thr Asn His Thr Val Met Gln
            420                 425                 430

Glu Ala Leu Glu Lys Trp Pro Val Gly Leu Phe Gly His Leu Leu Pro
        435                 440                 445

Arg His Leu Glu Ile Ile Tyr Asp Ile Asn Trp Phe Phe Leu Gln Asp
    450                 455                 460

Val Ala Lys Lys Phe Pro Lys Asp Val Asp Leu Leu Ser Arg Ile Ser
465                 470                 475                 480

Ile Ile Glu Glu Asn Ser Pro Glu Arg Gln Ile Arg Met Ala Phe Leu
                485                 490                 495

Ala Ile Val Gly Ser His Lys Val Asn Gly Val Ala Glu Leu His Ser
            500                 505                 510

Glu Leu Ile Lys Thr Thr Ile Phe Lys Asp Phe Val Lys Phe Tyr Gly
        515                 520                 525

Pro Ser Lys Phe Val Asn Val Thr Asn Gly Ile Thr Pro Arg Arg Trp
    530                 535                 540

Leu Lys Gln Ala Asn Pro Ser Leu Ala Lys Leu Ile Ser Glu Thr Leu
545                 550                 555                 560
```

```
Asn Asp Pro Thr Glu Glu Tyr Leu Leu Asp Met Ala Lys Leu Thr Gln
            565                 570                 575
Leu Gly Lys Tyr Val Glu Asp Lys Glu Phe Leu Lys Lys Trp Asn Gln
            580                 585                 590
Val Lys Leu Asn Asn Lys Ile Arg Leu Val Asp Leu Ile Lys Lys Glu
            595                 600                 605
Asn Asp Gly Val Asp Ile Ile Asn Arg Glu Tyr Leu Asp Asp Thr Leu
            610                 615                 620
Phe Asp Met Gln Val Lys Arg Ile His Glu Tyr Lys Arg Gln Gln Leu
625                 630                 635                 640
Asn Val Phe Gly Ile Ile Tyr Arg Tyr Leu Ala Met Lys Asn Met Leu
            645                 650                 655
Lys Asn Gly Ala Ser Ile Glu Glu Val Ala Lys Lys Tyr Pro Arg Lys
            660                 665                 670
Val Ser Ile Phe Gly Gly Lys Ser Ala Pro Gly Tyr Tyr Met Ala Lys
            675                 680                 685
Leu Ile Ile Lys Leu Ile Asn Cys Val Ala Asp Ile Val Asn Asn Asp
            690                 695                 700
Glu Ser Ile Glu His Leu Leu Lys Val Val Phe Val Ala Asp Tyr Asn
705                 710                 715                 720
Val Ser Lys Ala Glu Ile Ile Pro Ala Ser Asp Leu Ser Glu His
            725                 730                 735
Ile Ser Thr Ala Gly Thr Glu Ala Ser Gly Thr Ser Asn Met Lys Phe
            740                 745                 750
Val Met Asn Gly Gly Leu Ile Ile Gly Thr Val Asp Gly Ala Asn Val
            755                 760                 765
Glu Ile Thr Arg Glu Ile Gly Glu Asp Asn Val Phe Leu Phe Gly Asn
            770                 775                 780
Leu Ser Glu Asn Val Glu Glu Leu Arg Tyr Asn His Gln Tyr His Pro
785                 790                 795                 800
Gln Asp Leu Pro Ser Ser Leu Asp Ser Val Leu Ser Tyr Ile Glu Ser
            805                 810                 815
Gly Gln Phe Ser Pro Glu Asn Pro Asn Glu Phe Lys Pro Leu Val Asp
            820                 825                 830
Ser Ile Lys Tyr His Gly Asp Tyr Tyr Leu Val Ser Asp Asp Phe Glu
            835                 840                 845
Ser Tyr Leu Ala Thr His Glu Leu Val Asp Gln Glu Phe His Asn Gln
            850                 855                 860
Arg Ser Glu Trp Leu Lys Lys Ser Val Leu Ser Val Ala Asn Val Gly
865                 870                 875                 880
Phe Phe Ser Ser Asp Arg Cys Ile Glu Glu Tyr Ser Asp Thr Ile Trp
            885                 890                 895
Asn Val Glu Pro Val Thr
            900

<210> SEQ ID NO 40
<211> LENGTH: 195
<212> TYPE: PRT
<213> ORGANISM: Saccharomyces cerevisiae

<400> SEQUENCE: 40

Met Thr Asp Pro His Leu Asn Thr Pro Gln Val Ser Thr Ser Pro Thr
1               5                   10                  15
Phe Glu Arg Ser Gln Asp Phe Leu Asn Ile Asp Glu Pro Pro Cys Ala
```

```
                    20                  25                  30
Gln Glu Thr Pro Ser Val Ser Thr Phe Asn Leu Pro Gly Pro Ser Ala
                35                  40                  45

Pro Ala Gln Ser Val Asp Lys Pro Val Pro Met Ile Arg Arg Arg Ser
     50                  55                  60

Thr Asn Tyr Met Asp Ala Leu Asn Ser Arg Glu Gln Ala Arg Glu Arg
 65                  70                  75                  80

Glu Ser Ser Ile Gly Glu His Ala Pro Gly Ala Glu Arg Arg Ser Ser
                 85                  90                  95

Gly Pro Met Asp Phe Gln Asn Thr Ile His Asn Met Gln Tyr Arg Thr
            100                 105                 110

Thr Asn Asp Ser Asp Leu Ser His Ala Gly Val Asp Met Gly Asp Ser
        115                 120                 125

Ile Ser His Thr Pro Ile Cys Ser Arg Ala Gly Asn Arg Pro Ile Phe
    130                 135                 140

Lys Asn Ser Tyr Leu Asp Asn Asn Ser Asn Gly Asn Ser Ala Arg Val
145                 150                 155                 160

Pro His Gly Ser Pro Pro Gln Leu Gly Thr Arg Arg Lys Ser Ser Phe
                165                 170                 175

Lys Tyr Glu Asp Phe Lys Lys Asp Ile Tyr Asn Gln Leu His Met Phe
            180                 185                 190

Gly Glu Lys
        195

<210> SEQ ID NO 41
<211> LENGTH: 255
<212> TYPE: PRT
<213> ORGANISM: Saccharomyces cerevisiae

<400> SEQUENCE: 41

Met Val Lys Leu Gln Arg Phe Ser Glu Lys Lys Ser Leu Ile His Glu
  1               5                  10                  15

Phe Gly Lys Phe Ile Leu Glu Lys Gln Glu Ser Ala Leu Thr Gly Asp
                 20                  25                  30

Ala Asp Ala Val Phe Asn Ile Ala Ile Ser Gly Gly Ser Met Asn Gln
             35                  40                  45

Ala Leu Tyr Glu Ser Leu Val Asn Asp Lys Asn Ile Phe Pro His Ile
         50                  55                  60

Lys Trp Pro Gln Trp Arg Ile Phe Phe Cys Asp Glu Arg Leu Val Pro
 65                  70                  75                  80

Phe Glu Asp Pro Gln Ser Asn Tyr Gly Gln Phe Lys Lys Thr Val Leu
                 85                  90                  95

Asp Pro Leu Val His Gln Gly Asn Gln Leu Asn Leu Gly Pro Thr Val
            100                 105                 110

Tyr Thr Ile Asn Glu Ser Leu Ile Gly Gly Glu Thr Ala Asn Arg
        115                 120                 125

Lys Ile Ala Glu Glu Tyr Ala Ser Met Leu Pro Ala Ser Phe Asp Leu
    130                 135                 140

Ile Leu Leu Gly Cys Gly Glu Asp Gly His Thr Cys Ser Leu Phe Pro
145                 150                 155                 160

Gly Val Glu Phe Asn Tyr Leu Val Glu Glu Met Asp Arg Lys Val Leu
                165                 170                 175

Trp Cys Asn Asn Ser Pro Lys Ala Pro Lys Asp Arg Ile Thr Phe Thr
            180                 185                 190
```

```
Leu Ala Val Ala Glu Ala Lys Ser Val Cys Phe Leu Val Arg Gly
            195                 200                 205

Ala Ala Lys Lys Ala Ile Met His Asp Val Leu Ile Val Lys Asn Ser
210                 215                 220

Glu Leu Pro Ser Val Leu Val Asn Glu Met Val Gly Thr Lys Val Thr
225                 230                 235                 240

Trp Phe Leu Asp Asp Glu Ala Gly Ala Leu Ile Pro Glu Asn Cys
                245                 250                 255

<210> SEQ ID NO 42
<211> LENGTH: 321
<212> TYPE: PRT
<213> ORGANISM: Saccharomyces cerevisiae

<400> SEQUENCE: 42

Met Thr Ile Ala Lys Asp Tyr Arg Thr Ile Tyr Arg Asn Gln Ile Lys
1               5                   10                  15

Lys Gln Ile Arg Leu Asn Gln Glu His Leu Gln Ser Leu Thr His Leu
                20                  25                  30

Gly Ser Gln Ile Asn Phe Glu Val Asp Pro Pro Lys Leu Pro Asp Pro
            35                  40                  45

Asp Pro Ala Arg Lys Val Phe Phe Asp Ile Asp Asn Thr Leu Tyr
50                  55                  60

Arg Lys Ser Thr Lys Val Gln Leu Leu Met Gln Gln Ser Leu Ser Asn
65                  70                  75                  80

Phe Phe Lys Tyr Glu Leu Gly Phe Asp Asp Glu Ala Glu Arg Leu
                85                  90                  95

Ile Glu Ser Tyr Tyr Gln Glu Tyr Gly Leu Ser Val Lys Gly Leu Ile
                100                 105                 110

Lys Asn Lys Gln Ile Asp Asp Val Leu Gln Tyr Asn Thr Phe Ile Asp
            115                 120                 125

Asp Ser Leu Pro Leu Gln Asp Tyr Leu Lys Pro Asp Trp Lys Leu Arg
        130                 135                 140

Glu Leu Leu Ile Asn Leu Lys Lys Lys Leu Gly Lys Phe Asp Lys
145                 150                 155                 160

Leu Trp Leu Phe Thr Asn Ser Tyr Lys Asn His Ala Ile Arg Cys Val
                165                 170                 175

Lys Ile Leu Gly Ile Ala Asp Leu Phe Asp Gly Ile Thr Tyr Cys His
            180                 185                 190

Tyr Asp Arg Pro Ile Glu Glu Glu Phe Ile Cys Lys Pro Asp Pro Lys
        195                 200                 205

Phe Phe Glu Thr Ala Lys Leu Gln Ser Gly Leu Ser Ser Phe Ala Asn
210                 215                 220

Ala Trp Phe Ile Asp Asp Asn Glu Ser Asn Val Arg Ser Ala Leu Ser
225                 230                 235                 240

Met Gly Met Gly His Val Ile His Leu Ile Glu Asp Tyr Gln Tyr Glu
                245                 250                 255

Ser Glu Asn Ile Val Thr Lys Asp His Lys Asn Lys Gln Gln Phe Ser
            260                 265                 270

Ile Leu Lys Asp Ile Leu Glu Ile Pro Leu Ile Met Asp Val Glu Val
        275                 280                 285

Tyr Arg Pro Ser Ser Ile Ala Ile Lys Glu Met Glu Glu Leu Glu Glu
        290                 295                 300

Glu Gly Glu Ala Val Asn Trp Ser Asn Gln Gln Ile Asn Val Gln Ser
305                 310                 315                 320
```

Ser

<210> SEQ ID NO 43
<211> LENGTH: 109
<212> TYPE: PRT
<213> ORGANISM: Saccharomyces cerevisiae

<400> SEQUENCE: 43

Met Ser Asp Ala Gly Arg Lys Gly Phe Gly Glu Lys Ala Ser Glu Ala
1               5                   10                  15

Leu Lys Pro Asp Ser Gln Lys Ser Tyr Ala Glu Gln Gly Lys Glu Tyr
            20                  25                  30

Ile Thr Asp Lys Ala Asp Lys Val Ala Gly Lys Val Gln Pro Glu Asp
        35                  40                  45

Asn Lys Gly Val Phe Gln Gly Val His Asp Ser Ala Glu Lys Gly Lys
    50                  55                  60

Asp Asn Ala Glu Gly Gln Gly Glu Ser Leu Ala Asp Gln Ala Arg Asp
65                  70                  75                  80

Tyr Met Gly Ala Ala Lys Ser Lys Leu Asn Asp Ala Val Glu Tyr Val
                85                  90                  95

Ser Gly Arg Val His Gly Glu Glu Asp Pro Thr Lys Lys
            100                 105

<210> SEQ ID NO 44
<211> LENGTH: 642
<212> TYPE: PRT
<213> ORGANISM: Saccharomyces cerevisiae

<400> SEQUENCE: 44

Met Ser Lys Ala Val Gly Ile Asp Leu Gly Thr Thr Tyr Ser Cys Val
1               5                   10                  15

Ala His Phe Ala Asn Asp Arg Val Glu Ile Ile Ala Asn Asp Gln Gly
            20                  25                  30

Asn Arg Thr Thr Pro Ser Tyr Val Ala Phe Thr Asp Thr Glu Arg Leu
        35                  40                  45

Ile Gly Asp Ala Ala Lys Asn Gln Ala Ala Met Asn Pro His Asn Thr
    50                  55                  60

Val Phe Asp Ala Lys Arg Leu Ile Gly Arg Lys Phe Asp Asp Pro Glu
65                  70                  75                  80

Val Thr Asn Asp Ala Lys His Tyr Pro Phe Lys Val Ile Asp Lys Gly
                85                  90                  95

Gly Lys Pro Val Val Gln Val Glu Tyr Lys Gly Glu Thr Lys Thr Phe
            100                 105                 110

Thr Pro Glu Glu Ile Ser Ser Met Ile Leu Thr Lys Met Lys Glu Thr
            115                 120                 125

Ala Glu Asn Phe Leu Gly Thr Glu Val Lys Asp Ala Val Val Thr Val
        130                 135                 140

Pro Ala Tyr Phe Asn Asp Ser Gln Arg Gln Ala Thr Lys Asp Ala Gly
145                 150                 155                 160

Thr Ile Ala Gly Leu Asn Val Leu Arg Ile Ile Asn Glu Pro Thr Ala
                165                 170                 175

Ala Ala Ile Ala Tyr Gly Leu Asp Lys Lys Ser Gln Lys Glu His Asn
            180                 185                 190

Val Leu Ile Phe Asp Leu Gly Gly Gly Thr Phe Asp Val Ser Leu Leu
        195                 200                 205

```
Ser Ile Asp Glu Gly Val Phe Glu Val Lys Ala Thr Ala Gly Asp Thr
    210                 215                 220

His Leu Gly Gly Glu Asp Phe Asp Ser Arg Leu Val Asn Phe Leu Ala
225                 230                 235                 240

Glu Glu Phe Lys Arg Lys Asn Lys Lys Asp Leu Thr Thr Asn Gln Arg
                245                 250                 255

Ser Leu Arg Arg Leu Arg Thr Ala Ala Glu Arg Ala Lys Arg Thr Leu
            260                 265                 270

Ser Ser Ser Ala Gln Thr Ser Ile Glu Ile Asp Ser Leu Phe Glu Gly
        275                 280                 285

Ile Asp Phe Tyr Thr Ser Ile Thr Arg Ala Arg Phe Glu Glu Leu Cys
    290                 295                 300

Ala Asp Leu Phe Arg Ser Thr Leu Glu Pro Val Glu Lys Val Leu Ala
305                 310                 315                 320

Asp Ser Lys Leu Asp Lys Ser Gln Ile Asp Glu Ile Val Leu Val Gly
                325                 330                 335

Gly Ser Thr Arg Ile Pro Lys Val Gln Lys Leu Val Ser Asp Phe Phe
            340                 345                 350

Asn Gly Lys Glu Pro Asn Arg Ser Ile Asn Pro Asp Glu Ala Val Ala
        355                 360                 365

Tyr Gly Ala Ala Val Gln Ala Ala Ile Leu Thr Gly Asp Gln Ser Ser
    370                 375                 380

Thr Thr Gln Asp Leu Leu Leu Leu Asp Val Ala Pro Leu Ser Leu Gly
385                 390                 395                 400

Ile Glu Thr Ala Gly Gly Ile Met Thr Lys Leu Ile Pro Arg Asn Ser
                405                 410                 415

Thr Ile Pro Thr Lys Lys Ser Glu Val Phe Ser Thr Tyr Ala Asp Asn
            420                 425                 430

Gln Pro Gly Val Leu Ile Gln Val Phe Glu Gly Glu Arg Thr Arg Thr
        435                 440                 445

Lys Asp Asn Asn Leu Leu Gly Lys Phe Glu Leu Ser Gly Ile Pro Pro
    450                 455                 460

Ala Pro Arg Gly Val Pro Gln Ile Glu Val Thr Phe Asp Ile Asp Ala
465                 470                 475                 480

Asn Gly Ile Leu Asn Val Ser Ala Val Glu Lys Gly Thr Gly Lys Ser
                485                 490                 495

Asn Lys Ile Thr Ile Thr Asn Asp Lys Gly Arg Leu Ser Lys Glu Asp
            500                 505                 510

Ile Asp Lys Met Val Ala Glu Ala Glu Lys Phe Lys Ala Glu Asp Glu
    515                 520                 525

Gln Glu Ala Gln Arg Val Gln Ala Lys Asn Gln Leu Glu Ser Tyr Ala
530                 535                 540

Phe Thr Leu Lys Asn Ser Val Ser Glu Asn Asn Phe Lys Glu Lys Val
545                 550                 555                 560

Gly Glu Glu Asp Ala Arg Lys Leu Glu Ala Ala Gln Asp Ala Ile
                565                 570                 575

Asn Trp Leu Asp Ala Ser Gln Ala Ala Ser Thr Glu Glu Tyr Lys Glu
            580                 585                 590

Arg Gln Lys Glu Leu Glu Gly Val Ala Asn Pro Ile Met Ser Lys Phe
        595                 600                 605

Tyr Gly Ala Ala Gly Gly Ala Pro Gly Ala Gly Pro Val Pro Gly Ala
    610                 615                 620

Gly Ala Gly Pro Thr Gly Ala Pro Asp Asn Gly Pro Thr Val Glu Glu
```

```
                625                 630                 635                 640

Val Asp

<210> SEQ ID NO 45
<211> LENGTH: 148
<212> TYPE: PRT
<213> ORGANISM: Saccharomyces cerevisiae

<400> SEQUENCE: 45

Met Leu Ser Asn Ala Lys Leu Leu Ser Leu Ala Met Ala Ser Thr
1               5                   10                  15

Ala Leu Gly Leu Val Ser Asn Ser Ser Ser Val Ile Val Val Pro
                20                  25                  30

Ser Ser Asp Ala Thr Ile Ala Gly Asn Asp Thr Ala Thr Pro Ala Pro
            35                  40                  45

Glu Pro Ser Ser Ala Ala Pro Ile Phe Tyr Asn Ser Thr Ala Thr Ala
        50                  55                  60

Thr Gln Tyr Glu Val Val Ser Glu Phe Thr Thr Tyr Cys Pro Glu Pro
65                  70                  75                  80

Thr Thr Phe Val Thr Asn Gly Ala Thr Phe Thr Val Thr Ala Pro Thr
                85                  90                  95

Thr Leu Thr Ile Thr Asn Cys Pro Cys Thr Ile Glu Lys Pro Thr Ser
                100                 105                 110

Glu Thr Ser Val Ser Ser Thr His Asp Val Glu Thr Asn Ser Asn Ala
            115                 120                 125

Ala Asn Ala Arg Ala Ile Pro Gly Ala Leu Gly Leu Ala Gly Ala Val
        130                 135                 140

Met Met Leu Leu
145

<210> SEQ ID NO 46
<211> LENGTH: 393
<212> TYPE: PRT
<213> ORGANISM: Saccharomyces cerevisiae

<400> SEQUENCE: 46

Met Ser Ser Arg Ile Ile Val Gly Ser Ala Ala Leu Ala Ala Ala Ile
1               5                   10                  15

Thr Ala Ser Ile Met Val Arg Glu Gln Lys Ala Lys Gly Gln Arg Arg
                20                  25                  30

Glu Gly Asn Val Ser Ala Tyr Tyr Asn Gly Gln Glu Tyr Gly Ser Ser
            35                  40                  45

Ala Pro Pro Gln Leu Gly Lys Leu His Asn Ile Lys Gln Gly Ile Lys
        50                  55                  60

Glu Asp Ala Leu Ser Leu Lys Asp Ala Leu Leu Gly Val Ser Gln Lys
65                  70                  75                  80

Ala Arg Glu Glu Ala Pro Lys Val Thr Lys Arg Val Ile Ser Pro Glu
                85                  90                  95

Glu Asp Ala Gln Thr Arg Lys Gln Leu Gly Gln Lys Ala Lys Asp Ser
            100                 105                 110

Ser Ser Gln Ser Ile Phe Asn Trp Gly Phe Ser Glu Ala Glu Arg Arg
        115                 120                 125

Lys Ala Ile Ala Ile Gly Glu Phe Asp Thr Ala Lys Lys Arg Phe Glu
    130                 135                 140

Glu Ala Val Asp Arg Asn Glu Lys Glu Leu Leu Ser Thr Val Met Arg
145                 150                 155                 160
```

```
Glu Lys Lys Ala Ala Leu Asp Arg Ala Ser Ile Glu Tyr Glu Arg Tyr
            165                 170                 175

Gly Arg Ala Arg Asp Phe Asn Glu Leu Ser Asp Lys Leu Asp Gln Gln
                180                 185                 190

Glu Arg Asn Ser Asn Pro Leu Lys Arg Leu Leu Lys Asn Asn Thr Gly
            195                 200                 205

Asp Ala Asn Thr Glu Glu Ala Ala Arg Ser Val Gln Gly Trp Gly
            210                 215                 220

Asp Thr Ala Gln Glu Phe Gly Arg Glu Glu Leu Glu Glu Ala Lys Arg
225                 230                 235                 240

Asn Ala Ser Ser Glu Pro Ser Glu Ala Gln Lys Arg Leu Asp Glu Leu
            245                 250                 255

Lys Lys Ile Lys Glu Lys Gly Trp Phe Gly Tyr Asn Lys Gly Glu Gln
            260                 265                 270

Ser Glu Gln Gln Ile Ala Glu Arg Val Ala Arg Gly Leu Glu Gly Trp
            275                 280                 285

Gly Glu Thr Ala Ala Gln Leu Ser Lys Asp Glu Met Asp Asp Leu Arg
    290                 295                 300

Trp Asn Tyr Glu Asn Ser Lys Lys Gln Leu Asp Lys Asn Val Ser Asp
305                 310                 315                 320

Ala Met Asp Ser Leu Ser Lys Ala Lys Glu Asp Leu Lys Gln Tyr Gly
            325                 330                 335

Ser His Trp Trp Ser Gly Trp Thr Ser Lys Val Asp Asn Asp Lys Gln
            340                 345                 350

Ala Leu Lys Asp Glu Ala Gln Lys Lys Tyr Asp Glu Ala Leu Lys Lys
            355                 360                 365

Tyr Asp Glu Ala Lys Asn Lys Phe Lys Glu Trp Asn Asp Lys Gly Asp
    370                 375                 380

Gly Lys Phe Trp Ser Ser Lys Lys Asp
385                 390
```

ETHANOL-RESISTANT YEAST GENE, AND USE THEREOF

CROSS-REFERENCE TO RELATED APPLICATIONS

This application is the U.S. national stage filing under 35 U.S.C. §371 of international application PCT/KR2010/008340, filed Nov. 24, 2010, which claims priority from Korean Patent Applications 10-2010-0037818, filed Apr. 23, 2010, 10-2010-0101765, filed Oct. 19, 2010, 10-2010-0101739, filed Oct. 19, 2010, and 10-2010-0117208, filed Nov. 24, 2010.

BACKGROUND OF THE INVENTION

1. Field of the Invention

The present invention relates to an ethanol-tolerant yeast strain and uses thereof.

2. Description of the Related Art

Bioethanol production from plant or seaweed biomass has become the focus of world-wide concern with the long-term availability and deleterious environmental aspects of fossil fuels (Jeffries, T., and P. Lindbladm, 2009; Ragauskas, A. J., et al., 2006; Rubin, E. M., 2008). However, as one concern, the relatively high production cost of bioethanol has hindered investment in related industries. Much effort has been made to lower the costs of biomass procuration, pretreatment, fermentation, and product recovery (Xu, Q., A. Singh, and M. E. Himmel, 2009). During ethanol production, ethanol-producing microorganisms confront multiple stresses such as high initial substrate concentration, increased ethanol concentration, and accumulation of toxic byproducts. In addition to rapid growth and efficient fermentation capacity, the ability to tolerate these stresses is an important factor in choosing an ethanol producer (Ding, J., et al, 2009; Gibson, B. R., et al., 2007; Yoshikawa, K., et al., 2009). One way to improve ethanol yield is to obtain strains with enhanced stress tolerance.

Although not perfect, the yeast *Saccharomyces cerevisiae* has been diversely used as a primary microorganism for producing ethanol from biomass sources on an industrial scale. This organism is always exposed on various environmental stresses such as high-concentrated ethanol generated from an industrial ethanol fermentation process, leading to reduction of cell growth, cell viability and ethanol production (Casey and Ingledew, 1986). In this connection, there has been demanded the development of yeast strains to overcome stresses caused by high ethanol concentration. Furthermore, genome-wide analyses such as microarray and global expression pattern analysis have been utilized for identification of novel genes related to ethanol stress (Hirasawa, et al., 2007; Teixeira, et al., 2009; Yoshikawa, et al., 2009). Using these approaches, a variety of ethanol-tolerant genes have been identified as a non-essential gene. In addition, the results of previous reports in view of ethanol tolerance have been inconsistent with each other due to diverse strains and growth conditions (Teixeira, et al., 2009). Accordingly, it could be appreciated that a strain produced from the aforementioned genetic information is not always tolerant to ethanol stress condition (Yoshikawa, et al., 2009). Meanwhile, a deletion mutation library of commercially accessible *Saccharomyces cerevisiae* has been utilized for a genome-wide screening of ethanol-tolerant genes (Fujita, et al., 2006; Teixeira, et al., 2009; Yoshikawa, et al., 2009). Principally, previous studies isolated ethanol-sensitive mutants and genes thereof, followed by demonstrating a corresponding gene to be a gene for growth under high ethanol concentration condition.

In general, diverse genes have been known to affect cellular phenotypes (for example, severity of diseases, overexpression of metabolites, etc.) in a serious manner. Unfortunately, most cellular and metabolic engineering approaches have been performed by deletion or overexpression of single gene because of experimental limitations of vector construction and transformation efficiency. As a result, there have been excluded researches using mutations of several genes.

To investigate a mechanism to ethanol tolerance, numerous studies have been carried out. Especially, unsaturated fatty acid related to membrane fluidity was reported to be a critical factor of ethanol tolerance in yeasts (Kajiwara, et al., 2000; You, et al, 2003).

In addition, it has been reported that the accumulation of trehalose (Kim, et al., 1996) or proline (Takagi, et al., 2005) improves ethanol tolerance in yeasts, ergosterol is closely associated with ethanol tolerance of *Saccharomyces cerevisiae* (Inoue, et al., 2000).

In the mean time, VGH fermentation process has been generally utilized to obtain enormous amounts of ethanol during short fermentation, and has advantages as follows: (a) reduction of process steps; and (b) time and cost reduction. However, fermentation time was increased due to high glucose concentration, resulting in poor ethanol production. Consequently, the tolerance against both high ethanol and high osmosis caused by high glucose concentration in yeast is necessary to use VGH fermentation process To develop ethanol-tolerant yeast strains, in addition to classic strategies such as evolutionary adaptation (Stanley, D., et al., 2010), random chemical mutagenesis (Mobini-Dehkordi, M., et al., 2008), and gene shuffling (Hou, L., 2010), three different approaches have recently been used: genome-wide DNA microarray analysis (Hirasawa, T., et al., 2007), transposon-mediated deletion mutant library (Takahashi, T., et al., 2001), screening of single gene knockout (SGKO) libraries (Auesukaree, C., et al., 2009; Fujita, K., et al., 2006; Kubota, S., et al., 2004; Teixeira, M. C., et al., 2009; van Voorst, F., et al., 2006; Yoshikawa, K., et al., 2009), and global transcriptional machinery engineering (gTME; Alper, H., et al., 2006). In the case of DNA microarrays, up- or down-regulated genes induced by ethanol stress are first identified as target genes and then their capability to confer ethanol tolerance is verified by overexpression for up-regulated genes or deletion for down-regulated genes. In the case of SGKO library screening, clones showing either diminished or enhanced growth are first isolated from screening in the presence of ethanol. Genes whose deletions cause slow growth are actually related with ethanol sensitivity and, therefore, should be verified for association with ethanol tolerance by overexpression. In contrast, genes whose deletions cause enhanced growth can directly used to construct ethanol-tolerant strains. However, the issue with these two approaches is that a huge number of target genes have been identified, representing as much as 5-10% of genes encoded in the yeast genome. Identification of ethanol-sensitive genes helps to understand the molecular basis of ethanol tolerance, but does not ensure the construction of ethanol-tolerant strains. Although it is easy and simple to prove whether overexpression of ethanol-sensitive genes confers ethanol resistance, few successful examples have been documented (Gibson, B. R., et al., 2007).

gTME reprograms the global transcriptional profile through random mutagenesis of one or more general transcriptional factors. This approach was first used to create a strain with enhanced ethanol tolerance by generating mutations of TATA-binding protein (TBP) encoded by SPT15, which could grow at a formerly lethal ethanol concentration (Alper, H., et al., 2006). However, other authors reported that this enhanced ethanol tolerance was not reproduced on a rich medium (Baerends, R. J., et al., 2009), which is not optional for industrial applications. Nevertheless, SPT15 mutations alter the transcription profile, presumably through the interaction with Spt3p, a subunit of the Spt-Ada-Gcn5-acetyltransferase (SAGA) complex that regulates a number of RNA polymerase II-dependent genes. In addition, SPT15 mutations have been identified that were pleiotrophic (Eisenmann, D. M., et al., 1989) and some mutations in the regulatory domain of SPT15 resulted in transcriptional increase (Cang, Y., et al., 1999). These observations indicate that different mutations of SPT15 may induce expression of different sets of genes.

In this study, gTME was exploited as previously reported (Alper, H., et al., 2006) to create S. cerevisiae strains with ethanol tolerance. The present inventors obtained five ethanol tolerant strains (ETSs) containing different SPT15 mutant alleles and examined the effect of SPT15 mutations on ethanol tolerance. A genome-wide microarray was performed to identify genes related with ethanol tolerance and their functions were further examined using deletion mutants.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventors have made intensive studies to develop an ethanol-tolerant yeast strain. As results, we have prepared a mutated SPT15 gene using a PCR-mediated random mutagenesis method, and an ethanol-tolerant yeast strain transformed with the mutated SPT15 gene. Afterwards, we have discovered that the yeast strain may grow under the conditions with high glucose or sucrose concentration (for example, 20%, 30% or 40%) as well as with high ethanol concentration (for example, 15% ethanol), and have isolated 18 genes related to ethanol tolerance by performing a transcriptome profiling in the yeast transformed with the mutated SPT15 gene and an ethanol-tolerant yeast strain transformed with the 18 genes, which may grow under the condition with high ethanol concentration (for example, 6-12% ethanol).

Accordingly, it is an object of this invention to provide an ethanol-tolerant yeast strain and a gene thereof.

It is another object of this invention to provide an osmo-tolerant yeast strain and a gene thereof.

It is still another object of this invention to provide an ethanol-tolerant yeast strain.

It is further still another object of this invention to provide a method for ethanol production.

Other objects and advantages of the present invention will become apparent from the following detailed description together with the appended claims and drawings.

BRIEF DESCRIPTION OF THE DRAWINGS

FIG. 1 represents a spot assay showing enhanced ethanol tolerance of ETS1-5. Cells were grown to an $OD_{600}$ of 1.0 in the YSCD-Ura or YPD liquid media and 10-fold serially diluted. Aliquots (5 µl) were spotted onto YSCD-Ura or YPD plates containing appropriate concentrations of ethanol and incubated at 30° C. for 4-6 days. Control stains were constructed by transformation of a parental plasmid into L3262 (C-L3262) and BY4741 (C-BY4741). FIG. 1C is a spot assay of ETS2 and ETS3 on the YPD plate. FIG. 1D shows results that the parental plasmid and plasmids recovered from ETS2 and ETS3 were integrated into the genome of L3262, yielding iL3262, iETS2, and iETS3, respectively, and the spot assay was performed on the YSCD-Ura (top panel) and YPD plates (bottom panel).

FIG. 3C represents a result that microarray data were validated by semi-quantitative RT-PCR of Hsp30, Hsp42, and Hsp104. Numerals 1 and 2 indicate biologically independent duplicates.

FIG. 5 is a result measuring a fermentation capacity of ethanol tolerant strains of iETS2 and iETS3. Exponentially growing cells of control iL3262 (Δ) and two ethanol tolerant strains iETS2 (■), and iETS3 (●) were harvested and transferred to 100 ml of YPD30E6 [YP supplemented with 30% glucose and 6% (v/v) of ethanol]. The initial cell density was adjusted to 0.3 $OD_{600}$. Cells were cultured at 30° C. with shaking at 120 rpm. After samples were taken every 12 h, cell growths (A) and ethanol concentrations (B) were determined by measuring the cell density and by using HPLC, respectively. Experiments were done in triplicate.

FIG. 6 is a result measuring a growth rate of ETS3 under conditions with different glucose concentrations. Osmo-tolerant strain, ETS3 (●) and control strain, Sc L3262 (□) were cultured at 30° C. with shaking at 12,000 rpm in YPD media containing diverse glucose (A) and sucrose (B) at diverse concentrations (20%, 30% and 40%, respectively). After samples were taken as indicated time, cell growth rate was determined by measuring cell density. Experiments was carried out in triplicate.

DETAILED DESCRIPTION OF THIS INVENTION

Figure 1A:
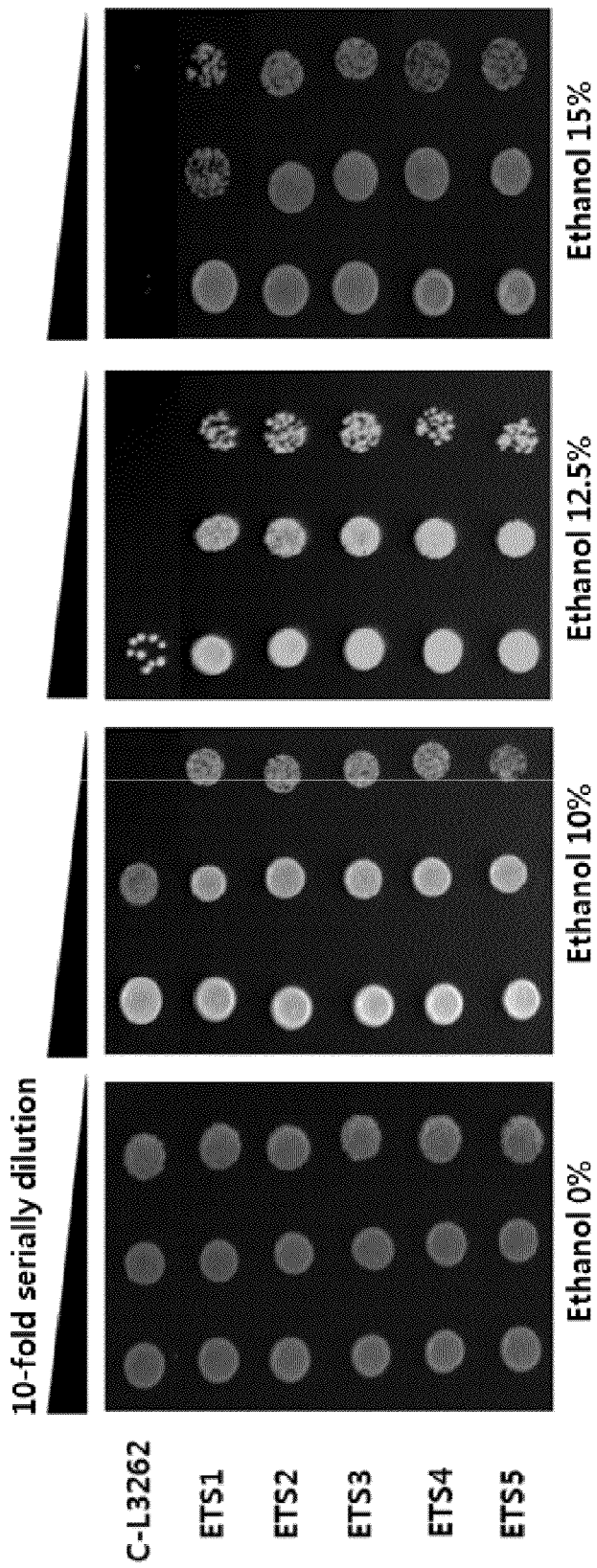
FIG. 1A represents a spot assay of ETS1-5 on the YSCD-Ura plate.

In one aspect of this invention, there is provided an ethanol-tolerant yeast strain transformed with a mutated SPT15 gene.

The present inventors have made intensive studies to develop an ethanol-tolerant yeast strain. As results, we have prepared a mutated SPT15 gene using a PCR-mediated random mutagenesis method, and an ethanol-tolerant yeast strain transformed with the mutated SPT15 gene. Afterwards, we have discovered that the yeast strain may grow under the conditions with high glucose or sucrose concentration (for example, 20%, 30% or 40%) as well as with high ethanol concentration (for example, 15% ethanol), and have isolated 18 genes related to ethanol tolerance by performing a transcriptome profiling in the yeast transformed with the mutated SPT15 gene and an ethanol-tolerant yeast strain transformed with the 18 genes, which may grow under the condition with high ethanol concentration (for example, 6-12% ethanol).

Ethanol as a volatile, flammable, colorless liquid is well-known to be the most-usable solvent. In addition to motor fuels and additives, ethanol has been industrially utilized as scents, flavorings, colorings and medicines. Also, ethanol has a sedative efficacy on central nervous system as a main mental component in an alcohol beverage. Ethanol may be produced not only by dehydration of ethylene in a petrochemical manner, but also by fermentation of sugars using yeasts in a biological manner. The biological method for ethanol production is much more economical than the petrochemical method in the senses that a petrochemical process depends on costs of petroleum and grain feed. Therefore, it has been urgently demanded to develop a yeast strain for ethanol production.

According to the present invention, the invention provides yeast strains transformed with a mutated SPT15 gene using PCR.

According to a preferable embodiment, the mutated SPT15 gene includes an amino acid sequence mutated in the amino acid sequence of wild-type SPT15 gene, more preferably an amino acid sequence mutated in a range of from three to five amino acids in the amino acid sequence of wild-type SPT15 gene, and most preferably, an amino acid sequence consisting of SEQ ID NOs:6-10.

According to a preferable embodiment, the mutated SPT15 gene includes: an amino acid sequence mutated at position K201, G216 and Q225; an amino acid sequence mutated at position L76 and L175; an amino acid sequence mutated at position S42, C78, S163 and I212; an amino acid sequence mutated at position F10 and M197; or an amino acid sequence mutated at position W26 and G192 in the amino acid sequence of wild-type SPT15 gene.

According to more preferable embodiment, the mutated SPT15 gene comprises: an amino acid sequence which the amino acid sequence at position K201, G216 and Q225 is mutated to the amino acid sequence at position K201Q, G216S and Q225 stop in the amino acid sequence of wild-type SPT15 gene (SEQ ID NO:6); an amino acid sequence at position L76 and L175 is mutated to the amino acid sequence at position L76V and L175S in the amino acid sequence of wild-type SPT15 gene (SEQ ID NO:7); an amino acid sequence at position S42, C78, S163 and I212 is mutated to the amino acid sequence at position S42N, C78R, S163P and I212 N in the amino acid sequence of wild-type SPT15 gene (SEQ ID NO:8); an amino acid sequence at position F10 and M197 is mutated to the amino acid sequence at position F10S and M197K in the amino acid sequence of wild-type SPT15 gene (SEQ ID NO:9); or an amino acid sequence at position K15, W26 and G192 is mutated to the amino acid sequence at position K15T, W26C and G192D in the amino acid sequence of wild-type SPT15 gene (SEQ ID NO:10).

According to the present invention, yeast strains transformed with the mutated SPT15 gene (preferably the mutated SPT15 gene consisting of SEQ ID NOs:1-5), may growth under the conditions of high-concentration ethanol, more preferably 5-15% ethanol, much more preferably 10-15% ethanol, and most preferably, 12.5-15% ethanol.

According to a preferable embodiment, the mutated SPT15 gene may be introduced into a yeast cell using a plasmid. According to a preferable embodiment, the mutated SPT15 gene may be introduced into a genomic DNA of a yeast cell.

According to a preferable embodiment, the yeast strain capable of being utilizing for transformation of the mutated SPT15 gene includes, but is not limited to, *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp. or an industrial polyploid yeast strain. More preferably, the yeast strain capable of being utilizing for transformation of the mutated SPT15 gene includes *Saccharomyces* spp., much more preferably *Saccharomyces cerevisiae*, and most preferably, *Saccharomyces cerevisiae* L3262.

In another aspect of this invention, there is provided an ethanol-tolerant yeast strain transformed with a mutated SPT15 gene.

Since the present yeast strains comprise the mutated SPT15 gene of this invention as active ingredients described above, the common descriptions between them are omitted in order to avoid undue redundancy leading to the complexity of this specification.

According to the present invention, the invention provides osmo-tolerant yeast strains transformed with a mutated SPT15 gene using PCR.

According to a preferable embodiment, the mutated SPT15 gene includes an amino acid sequence mutated at position S42, C78, S163 and I212 in the amino acid sequence of wild-type SPT15 gene.

According to more preferable embodiment, the mutated SPT15 gene includes an amino acid sequence which the amino acid sequence at position S42, C78, S163 and I212 is mutated to the amino acid sequence at position S42N, C78R, S163P 및 I212 N in the amino acid sequence of wild-type SPT15 gene (SEQ ID NO:8).

According to the present invention, the yeast strain of this invention transformed with the mutated SPT15 gene, preferably the mutated SPT15 gene of SEQ ID NO:8, may grow under the conditions containing glucose or sucrose of high-concentration, more preferably 20-50% concentration, much more preferably 30-40% concentration, and most preferably, 40% concentration.

According to a preferable embodiment, the yeast strain of this invention may grow under a culture condition with high-concentration ethanol, more preferably 5-15% ethanol, much more preferably 10-15% ethanol, and most preferably, 12.5-15% ethanol.

In still another aspect of this invention, there is provided an ethanol-tolerant yeast strain overexpressed with at least one nucleotide sequence selected from the group consisting of ALD3 (YMR169C), USV1 (YPL230W), FMP16 (YDR070C), RGI1 (YER067W), BTN2 (YGR142W), RTC3 (YHR087W), HSP30 (YCR021C), CTT1 (YGR088W), AIM17 (YHL021C), STF2 (YGR008C), GPH1 (YPR160W), YFR017C, SOL4 (YGR248W), PHM8 (YER037W), HSP12 (YFL014W), SSA4 (YER103W), SPI1 (YER150W) and OM45 (YIL136W).

According to the present invention, the present inventors have isolated/identified a novel gene associated with ethanol resistance through a transcriptome profile using an ethanol-tolerant yeast strain, and demonstrated that the ethanol-tolerant yeast strain transformed with the novel gene has ethanol resistance.

In this invention, the transcriptome profiling may be carried out in the ethanol-tolerant yeast strain.

In detail, a gene related with ethanol resistance may be identified through the steps of (i) performing a transcriptome profiling from a transformed yeast strain and a non-transformed (normal) yeast strain; and (ii) comparing/analyzing the transcriptome profiling, leading to massive identification of a yeast gene associated with ethanol tolerance and/or sensitivity.

In comparison/analysis of the transcriptome profiling, where the hybridization signal in the transformed yeast strain is detected above 2-fold increase than that in the normal yeast strain, the corresponding gene is determined as a gene up-regulating ethanol tolerance and where the hybridization signal in the transformed yeast strain is detected above 2-fold decrease than that in the normal yeast strain, the corresponding gene is determined as a gene down-regulating ethanol tolerance.

Since the present method comprises the yeast strains transformed with the mutated SPT15 gene of this invention as active ingredients described above, the common descriptions between them are omitted in order to avoid undue redundancy leading to the complexity of this specification.

According to a preferable embodiment, the transcriptome profiling may be carried out using a microarray.

In microarray, the present probes serve as a hybridizable array element and are immobilized on a substrate. A preferable substrate includes suitable solid or semi-solid supporters, such as membrane, filter, chip, slide, wafer, fiber, magnetic or non-magnetic bead, gel, tubing, plate, macromolecule, microparticle and capillary tube. The hybridizable array elements are arranged and immobilized on the substrate. Such immobilization occurs through chemical binding or covalent binding such as UV. In an embodiment of this invention, the hybridizable array elements may be bound to a glass surface modified to contain epoxy compound or aldehyde group or to a polylysin-coated surface using UV. Further, the hybridizable array elements are bound to a substrate through linkers (e.g., ethylene glycol oligomer and diamine).

The term "probe" used herein refers to a linear oligomer of natural or modified monomers or linkages, including deoxyribonucleotides, ribonucleotides and the like, which is capable of specifically hybridizing with a target nucleotide sequence, whether occurring naturally or produced synthetically. The probe used in the present method may be prepared in the form of preferably single-stranded and oligodeoxyribonucleotide probe. The present probe may contain naturally occurring dNMP (that is, dAMP, dGMP, dCMP and dTMP), nucleotide analogues or derivatives. In addition, the present probe may contain ribonucleotide. For example, the probe of this invention may include backbone-modified nucleotides such as peptide nucleic acid (PNA; M. Egholm et al., *Nature*, 365:566-568 (1993)), phosphorothioate DNA, phosphorodithioate DNA, phosphoroamidate DNA, amide-linked DNA, MMI-linked DNA, 2'-O-methyl RNA, alpha-DNA and methylphosphonate DNA, sugar-modified nucleotide such as 2'-O-methyl RNA, 2'-fluoro RNA, 2'-amino RNA, 2'-O-alkyl DNA, 2'-O-allryl DNA, 2'-O-alkynyl DNA, hexose DNA, pyranosyl RNA and anhydrohexitol DNA, and base-modified nucleotides such as C-5 substituted pyrimidine (substitution group contains fluoro-, bromo-, chloro-, iodo-, methyl-, ethyl-, vinyl-, formyl-, ethithyl-, propynyl-, alkynyl-, thiazolyl-, imidazolyl-, pyridyl-, etc.), 7-deazapurine with C-7 substitution (substitution group contains fluoro-, bromo-, chloro-, iodo-, methyl-, ethyl-, vinyl-, formyl-, alkynyl-, alkenyl-, thiazolyl-, imidazolyl-, pyridyl-, etc.), inosine and diaminopurine.

DNAs to be examined with a microarray of this invention may be labeled, and hybridized with array elements on microarray. Various hybridization conditions are applicable, and for the detection and analysis of the extent of hybridization, various methods are available depending on labels used. According to a preferable embodiment, the DNA is synthesized by incorporating aminoallyl-dUTP and is labeled with ester Cy dye, but is not limited to.

The nucleic acid sample to be analyzed may be prepared using mRNA from various biosamples. Preferably, the biosample is yeast cells and most preferably, the yeast cells of the present invention. Instead of probes, cDNA of interest may be labeled for hyribridization-based analysis.

Probes are hybridized with cDNA molecules. Suitable hybridization conditions may be routinely determined by optimization procedures. To establish a protocol for use of laboratory, these procedures may be carried out by various methods known to those ordinarily skilled in the art. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999). For example, the high stringent condition includes hybridization in 0.5 M $NaHPO_4$, 7% SDS (sodium dodecyl sulfate) and 1 mM EDTA at 65° C. and washing in 0.1×SSC (standard saline citrate)/0.1% SDS at 68° C. Also, the high stringent condition includes washing in 6×SSC/0.05% sodium pyrophosphate at 48° C. The low stringent condition includes e.g., washing in 0.2×SSC/0.1% SDS at 42° C.

Labels linking to the nucleic acid biosamples or probes may generate a signal to detect hybridization and be bound to oligonucleotide. Suitable labels include fluorophores ((e.g., fluorescein), phycoerythrin, rhodamine, lissamine, Cy3 and Cy5 (Pharmacia)), chromophores, chemiluminescers, magnetic particles, radioisotopes (e.g., $P^{32}$ and $S^{35}$), mass labels, electron dense particles, enzymes (e.g., alkaline phosphatase or horseradish peroxidase), cofactors, substrates for enzymes, heavy metals (e.g., gold), and haptens having specific binding partners, e.g., an antibody, streptavidin, biotin, digoxigenin and chelating group, but not limited to. Labeling is performed according to various methods known in the art, such as nick translation method, random priming method (Multiprime DNA labeling systems booklet, "Amersham" (1989)) and kination method (Maxam & Gilbert, *Methods in Enzymology*, 65: 499 (1986)). The labels generate signal detectable by fluorescence, radioactivity, measurement of color development, mass measurement, X-ray diffraction or absorption, magnetic force, enzymatic activity, mass analysis, binding affinity, high frequency hybridization or nanocrystal.

Following hybridization reactions, a hybridization signal indicative of the occurrence of hybridization is then measured. The hybridization signal may be analyzed by a variety of methods depending on labels linking to the nucleic acid biosamples or probes. For example, where probes are labeled with enzymes, the occurrence of hybridization may be detected by reacting substrates for enzymes with hybridization resultants. The enzyme/substrate pair useful in this invention includes, but is not limited to, a pair of peroxidase (e.g., horseradish peroxidase) and chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (tetramethylbenzidine), ABTS (2,2'-Azine-di[3-ethylbenz-thiazoline sulfonate]), o-phenylenediamine (OPD) and naphtol/pyronine; a pair of alkaline phosphatase and bromochloroindolylphosphate (BCIP), nitro blue tetrazolium (NBT), naphthol-AS-B1-phosphate and ECF substrate; and a pair of glucose oxidase and t-NBT (nitroblue tetrazolium) and m-PMS (phenzaine methosulfate). Where probes are labeled with gold particles, the occurrence of hybridization may be detected by silver staining method using silver nitrate. In these connections, where the present method for massively identifying a yeast gene related with ethanol tolerance and/or sensitivity is carried out by hybridization, it comprises the steps of: (i) hybridizing a nucleic acid sample derived from the transformed yeast strain of this invention as set forth and normal yeast strain to a substrate used in a microarray; and (ii) detecting the occurrence of hybridization. The signal intensity from hybridization is indicative of ethanol tolerance and/or sensitivity. In other words, when the hybridization signal to the nucleic acid of this invention from a sample to be diagnosed is detected above 1.5-fold increase than that in the normal sample (normal cell), the corresponding gene is determined as a gene up-regulating ethanol tolerance and where the hybridization signal is detected above 2-fold decrease, the corresponding gene is determined as a gene down-regulating ethanol tolerance.

According to a preferable embodiment, the ethanol-tolerant gene detected by the microarray includes ALD3 (YMR169C), USV1 (YPL230W), FMP16 (YDR070C), RGI1 (YER067W), BTN2 (YGR142W), RTC3 (YHR087W), HSP30 (YCR021C), CTT1 (YGR088W), AIM17 (YHL021C), 57F2(YGR008C), GPH1 (YPR160W), YFR017C, SOL4 (YGR248W), PHM8 (YER037W), HSP12 (YFL014W), SSA4 (YER103W), SPI1 (YER150W) and OM45 (YIL136W), but is not limited to.

According to a preferable embodiment, the ethanol-sensitive gene detected by the microarray includes RAX2 (YLR084C), BSC1 (YDL037C), PRM7 (YDL039C), VTS1 (YOR359W), RRN7 (YJL025W), VEL1 (YGL258W), YGR035C and YOR387C.

According to a preferable embodiment, yeast genes associated with ethanol tolerance and/or sensitivity gene detected by the microarray may be further confirmed by measuring their expression. The measurement of changes in gene expression may be carried out according to various methods known to those ordinarily skilled in the art, for example, using RT-PCR (Sambrook et al., *Molecular Cloning. A Laboratory Manual*, 3rd ed. Cold Spring Harbor Press (2001)), Northern blotting (Peter B. Kaufma et al., *Molecular and Cellular Methods in Biology and Medicine*, 102-108, CRC press) or in situ hybridization (Sambrook et al., *Molecular Cloning. A Laboratory Manual*, 3rd ed. Cold Spring Harbor Press (2001)).

According to RT-PCR protocol, total RNA is first extracted from the present transformed yeast cells and non-transformed normal yeast cells, and first cDNA is prepared using oligo-dT primer and reverse transcriptase. Then, PCR reaction is carried out using first cDNA as a template and an ethanol tolerant- and/or sensitive-specific primer set. The resulting products are separated by electrophoresis and the band patterns are analyzed and compared with the above-mentioned microarray data to measure the expression changes of ethanol-tolerant and/or -sensitive yeast genes.

In another aspect of this invention, there is provided a method for preparing a yeast strain with ethanol tolerance, comprising the step of introducing a copy of the mutated SPT15 gene into the yeast genome and/or mutating endogenous SPT15 gene in a genomic DNA of yeast cell.

In still another aspect of this invention, there is provided a method for preparing a yeast strain with ethanol tolerance, comprising the step of introducing a aforementioned nucleotide sequence (SEQ ID NOs:11-28) into the yeast genome and/or overexpressing the nucleotide sequence in a genomic DNA of yeast cell.

In further still another aspect of this invention, there is provided a method for ethanol production, comprising the step of culturing the yeast strain transformed with the mutated SPT15 gene in a medium containing one or more substrates capable of being metabolized to ethanol.

Since the present method comprises the yeast strains transformed with the mutated SPT15 gene or the above-mentioned nucleotide sequence (SEQ ID NOs:11-28) of this invention as active ingredients described above, the common descriptions between them are omitted in order to avoid undue redundancy leading to the complexity of this specification.

According to a preferable embodiment, the substrate capable of being metabolized to ethanol includes a C6 sugar. According to more preferable embodiment, C6 sugar is glucose, but is not limited to.

The present invention provides a cell transformed with a recombinant vector including the mutated SPT15 gene or the nucleotide sequence (SEQ ID NOs:11-28), or transfected with these transcripts, and a cell transformed by a gene introduction.

In addition, the present invention provides a transformant transformed with a recombinant vector including the mutated SPT15 gene or the nucleotide sequence (SEQ ID NOs:11-28), or a transformant transformed with the mutated SPT15 protein or a protein encoded by the nucleotide sequence.

The recombinant vector of the present invention includes a nucleotide sequence encoding an amino acid sequence of SEQ ID NOs:6-10 or SEQ ID NOs:29-46, or a complementary nucleotide sequence thereof. Typically, the vector of this invention may be constructed as cloning or expression vector. The vector of the present invention may be also constructed to utilize a prokaryotic or eukaryotic cell as a host. For example, a prokaryotic cell as a host includes bacteria and archeabacteria, and a eukaryotic cell includes a yeast cell, a mammalian cell, a plant cell, an insect cell, a stem cell and a fungal cell, and most preferably, a yeast cell.

Preferably, the recombinant vector of this invention includes: (i) a nucleotide sequence encoding an expression target of the present invention; and (ii) a promoter which is operatively linked to the nucleotide sequence of (i) and generates a RNA molecule in animal cells; and more preferably, (i) a nucleotide sequence of the present invention encoding SEQ ID NOs:6-10 or SEQ ID NOs:29-46, or a complementary nucleotide sequence thereof; (ii) a promoter which is operatively linked to the nucleotide sequence of (i) and generates a RNA molecule in animal cells; and (iii) 3'-untranslated region responsible of 3'-terminal polyadenylation of the RNA molecule.

Preferably, the expression target of the present invention includes, without limitation, a mutated SPT15 protein or a protein encoded by the nucleotide sequence, more preferably a mutated SPT15 protein consisting of SEQ ID NOs:6-10, or a protein consisting of SEQ ID NOs:29-46.

The term "promoter" as used herein means a DNA sequence regulating expression of an encoding sequence or functional RNA. The expression target-encoding nucleotide sequence is operatively lined to the promoter in the recombinant vector of this invention. The term "operatively linked" refers to functional linkage between a nucleic acid expression regulatory sequence (such as a promoter, signal sequence, or array of transcription factor binding sites) and a second nucleic acid sequence, wherein the expression regulatory sequence affects transcription and/or translation of the nucleic acid corresponding to the second sequence.

For example, the present vector which is expression vector and utilizes a prokaryotic cell as a host commonly includes a strong promoter (e.g., tac promoter, lac promoter, lacUV5 promoter, lpp promoter, $p_L^\lambda$ promoter, $p_R^\lambda$ promoter, rac5 promoter, amp promoter, recA promoter, SP6 promoter, trp promoter and T7 promoter, etc.) for transcription, a ribosome-binding site for translation, and transcription/translation termination sequence. More preferably, the host cell used in the present invention includes *E. coli*, and most preferably, *E. coli* DH5α. In addition, the promoter and operator region of *E. coli* tryptophan biosynthesis pathway (Yanofsky, C., *J. Bacteria*, 158:1018-1024 (1984)), and $p_L^\lambda$ promoter (Herskowitz, I. and Hagen, D., *Ann. Rev Genet.*, 14:399-445 (1980)) may be used as a regulatory region in *E. coli* utilized as a host. In *E. coli* as a host cell, Meanwhile, the vector capable of being used in the present invention may be prepared by manipulating a plasmid (example: pRS316, pSC101, ColE1, pBR322, pUC8/9, pHC79, pUC19, pET, etc.), a phage (example: λgt4.λB, λ-Charon, λΔz1, M13, etc.) or a virus (example: SV40, etc.) known to those ordinarily skilled in the art.

In each a vector of this invention and an eukaryotic cell (preferably, yeast cell) used as an expression vector and the host cell, a promoter that may regulate an expression target of this invention includes a promoter derived from a yeast cell, a mammalian virus and a genome of a mammalian cell, for example, but not limitation to, *S. cerevisiae* GAPDH (Glyceraldehyde 3-phosphate dehydrogenase) promoter, *S. cerevisiae* GAL1 to GAL10 promoter, *Pichia pastoris* AOX1 or AOX2 promoter, CMV (cytomegalo virus) promoter, adenovirus late promoter, vaccinia virus 7.5K promoter, SV40 promoter, HSV tk promoter, RSV (Rous sarcoma virus) promoter, EF1 alpha promoter, metallothionein promoter, beta-actin promoter, human IL-2 gene promoter, human IFN gene promoter, human IL-4 gene promoter, human lymphotoxin gene promoter and human GM-CSF gene promoter. Most preferably, the promoter is *S. cerevisiae* GAPDH promoter.

Preferably, the expression construct utilized in this invention includes a polyadenylation sequence (example: bovine growth hormone terminator and SV40-derived polyadenylation sequence).

The procedure to deliver the present vector into a host cell may be carried out according to various methods known to those ordinarily skilled in the art. For example, the transformation for a prokaryotic cell as a host may be performed using a $CaCl_2$ method (Cohen, S. N. et al., *Proc. Natl. Acac. Sci. USA*, 9: 2110-2114 (1973)), a Hanahan method (Cohen, S. N. et al., *Proc. Natl. Acac. Sci. USA*, 9: 2110-2114 (1973); and Hanahan, D., *J. Mol. Biol.*, 166: 557-580 (1983)) and an electroporation method (Dower, W. J. et al., *Nucleic. Acids Res.*, 16: 6127-6145 (1988)), and for an eukaryotic cell, using electroporation, lipofection, microinjection, particle bombardment, yeast spheroplast/cell fusion used in YAC, *Agrobacterium tumefaciens*-mediated transformation in plant cells.

According to a preferable embodiment, the expression target-encoding nucleotide sequence of this invention has a structure of "promoter-expression target-encoding nucleotide sequence-polyadenylation sequence".

The vector system of this invention may be constructed by various methods known to those skilled in the art and its practical method is described in Sambrook et al., Molecular Cloning, A Laboratory Manual, Cold Spring Harbor Laboratory Press (2001), which is herein incorporated by reference.

The preparation method of yeast cells transformed using the recombinant vector of this invention may be carried out by gene transfer methods, for example including electroporation, lithium acetate/DMSO method (Hill, J., et al., (1991), DMSO-enhanced whole cell yeast transformation. Nucleic Acids Res. 19, 5791.), liposome-mediated transfer method (Wong et al., 1980), retrovirus-mediated transfer method (Chen, et al., (1990), J. Reprod. Fert. 41:173-182; Kopchick, et al., (1991) Methods for the introduction of recombinant DNA into chicken embryos. In Transgenic Animals, ed. N. L. First & F. P. Haseltine, pp. 275-293, Boston; Butterworth-Heinemann; Lee, M.-R. and Shuman, R. (1990) Proc. 4th World Congr. Genet. Appl. Livestock Prod. 16, 107-110) and so forth.

In the mean time, a protein of interest may be effectively introduced into a cell to utilize the protein of interest of this invention as an active ingredient for gene transfer. For example, using the mutated SPT15 protein (SEQ ID NOs:6-10) or the aforementioned protein (SEQ ID NOs:29-46) as an active ingredient, it is preferable to fuse these protein with protein transduction domain (PTD). In other words, for permeable peptide transduction of the mutated SPT15 protein or the above-described protein into a cell, PTD is preferably fused with these proteins. PTD has a permeable function penetrating a protein fused with PTD across a cell membrane since it primarily contains basic amino acid residues such as lysine and arginine. Preferably, PTD includes HIV-1 Tat protein, *Drosophila antennapedia* homeodomain, HSV VP22 transcription regulatory protein, vFGF-induced MTS peptide, penetratin peptide, transportan or Pep-1 peptide-derived sequence, but is not limited to.

The features and advantages of the present invention will be summarized as follows:

(a) The present invention relates to a gene associated with ethanol tolerance, and yeast strains and uses using the same.

(b) The yeast strain of this invention may growth under the condition with high-concentration ethanol, preferably 6-15% ethanol.

(c) The yeast strain of this invention may growth under the condition in high osmotic pressure, preferably 30-40% glucose or sucrose.

(d) The present inventors developed yeast strains resistant to high-concentration glucose and ethanol, suggesting that they would be valuably applied to much effective ethanol production, and also be utilized as a superbacteria having tolerance to various stresses for ethanol production with high efficiency.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Yeast Strains and Growth Conditions

*S. cerevisiae* L3262 (MAT-α; ura3-52 leu2-3,112 his4-34; KRIBB, Dae-jeon, Republic of Korea) and BY4741 (MATa his3Δ1 leu2Δ0 met15Δ0 ura3Δ0) were used as transformation recipients. The non-essential haploid *S. cerevisiae* deletion library was kindly obtained from Dr. Wonkee Hur (Seoul National University, Seoul, Korea) for the verification of identified genes. Unless otherwise mentioned, yeast cells were grown at 30° C. in YPD (1% Bacto yeast extract, 2% Bacto peptone, and 2 w/v % glucose and 15% bacto-agar for solid plates; Difco, MI) for non-selective propagation or yeast synthetic complete (YSCD) medium (0.67% yeast nitrogen base without amino acids, amino acid supplement mixture, 2% dextrose, and 1.5% noble agar for solid plates; MP, OH) for selective propagation. To construct a plasmid, pRS316 (CE-based vector; Sc GAPDH promoter, URA3 selection marker; Ewha University, Seoul, Republic of Korea) was used as an expression vector, and *E. coli* DH5α (Stratagene, CA) as a host cell were cultured at 37° C. in LB media ( ) supplemented with 100 mg/l ampicillin (Sigma-Aldrich, MO).

Molecular Methods

Plasmid preparation, cloning, and sequencing were performed as previously described (Sambrook, 2001). *Escherichia coli* strain DH5α was used as a host for plasmid preparation.

Reverse Transcription-Polymerase Chain Reaction (RT-PCR) and PCR

For RT, total RNA was prepared from exponentially growing cells. First strand cDNAs were synthesized by transcribing 2 µg of total RNAs with random hexamers and 200 U of M-MuLV reverse transcriptase (Promega, Madison, Wis., USA) as recommended by the manufacturer. Oligonucleotides used for PCR are listed in Table 1. The amplification conditions were 95° C. for 1 min, 55-60° C. for 1 min, and 72° C. for the appropriate period of time depending on the length of DNA to be amplified for 20 cycles for RT-PCT and 30 cycles for regular PCR. If necessary, PCR products were purified by gel elution, cloned into the pGEM-T easy vector (Promega), and sequenced (Bionics, Seoul).

SPT15 Mutant Library Construction

The entire open reading frame (ORF) of wild type SPT15 (SPT15 wt) was PCR-amplified from genomic DNA as a template with sense (5'-gtag ggatcctgagatggccgatgaggaacgtt-3', BamHI site underlined) and antisense (5'-gtaggaattctcacatttttctaaattcacttag-3', EcoRI site underlined) primers and cloned into the pGem T-easy vector, yielding pT-SPT15. The SPT15 mutant library was generated by using the GeneMorph II random mutagenesis kit (Stratagene, La Jolla, Calif., USA) with pT-SPT15 as template and using the aforementioned primers. PCR products were digested with BamHI and EcoRI, and cloned into a pRS316-derived plasmid, pRS316-GCYH2gR, in which cloned genes are placed under control of glyceraldehyde-3-phosphate dehydrogenase promoter ($TDH3_P$) and galactose-1-phosphate uridyl transferase terminator ($GAL7_T$). The resulting plasmids were transformed into *E. coli* DH5α and incubated at 30° C. to generate a primary library for SPT15 mutants with total colony number being $4 \times 10^6$. From the sequencing of 20 randomly selected colonies, the molecule-based mutation rate was determined to be 70%. Mutations were found at more than one site, mostly 3-5, in 14 colonies, with the remainder being the wild type. Following amplification and large-scale preparation, the library plasmids (500 µg) were transformed into *S. cerevisiae* L3262 and incubated at 25° C. on solid YSCD-Ura. The total number of yeast colonies was approximately $5 \times 10^6$ with a transformation efficiency of approximately $4 \times 10^6$ colony forming units (CFU)/µg DNA. All the colonies were harvested by scrubbing the surfaces of plates with 15 ml YSCD-Ura to prepare a yeast library for SPT15 mutants. After 4-fold propagation in cell number at 25° C., aliquots of the cell suspension were stored at −80° C. in the presence of 20% glycerol until used.

Yeast Transformation

All plasmids for yeast transformation were manually prepared without RNA digestion. The DNA concentration was roughly measured by comparing the band intensity with that of control DNA of known concentration. This mixture of DNAs and RNAs was used for yeast transformation as previously described (Hirasawa, et al., 2007).

Spot Assay

Aliquots (5 µl) of cells grown to an optical density at 600 nm ($OD_{600}$) of 1.0 were 10-fold serially diluted and spotted onto solid synthetic or rich media containing appropriate concentrations of ethanol. Plates were incubated at 30° C. for 4-6 days.

Ethanol Susceptibility Assay

Cells grown to $OD_{600}$ of 1.0 were harvested, equally divided into fresh YSCD-Ura media containing 12.5% and 15% ethanol (v/v), and incubated at 30° C. for 4-6 h. At appropriate time points, aliquots were properly diluted and plated onto solid YPD. Cell viability was measured as a function of time (h) and expressed as the relative number of CFU.

Genomic Integration

The mutated SPT15 gene was cloned into the integrating vector pRS406, linearized at the unique ApaI site within URA3, and transformed into *S. cerevisiae* L3262. The inset-free plasmid was treated in a similar way to create the control strain iL3262. Genomic integration was verified by PCR.

Transcriptome Profiling and Data Analysis

*S. cerevisiae* 30K oligo microarrays (MYcroarray, Ann Arbor, Mich., USA) were used for transcriptome profiling. Total RNA was prepared from exponentially growing cells and RNA quality control for microarray analysis was performed as described previously (Park, et al., 2007). cDNAs incorporated with aminoallyl-dUTP were synthesized from 40-50 µg of total RNA using an Aminoallyl post DNA Labeling kit (GeneChem, Daejeon, Korea) and a superscript reverse transcriptase (Invitrogen, Carlsbad, Calif., USA). The synthesized cDNA was labeled with NHS-ester Cy dyes and used for hybridization. Hybridized slides were washed by SSC buffer, and then scanned with a ScanArray 5000 scanner (Hewlett-Packard, Palo Alto, Calif., USA). Raw microarray data were analyzed by using ArrayNorm (genome.tugraz.at), a platform-independent Java tool for normalization and statistical analysis (Pieler, et al., 2004). Clustering for genes with the average change higher than 2-fold was carried out using Cluster 3.0 (rana.lbl.gov/EisenSoftware.htm). Enrichment of functional categories among differentially expressed genes was analyzed using the MIPS Functional Catalogue (mips.gsf.de). Specific gene functions were based on the *Saccharomyces* Genome Database (www.yeastgenome.org), and transcription factor biding sties were analyzed by YEATRACT (www.yeastact.com/index.php). To validate DNA microarray data, semi-quantitative reverse transcription PCR was performed as described previously (Oh, et al., 2004) with the RNA samples used for microarray experiments.

Fermentation

Exponentially growing cells were harvested and transferred to 100 ml of YPD30E6 [YP supplemented with 30% glucose and 6% (v/v) of ethanol]. The initial cell density was adjusted to 0.3 $OD_{600}$. Cells were cultured at 30° C. with shaking at 120 rpm. After samples were taken every 12 h, cell growths and ethanol concentrations were determined by measuring the cell density and by using high-pressure liquid chromatography (HPLC), respectively. The samples were loaded onto an Aminex HPX-87H column (Bio-Rad, Hercules, Calif., USA) which was set to 60° C. Glucose and ethanol were eluted with 0.5 mM $H_2SO_4$ at a flow rate of 0.6 ml/min. Peaks were detected by refractory index, identified by retention time, and quantified according to a standard curve. Cell growth was monitored by measuring the optical density at 600 nm.

Results

Identification of Ethanol-Tolerant Strains

To identify genes that conferred ethanol-tolerance by high-throughput screening, it is usually advantageous to use a strain with a low ethanol tolerance background. Since most ethanol sensitive among several S. cerevisiae laboratory strains tested (data not shown), L3262 was selected and used for constructing the yeast SPT15 mutant library. For screening of ethanol tolerant strains, an aliquot of the yeast library stock representing $5 \times 10^6$ CFU were spread on the solid YSCD-Ura medium supplemented with 12.5% or 15% ethanol. The plates were sealed to prevent ethanol evaporation and incubated at 30° C. Ten days after, nine and six colonies had developed in the presence of 12.5% and 15% ethanol, respectively. The ethanol tolerance of the 15 colonies was examined by a spot assay on the solid YSCD-Ura medium containing up to 15% ethanol. As a result, five ethanol tolerant strains (ETS; ETS1-5) were obtained. All five strains tolerated 15% ethanol on the synthetic medium, whereas the control did not tolerate ethanol concentrations exceeding 10% (FIG. 1A).

Figure 1B:
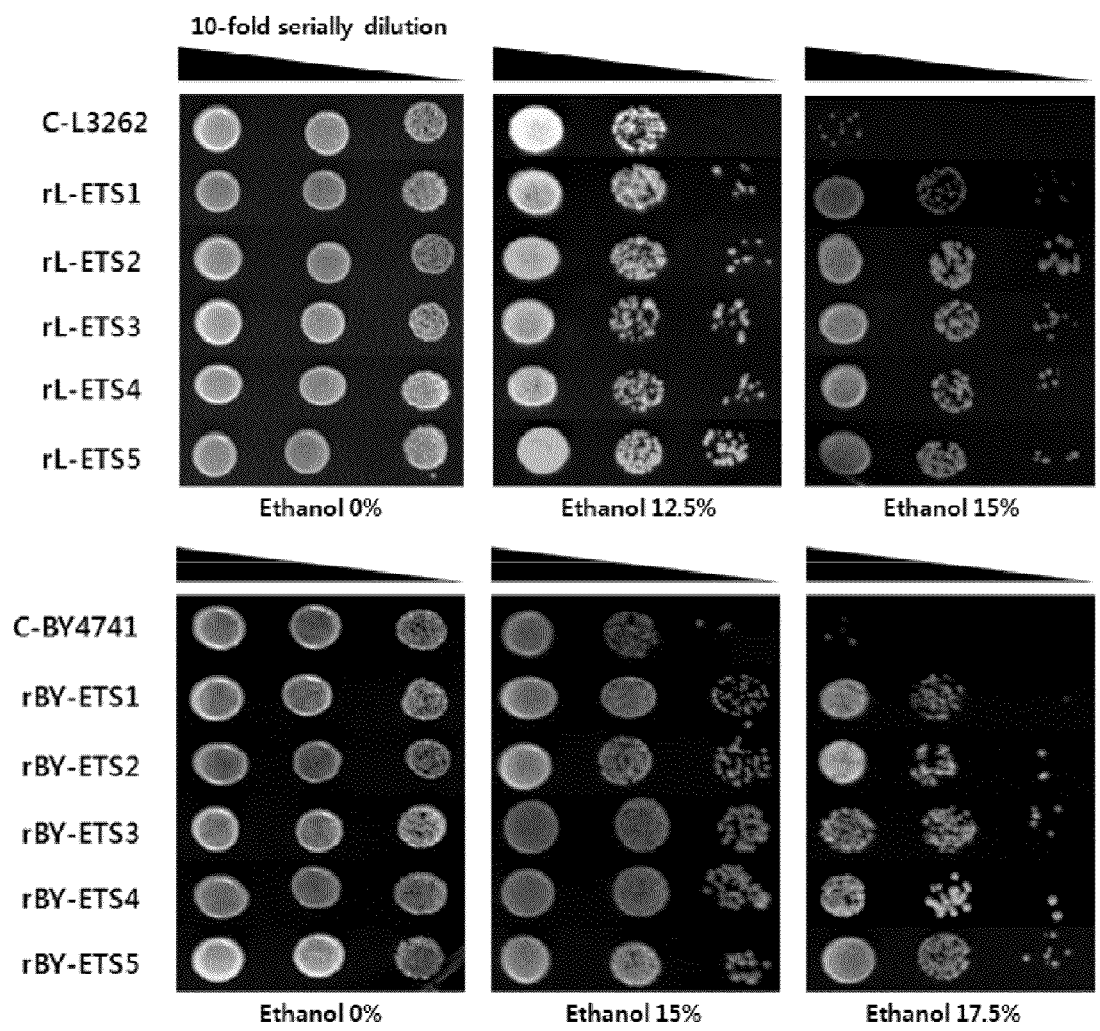
FIG. 1B shows results that plasmids recovered from ETS1-5 were re-transformed into L3262 and BY4741, yielding rL-ETS1-5 and rBY-ETS1-5, respectively, and spot assay was performed on the YSCD-Ura plate.

To confirm whether the enhanced ethanol tolerance was conferred by the presence of a mutated SPT15, plasmids were recovered from ETS1-5 (pSPT15-M1, -M2, -M3, -M4, and -M5, respectively after the mutated alleles of SPT15). These plasmids were individually re-introduced into L3262 and By4741 to yield rL-ETS1-5 and rBY-ETS1-5, respectively. To construct control strains, pRS316-GCYH2gR containing SPTwt was transformed into L3262 and BY4741, yielding C-L3262 and C-BY4741, respectively. When spot-assayed on a synthetic medium, rL-ETS1-5 showed the same degree of ethanol tolerance as ETS1-5 did (FIG. 1B, top panel). Meanwhile, rBY-ETS1-5 showed tolerance to as high as 17.5% ethanol (FIG. 1B, bottom panel). This was not surprising, since BY4741 originally displayed higher ethanol tolerance than L3262 (data not shown). Thus, the enhanced ethanol tolerance of ETS1-5 was suggested to be the effect of mutated SPT15.

Next, each plasmid was sequenced to reveal mutations. Table 1 lists mutated amino acids in each SPT15 allele: K201N, G216S, and N225Stop in SPT15-M1; L76V and L175S in SPT15-M2; S42N, C78R, S163P, and I212 N in SPT15-M3; F10S and M197K in SPT15-M4; K15T, W26C, and G192D in SPT15-M5.

TABLE 1

Point mutations of SPT15 alleles.

| Strain | SPT15 allele | amino acid replacement | Structural domain where the point mutation located[a] |
|---|---|---|---|
| ETS1 | SPT15-M1[b] | K201N, G216S, N225Stop | S3'-S4' loop, S5', H2' |
| ETS2 | SPT15-M2 | L76V, L175S | S1-H1 loop, H1' |
| ETS3 | SPT15-M3 | S42N, C78R, S163P, I212N | N-terminus, S1-H1 loop, S1', S5' |

TABLE 1-continued

Point mutations of SPT15 alleles.

| Strain | SPT15 allele | amino acid replacement | Structural domain where the point mutation located[a] |
|---|---|---|---|
| ETS4 | SPT15-M4 | F10S, M197K | N-terminus, S3'-S4' loop |
| ETS5 | SPT15-M5 | K15T, W26C, G192D | N-terminus, N-terminus, S3' |

[a]Structural domain nomenclature as described in Chasman et al. (1993). H, α-helix; S, β-sheet.
[b]Sixteen amino acids are deleted at the C-terminus due to N225Stop.

Notably, a silent mutation (N225Stop) in SPT15-M1 yielded a truncated version with 16 residues deleted at the C-terminus. As seen in Table 1, the point mutations scattered throughout the SPT15 ORF were not assigned to the structural domain associated with enhanced ethanol tolerance. Only SPT15-M2 had a mutation (L175S) at the domain interacting with Spt3p, which had earlier been implicated in the regulation of gene transcription. These data were consistent with the suggestion that the mutation of several subregions of Spt15p confers ethanol tolerance, presumably through the interaction with other components of the transcriptional machinery in addition to Spt3p.

According to the data of FIG. 1B, ETS1 was least tolerant, and ETS2 and ETS3 seemed to be slightly more (or equally at least) tolerant than ETS4 and ETS5. So, ETS2 and ETS3 were chosen for further experiments. S. cerevisiae laboratory strains used for expression of a certain gene usually have independent mutations in multiple genes encoding enzymes for amino acid biosynthesis and, therefore, require supplementation of specific amino acids for growth when cultured in a defined medium. It has been argued that low leucine supplementation, but not mutated SPT15, led to enhanced ethanol tolerance (Baerends, et al., 2009). More significantly, ethanol tolerance was abolished when cells were cultured in the YPD complex rich medium, which is not optional for industrial applications. Since ETS2 and ETS3 also require leucine and histidine supplementation for growth, the enhanced ethanol tolerance of these strains might not be due to mutations in SPT15. Appropriately, the ethanol tolerance of ETS2 and ETS3 was tested by a spot assay on YPD. As shown in FIG. 1C, ETS2 was sensitive to 15% ethanol, contrary to the data of FIG. 1A, whereas ETS3 displayed ethanol tolerance similar to that shown on the synthetic medium. However, C-L3262, which was extremely sensitive to 15% ethanol in the synthetic medium, seemed to gain some tolerance on YPD, suggesting that the basic level of ethanol tolerance in the rich medium might be higher than on the synthetic medium. The collective data were consistent with the conclusion that ETS3 is more tolerant to ethanol than ETS2 on YPD.

Figure 2:
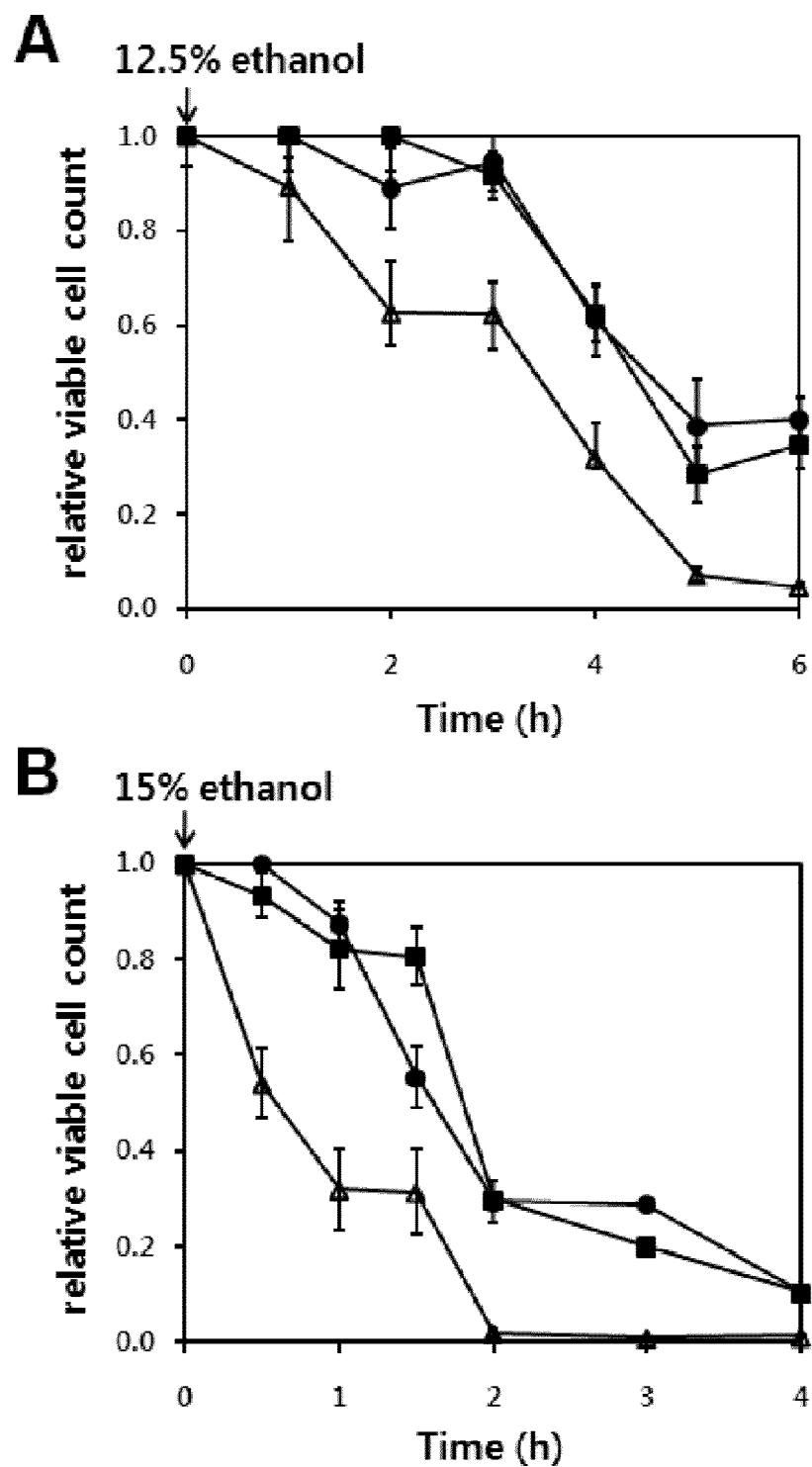
FIG. 2 is a result testing ethanol susceptibility of ETS3 and ETS3. Following ethanol shock for the indicated times, C-L3262, ETS2, and ETS3 were grown on the YSCD-Ura plate in the presence of 12.5% (A) and 15% (B) ethanol for 2 days. Relative viability was expressed as % control after counting the number of colony. C-L3262 (Δ), ETS2 (■), and ETS3 (●). Experiments were done in triplicate.

The cell-cell heterogeneity in expression is one of issues encountered when the information obtained from episomal overexpression in laboratory strains is scaled up to industrial applications. Heterogeneity is caused by the inability to control copy number in spite of the continual presence of selection pressure, which clearly is not optional for yeast culture on an industrial scale. Accordingly, stable expression and maintenance of the gene in the absence of selective pressure (i.e., integration into the chromosome) is frequently desirable. Here, we constructed strains in which SPT15-M2 and -M3 were integrated into the genome of L3262; the corresponding constructs were named iETS2 and iETS3, respectively. The control strain iL3262 were created with a plasmid containing SPT15 wt. FIG. 2 shows the spot assay of these three strains on YSCD (top panel) and YPD (bottom panel). The degrees of ethanol tolerance of both iETS2 and iETS3 on YSCD were similar to those of ETS2 and ETS3 on YPD (FIG. 1C), respectively. Again, both iETS2 and iETS3 on YPD were more tolerant than on YSCD, such that no difference between the two was observed even at an ethanol concentration of 15%.

To confirm the spot assay results, the susceptibility to 12.5% and 15% ethanol was examined. The survival rates of both strains were significantly improved compared to the control at both 12.5% and 15% ethanol (FIG. 2). At 12.5% ethanol, the time point showing 50% viability ($T_{50}$) was 4.5 h for ETS2 and ETS3, in contrast to 3.5 h for the control. A sharper contrast was observed at 15% ethanol, with a $T_{50}$ of 100 min for both ETS2 and ETS3, and 40 min for control. These data, together with spot assay data, demonstrated that ETS2 and ETS3 had enhanced ethanol tolerance conferred by SPT15 mutations.

Five strains with enhanced ethanol tolerance were obtained through SPT15 mutant library screening. Plasmids were recovered from these strains and re-transformed into the strain used for library construction (L3262) and another strain (BY4741). All these newly constructed strains also displayed enhanced ethanol tolerance on the defined media. Enhanced ethanol tolerance of ETS2 and ETS3 was sustained on the complex rich medium, ruling out the possibility that enhanced ethanol tolerance was conferred by activation of leucine uptake and/or utilization by a certain SPT15 mutant allele, as argued previously (Baerends, et al., 2009). Enhanced ethanol tolerance of ETS2 and ETS3 was confirmed by ethanol susceptibility following ethanol shock. Enhanced ethanol tolerance was further observed in two integrated strains, in which SPT15 mutant alleles derived from ETS2 and ETS3 were integrated into the L3262 genome.

Transcriptome Profile Analysis of Ethanol-Tolerant Mutant Strains

Figure 3:
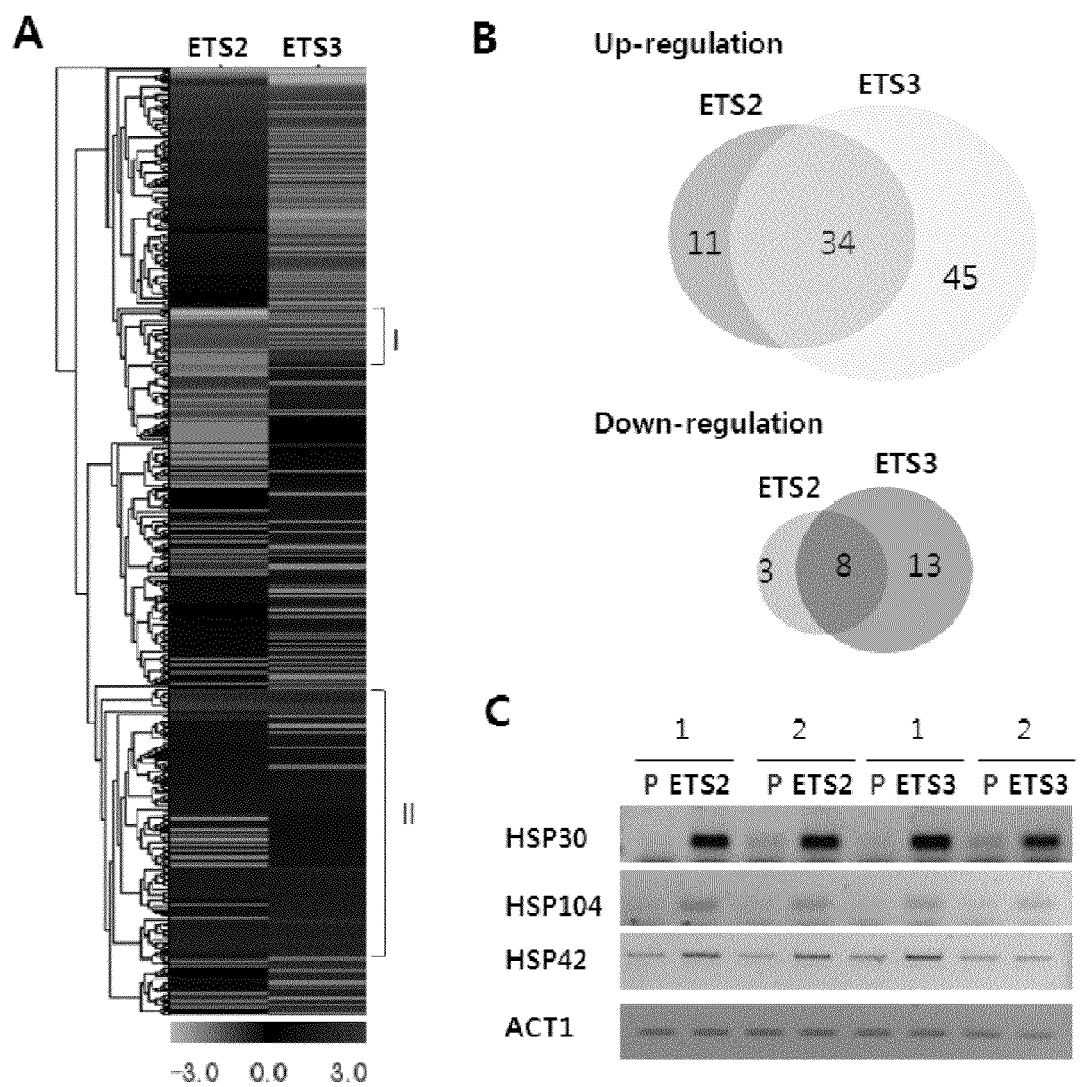
FIG. 3 shows a microarray data analysis of ETS2 and ETS3. Microarray analysis was performed with Poly(A)$^+$ RNAs prepared from C-L3262 (control), ETS2, and ETS3 grown to mid-log phase without ethanol stress challenge. Differentially expressed genes with expression fold change >2 were profiled for clustering (A) and Venn diagram (B).

We were interested in genes responsible for enhanced ethanol tolerance of ETS2 and ETS3, the expression levels of which were regulated by SPT15 mutations. To obtain this information, DNA microarrays for transcriptional profiling were conducted with total RNAs prepared from control C-L3262, ETS2, and ETS3 cells grown to early-log phase in YSCD-Ura. After performing microarray experiments in duplicate, expression fold changes were averaged. The raw data have been registered at Gene Expression Omnibus under the accession number GSE23965. Clustering of genes with fold change higher than 2 compared to control displayed differential expression patterns between ETS2 and ETS3, reflecting the effect of different mutations of SPT15 on the global transcription (FIG. 3A). In ETS2, 49 and 11 genes were up- and down-regulated, respectively, whereas in ETS3, 79 and 21 genes were up- and down-regulated, respectively (FIG. 3B). Thirty-four up-regulated and eight down-regulated genes were shared between ETS2 and ETS3 (FIG. 3B). To validate the microarray data, the actual expression levels of HSP30 and HSP42 over the cutoff value, and HSP104 below the cutoff value were examined by RT-PCR. According to the microarray data, HSP30, HSP42, and HSP104 were up-regulated by 5.7-, 4.3-, and 1.7-fold in ETS2 and 6.3-, 4.1-, and 1.8-fold in ETS3, respectively. The fold increases of those genes were consistent with the RT-PCR data (FIG. 3C).

Next, the commonly up- and down-regulated genes were categorized based on annotated function. The functions of the up-regulated genes included stress response and protein folding (n=11 genes); pentose-phosphate pathway, cell wall, and transport (n=2); metabolism of energy reserves and energy generation (n=1), and unclassified proteins (n=15) (Table 2 and Table 3).

TABLE 2

List of genes commonly up-regulated in ethanol tolerant strains ETS2 and ETS3 in the absence of ethanol stress.

| | Fold change ($Log_2$) | | | | | | | |
|---|---|---|---|---|---|---|---|---|
| | ETS2 | | ETS3 | | Msn4p/ | | | |
| Gene | Exp1 | Exp2 | Exp1 | Exp2 | Msn2p | Yap1p | Hsf1p | Hac1p |
| Stress Response and Protein Folding | | | | | | | | |
| APJ1 | 1.4 | 1.1 | 1.3 | 1.3 | 3 | 0 | 1 | 2 |
| ALD3 | 2.5 | 1.8 | 1.6 | 2.1 | 2 | 1 | 0 | 1 |
| CTT1 | 1.7 | 1.7 | 1.4 | 1.9 | 4 | 2 | 4 | 1 |
| HSP12 | 1.1 | 1.5 | 1.0 | 1.5 | 7 | 0 | 1 | 4 |
| HSP30 | 2.7 | 2.3 | 3.0 | 2.3 | 0 | 2 | 0 | 0 |
| HSP31 | 1.5 | 1.6 | 4.5 | 1.5 | 1 | 1 | 2 | 0 |
| HSP42 | 2.3 | 1.9 | 1.8 | 2.3 | 3 | 0 | 2 | 1 |
| SDP1 | 2.0 | 1.3 | 1.8 | 1.6 | 3 | 0 | 2 | 0 |
| SSA4 | 1.0 | 1.7 | 1.4 | 2.0 | 3 | 1 | 1 | 1 |
| TSL1 | 1.2 | 1.2 | 1.1 | 1.9 | 7 | 0 | 1 | 2 |
| YJL144W | 3.7 | 2.3 | 3.4 | 2.7 | 1 | 1 | 2 | 2 |
| Pentose-Phosphate Pathway | | | | | | | | |
| PGM2 | 1.7 | 1.2 | 1.7 | 2.1 | 7 | 1 | 0 | 1 |
| SOL4 | 1.9 | 1.5 | 1.6 | 1.9 | 1 | 0 | 6 | 0 |
| Cell Wall | | | | | | | | |
| SPI1 | 2.0 | 1.3 | 1.8 | 1.6 | 3 | 1 | 2 | 1 |
| OSW2 | 1.2 | 1.0 | 1.9 | 1.4 | 0 | 1 | 2 | 1 |
| Transport | | | | | | | | |
| PIC2 | 1.5 | 1.1 | 1.4 | 1.1 | 1 | 0 | 2 | 0 |
| BTN2 | 2.9 | 3.1 | 2.9 | 3.5 | 2 | 0 | 1 | 0 |
| Metabolism of Energy Reserves | | | | | | | | |
| GPH1 | 1.6 | 1.3 | 1.2 | 2.1 | 3 | 1 | 0 | 1 |
| Energy Generation | | | | | | | | |
| STF2 | 1.7 | 1.2 | 1.8 | 1.4 | 2 | 1 | 1 | 2 |

TABLE 2-continued

List of genes commonly up-regulated in ethanol tolerant strains ETS2 and ETS3 in the absence of ethanol stress.

| | Fold change (Log$_2$) | | | | | | | |
|---|---|---|---|---|---|---|---|---|
| | ETS2 | | ETS3 | | Msn4p/ | | | |
| Gene | Exp1 | Exp2 | Exp1 | Exp2 | Msn2p | Yap1p | Hsf1p | Hac1p |
| Unclassified Proteins | | | | | | | | |
| AIM17 | 2.4 | 1.0 | 1.8 | 1.9 | 3 | 0 | 2 | 2 |
| FMP16 | 1.2 | 1.3 | 1.0 | 1.6 | 1 | 1 | 0 | 0 |
| OM45 | 1.4 | 1.0 | 1.0 | 1.5 | 3 | 1 | 4 | 3 |
| PHM8 | 1.5 | 1.6 | 1.6 | 1.0 | 4 | 0 | 2 | 0 |
| RTC3 | 2.4 | 2.1 | 2.1 | 1.6 | 4 | 1 | 0 | 0 |
| RTN2 | 3.4 | 1.7 | 1.6 | 2.4 | 1 | 0 | 2 | 0 |
| USV1 | 2.4 | 1.0 | 1.8 | 1.7 | 6 | 1 | 0 | 4 |
| RGI1 | 3.3 | 1.1 | 3.1 | 2.2 | 4 | 1 | 4 | 3 |
| YBL029C-A | 1.3 | 1.0 | 1.3 | 1.1 | 4 | 1 | 0 | 0 |
| YBR285W | 1.7 | 1.2 | 1.6 | 1.3 | 2 | 1 | 2 | 1 |
| YER053C-A | 1.3 | 1.1 | 1.3 | 1.0 | 2 | 0 | 0 | 0 |
| YFR017C | 3.1 | 1.1 | 2.6 | 1.6 | 2 | 0 | 0 | 1 |
| YJR096W | 1.4 | 1.3 | 1.7 | 1.6 | 1 | 1 | 2 | 1 |
| YNR034W-A | 3.4 | 2.5 | 3.3 | 3.1 | 5 | 1 | 0 | 0 |
| YPR145C-A | 1.3 | 1.0 | 1.6 | 1.0 | 0 | 0 | 0 | 0 |

Genes showing more than 2-fold change are listed. Genes whose deletion renders cells ethanol sensitive are in bold (see, FIG. 4A).

TABLE 3

List of genes related to ethanol tolerance in strains ETS2 and ETS3.

| Gene | Predictive functions |
|---|---|
| ALD3 | aldehyde dihydrogenase |
| USV1 | transcription |
| FMP16 | response to stress |
| RGI1 | iron deficiency |
| BTN2 | protein transduction; pH homeostasis |
| RTC3 | included in RNA metabolism and temperature resistance |
| HSP30 | heat shock protein |
| CTT1 | oxidative stress response |
| AIM17 | unknown |
| STF2 | regulation of mitochondrial ATP synthase; stabilization of Lnh inhibitors |
| GPH1 | polysaccharide metabolism |
| YFR017C | induced by DNA-damage agent, MMS |
| SOL4 | PPP pathway (6-P-gluconolactonase) |
| PHM8 | unknown |
| HSP12 | heat shock protein |
| SSA4 | protein folding and stabilization |
| SPI1 | cell wall development or component (?) |
| OM45 | mitochondria OMP45 |

The stress response and protein folding genes included several heat shock genes (HSP42, HSP31, HSP30, HSP12) that function at multiple sub-cellular locations such as the nucleus, mitochondrion, cytoplasm, cytoskeleton, membrane, and cell wall. In addition, and oxidative stress response gene (CTT1), and an endoplasmic reticulum and mitochondrial translocation gene (SSA4) were included. Several genes reported to be induced by ethanol (Ma, M., and Z. L. Liu., 2010) were PGM2 for glycolysis, GPH1 for glyconeogenesis, TSL1 for trehalose biosynthesis, and STF2 for metabolism of energy reserve. For the commonly down-regulated genes, functions included budding cell polarity and filament formation (n=1), carbon and carbohydrate metabolism (n=1), mating (fertilization) (n=1), protein targeting sorting and translocation (n=1), rRNA synthesis (n=1), unclassified proteins (n=3) (Table 4).

TABLE 4

List of genes commonly down-regulated in ethanol tolerant strains ETS2 and ETS3 in the absence of ethanol stress.

| | Fold change (Log$_2$) | | | | | | | |
|---|---|---|---|---|---|---|---|---|
| | ETS2 | | ETS3 | | Msn4p/ | | | |
| Gene | Exp1 | Exp2 | Exp1 | Exp2 | Msn2p | Yap1p | Hsf1p | Hac1p |
| Budding Cell Polarity and Filament Formation | | | | | | | | |
| RAX2 | −1.3 | −1.0 | −1.0 | −1.5 | 0 | 1 | 2 | 0 |
| C-Compound and Carbohydrate Metabolism | | | | | | | | |
| BSC1 | −2.1 | −2.1 | −1.5 | −2.2 | 3 | 1 | 1 | 0 |
| Mating (fertilization) | | | | | | | | |
| PRM7 | −1.0 | −1.0 | −1.3 | −1.2 | 0 | 0 | 0 | 2 |

TABLE 4-continued

List of genes commonly down-regulated in ethanol tolerant strains ETS2 and ETS3 in the absence of ethanol stress.

| | Fold change (Log₂) | | | | | | | |
|---|---|---|---|---|---|---|---|---|
| | ETS2 | | ETS3 | | Msn4p/ | | | |
| Gene | Exp1 | Exp2 | Exp1 | Exp2 | Msn2p | Yap1p | Hsf1p | Hac1p |
| Protein Targeting Sorting and Translocation | | | | | | | | |
| VTS1 | −1.5 | −1.1 | −1.1 | −1.1 | 2 | 0 | 2 | 0 |
| rRNA Synthesis | | | | | | | | |
| RRN7 | −1.7 | −1.3 | −4.0 | −1.2 | 2 | 0 | 2 | 2 |
| Unclassified Proteins | | | | | | | | |
| VEL1 | −2.6 | −1.0 | −1.2 | −5.1 | 0 | 0 | 2 | 0 |
| YGR035C | −1.8 | −1.1 | −1.1 | −1.7 | 0 | 0 | 2 | 1 |
| YOR387C | −2.7 | −1.0 | −1.1 | −4.5 | 0 | 0 | 2 | 1 |

Genes showing more than 2-fold change are listed. Genes whose deletion renders cells ethanol tolerant are in bold (see, FIG. 4B).

To gain further information on the transcriptional regulation of commonly up- and down-regulated genes, we examined the presence of putative binding sites for transcription factors presumed to be involved in various stress responses, such as Msn2p/Msn4p for general stress (Watanabe, et al., 2007), Hacip for protein secretion stress (Ogawa and Mori, 2004), Hsf1p for heat stress (Yamamoto, et al., 2008), and Yap1p for oxidative stress (He and Fassler, 2005). Quite intriguingly, the binding sites for these transcription factors were highly enriched in the upstream regions of commonly up-regulated genes (Table 2). Particularly, the binding sites for Msn2p/Msn4p were found in nearly all of commonly up-regulated genes. Meanwhile, the binding sites for Msn4p/Msn2p and Yap1p were found far less frequently, in contrast to similar frequencies for Hac1p and Hsf1p, in the eight commonly down-regulated genes (Table 3). The collective data suggests that Msn4p/Msn2p and Yap1p may be responsible for the regulation of genes associated with ethanol tolerance. Further studies are needed to investigate whether these transcription factors are directly or indirectly regulated by or cooperate with mutated Spt15p, which may result in the up- and regulation of a set of genes conferring enhanced ethanol tolerance.

Effect of Commonly Regulated Genes on Ethanol Tolerance

Of concern was whether the 34 commonly up-regulated and eight commonly down-regulated genes were a cause or an effect of ethanol tolerance. If the up-regulation of a gene enhanced ethanol tolerance, it would be highly likely that its deletion would render cells sensitive or resistant to ethanol. The reverse would be the case for the down-regulated genes. Deletion mutants corresponding to 30 up- and six down-regulated genes were retrieved from the BY4741 SGKO collection. Those corresponding to four up-regulated genes (YER053C-A, YNR034W-A, YPR145C-A and YBL029C-A) and two down-regulated genes (RRN7 and YOR387C) were not available, probably due to their lethality. BY4741 as control and individual deletion mutants grown to an OD$_{600}$ of 0.5 were diluted 10-fold and spotted on solid YPD medium containing several different concentrations of ethanol.

Figure 4:
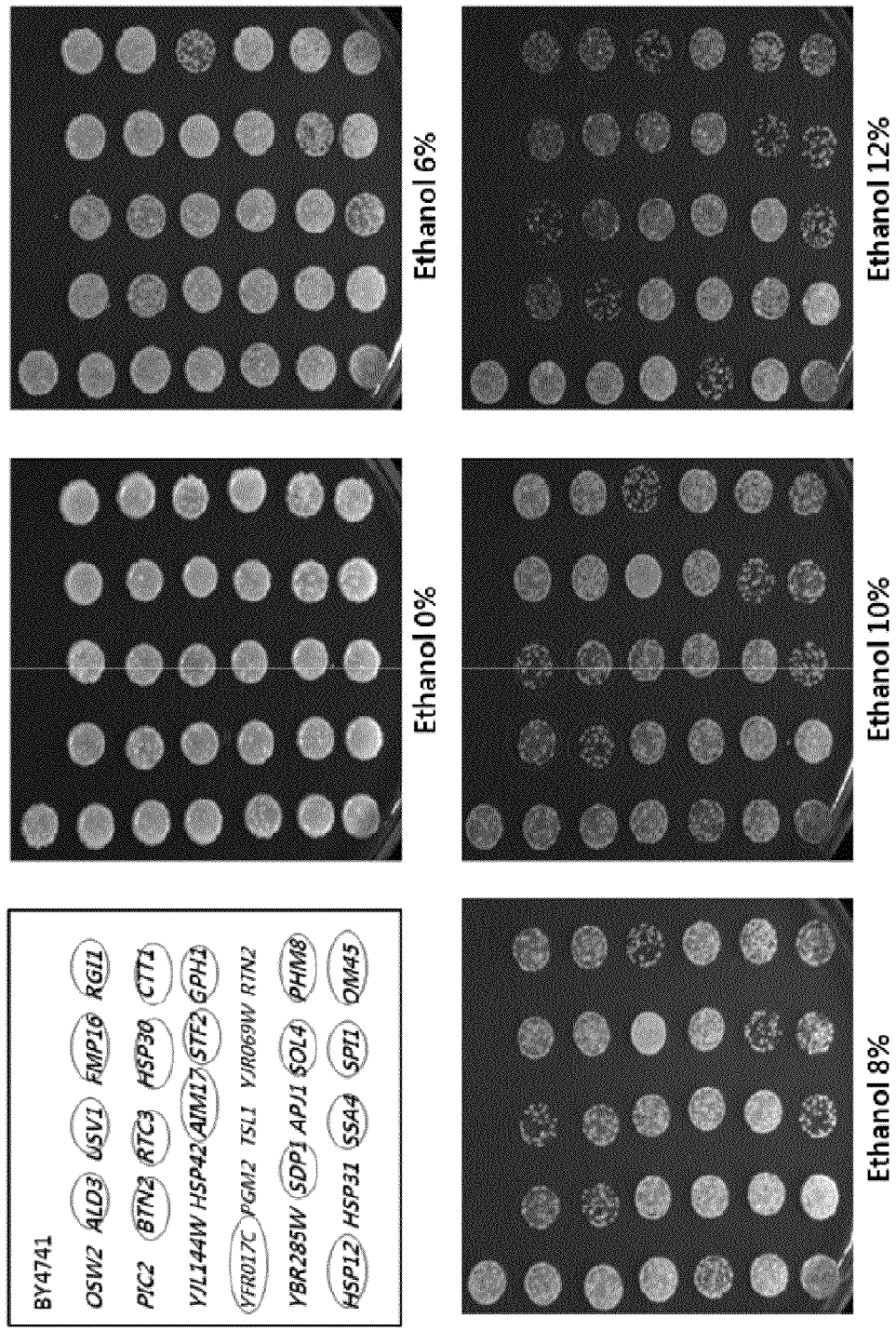
FIG. 4 is a spot assay representing ethanol sensitivity of SGKO mutants. Individual clones corresponding to 30 commonly up-regulated in ETS2 and ETS3 were picked from the BY4741 SGKO library. Spot assay was performed as in FIG. 1. The parental strain BY4741 was used as a control. Cells were cultured in liquid YPD and spotted on solid YPD containing 0%, 6%, 8%, 10%, and 12% ethanol, and incubated at 30° C. for 4-6 days.

The results for 30 deletion mutants corresponding to commonly up-regulated genes are shown in FIG. 4. Some deletion mutants were sensitive to as low as 6%, far below the concentration that exerts toxic effect to BY4741. It was natural that total number of sensitive mutants increased as the ethanol concentration increased up to 12%. Sensitivity to 6% ethanol corresponded to deletions in GPH1, SOL4, and SSA4. An additional seven mutants (ALD3, BTN2, SPI1, OM45, RTC3, USV1, and YFR017C) were sensitive to 8% ethanol. The HSP12 deletion mutant was sensitive to 10% ethanol. Finally, deletions in HSP30, CTT1, SDP1, STF2, AIM17, FMP16, RGI1, and PHM8 rendered mutants sensitive to 12% ethanol. Thus, deletion of 19 out of 30 genes commonly up-regulated in ETS2 and ETS3 conferred ethanol sensitivity. The degree of contribution to ethanol sensitivity was greatest for GPH1, SOL4, SSA4; next for ALD3, BTN2, SPI1, OM45, RTC3, USV1, YFR017C; followed by HSP12; and was least for HSP30, CTT1, SDP1, STF2, AIM17, FMP16, RGI1, and PHM8.

Meanwhile, none of six deletion mutants corresponding to commonly down-regulated genes displayed enhanced growth (data mot shown), contrary to our expectation, based on the hypothesis mentioned above, that deletion mutants corresponding to the down-regulated genes would display the same or higher degree of ethanol tolerance as that of control. The reason for this remains obscure.

The Effect of Mutated SPT15s on Ethanol Production

Besides understanding the mechanisms underlying tolerance to ethanol, the aim of constructing ethanol tolerant strains is to improve ethanol productivity and/or final yield. Compared to control strains, strains with enhanced ethanol tolerance are presumed to better cope with the toxic effect of ethanol (Ding, et al., 2009). Once phenotypically characterized, the effect of enhanced ethanol tolerance is usually determined by measuring the highest ethanol titer from batch cultures in a complex rich medium containing up to 30% glucose (Hong, et al., 2009; Hou, 2009; Hou, et al., 2009; Teixeira, et al., 2009). In these studies, however, the yields were not dramatically improved, and were increased by only slightly more than 10% compared to the control strains. The reason for this may be that most parental laboratory strains used are basically capable of producing maximum levels of ethanol, such that it is difficult to observe the effect of enhanced ethanol tolerance. Accordingly, it may be possible to observe such an effect only at ethanol concentrations that far exceed the basic ethanol-producing capability of parental strains. In the present study, the YPD30E6 media, YPD30 to which 6% (v/v) ethanol was initially added, were used for fermentation.

When fermentation was performed as described in Materials and Methods, the cell densities of the control (iL3262)

and two ethanol tolerant integrants (iETS2 and iETS3) reached maximum at 84 h and then declined (FIG. 5A). Features in this profile were that iL3262 needed a longer lag period (24 h) probably required for adaptation to initially added ethanol and that the saturation plateau was not observed. During next 24 h, the growth rate of iETS3 was slighter higher than those of iL3262 and iETS2 which grew at the same rate. After 48 h time point, three strains grew at a similar rate in general until 84 h time point with exception of the 60 h time point for iETS3. So, the relatively short length of lag period may represent a characteristic of ethanol tolerant strains.

The fermentation capacity of iL3262, iETS2, and iETS3 was determined by measuring ethanol titer from the same YPD30E6 cultures. The initial 6% (v/v) ethanol corresponded to 47.5 g/L on HPLC. As shown in FIG. 5B, the highest ethanol titers produced by iETS2 and iETS3 during 120 h-long fermentation were 95.0 g/L and 93.0 g/L respectively, whereas that of the control was 74.0 g/L. Interestingly, a lag period in ethanol production was not observed in the control strain in contrast to the cell growth, the reason for this being unclear. Subtracting the initially added ethanol (47.5 g/L) from the final titer yields the net amount of ethanol produced during fermentation: 26.5 g/L for the control, 47.5 g/L for iETS2, and 45.5 g/L for iETS3. Although these yields were lower than expected, iETS2 and iETS3 exhibited 80% higher fermentation capacity than the control under the current experimental condition.

Figure 7:
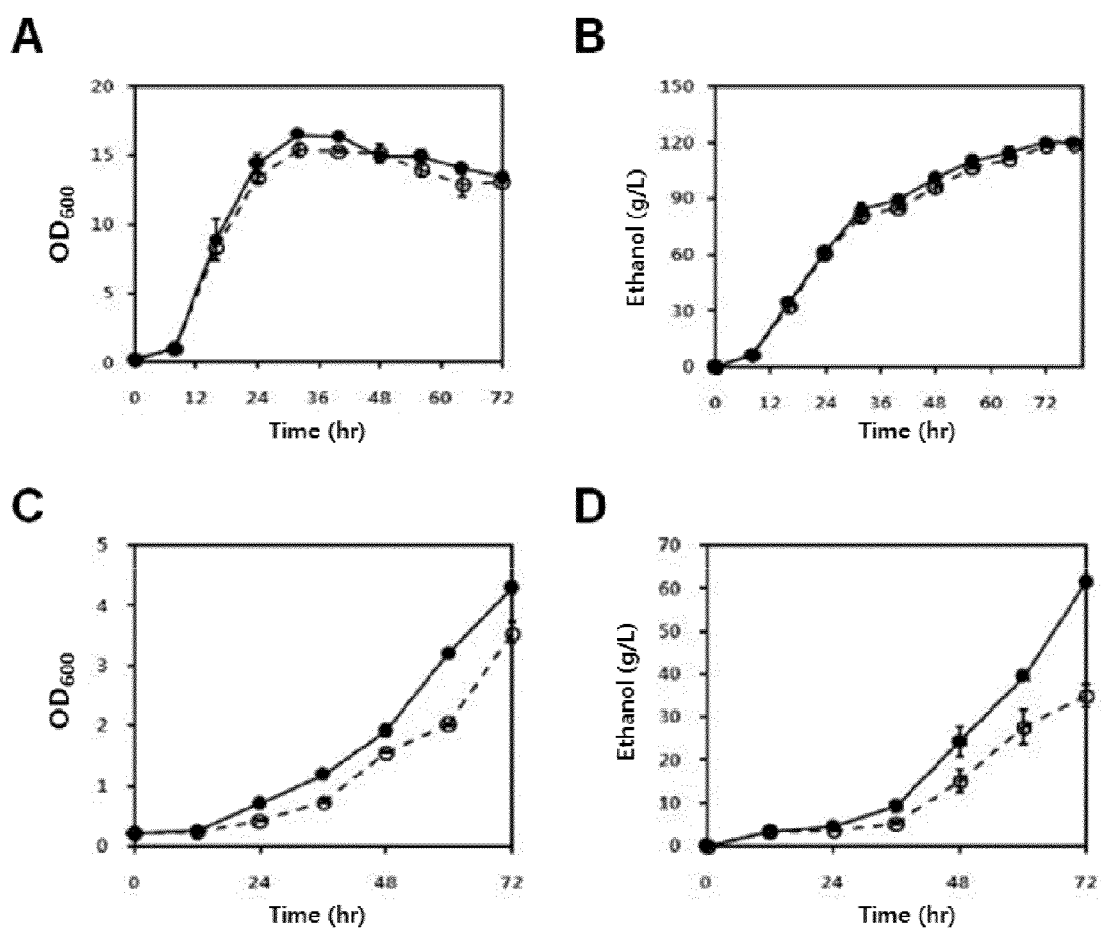
FIG. 7 is a result measuring a fermentation capacity of osmo-tolerant strain, ETS3. Each cell growth and ethanol production of ETS3(●) and control strain, Sc L3262 (○) was measured by culturing in YPD media containing high glucose concentration (50%). Cells were cultured at 30° C. with shaking at 120 rpm. After samples were taken as indicated time, cell growth (A, C) and ethanol production (B, D) was measured. Representative experiment was shown.

The Effect of Mutated SPT15s on Ethanol Production and Growth Rate Under the Condition with High Glucose or Sucrose Concentration ETS3 strain of this invention exhibits a resistance against high osmotic pressure induced by high glucose or sucrose concentration. As shown in FIG. 6, the growth rate under diverse glucose and sucrose concentrations (for example, 20%, 30% or 40%) in ETS3 strain of this invention showed much higher than that in control strain. Interestingly, growth rate of ETS3 under 40% glucose concentration was highest than that of control strain (Sc L3262). In addition, according to a fermentation experiment of FIG. 7 carried out in 50% glucose-containing YPD, it could be appreciated that osmo-tolerant ETS3 strain of the present invention is closely related to ethanol fermentation. In detail, ETS3 strain (63 g/L) of the present invention showed ethanol production enhanced by 70.3% at 72 h compared with control strain (Sc 3262; 37 g/L). Accordingly, it could be appreciated that fermentation capacity of ETS3 strain under the experimental conditions used in the present invention is around 70% higher than that of control strain.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Alper, H., J. Moxley, E. Nevoigt, G. R. Fink, and G. Stephanopoulos. Engineering yeast transcription machinery for improved ethanol tolerance and production. Science, 314: 1565-1568 (2006).

Auesukaree, C., et al., Genome-wide identification of genes involved in tolerance to various environmental stresses in Saccharomyces cerevisiae. J Appl Genet, 50(3): 301-310 (2009).

Baerends, R. J., J. L. Qiu, S. Rasmussen, H. B. Nielsen, and A. Brandt. Impaired uptake and/or utilization of leucine by Saccharomyces cerevisiae is suppressed by the SPT15-300 allele of the TATA-binding protein gene. Appl Environ Microbiol, 75: 6055-61 (2009).

Casey, G. P., et al., ETHANOL TOLERANCE IN YEASTS. Critical Reviews in Microbiology, Vol 13(3): 219-280 (1986).

Cang, Y., D. T. Auble, and G. Prelich. A new regulatory domain on the TATA-binding protein. EMBO J, 18: 6662-71 (1999).

Chasman et al., Crystal structure of yeast TATA-binding protein and model for interaction with DNA. Proc Natl Acad Sci USA, 90(17): 8174-8178 (1993).

Ding, J., X. Huang, L. Zhang, N. Zhao, D. Yang, and K. Zhang. Tolerance and stress response to ethanol in the yeast Saccharomyces cerevisiae. Appl Microbiol Biotechnol, 85: 253-63 (2009).

Eisenmann, D. M., C. Dollard, and F. Winston. SPT15, the gene encoding the yeast TATA binding factor TFIID, is required for normal transcription initiation in vivo. Cell, 58: 1183-91 (1989).

Fujita, K., et al., The genome-wide screening of yeast deletion mutants to identify the genes required for tolerance to ethanol and other alcohols. FEMS Yeast Research, Vol 6(5): 744-750 (2006).

Gibson, B. R., S. J. Lawrence, J. P. Leclaire, C. D. Powell, and K. A. Smart. Yeast responses to stresses associated with industrial brewery handling. FEMS Microbiol Rev, 31: 535-69 (2007).

He, X. J., and J. S. Fassler. Identification of novel Yap1p and Skn7p binding sites involved in the oxidative stress response of Saccharomyces cerevisiae. Mol Microbiol, 58: 1454-67 (2005).

Hirasawa, T., et al., Identification of target genes conferring ethanol stress tolerance to Saccharomyces cerevisiae based on DNA microarray data analysis. Journal of Biotechnology, 131: 34-44 (2007).

Hong, M. E., K. S. Lee, B. J. Yu, Y. J. Sung, S. M. Park, H. M. Koo, D. H. Kweon, J. C. Park, and Y. S. Jin. Identification of gene targets eliciting improved alcohol tolerance in Saccharomyces cerevisiae through inverse metabolic engineering. J Biotechnol, 149: 52-9 (2009).

Hou, L. Novel methods of genome shuffling in Saccharomyces cerevisiae. Biotechnol Lett, 31: 671-7 (2009).

Hou, L., X. Cao, C. Wang, and M. Lu. Effect of overexpression of transcription factors on the fermentation properties of Saccharomyces cerevisiae industrial strains. Lett Appl Microbiol, 49: 14-9 (2009).

Jeffries, T., and P. Lindblad. We march backwards into the future. Curr Opin Biotechnol, 20: 255-6 (2009).

Kajiwara, S., et al., Overexpression of the OLE1 gene enhances ethanol fermentation by Saccharomyces cerevisiae. Appl Microbiol Biotechnol, 53: 568-574 (2000).

KIM, J., et al., Disruption of the Yeast ATH1 Gene Confers Better Survival after Dehydration, Freezing, and Ethanol Shock: Potential Commercial Applications. APPLIED AND ENVIRONMENTAL MICROBIOLOGY, Vol 62(5): 1563-1569 (1996).

Inoue, T., et al., Cloning and Characterization of a Gene Complementing the Mutation of an Ethanol-sensitive Mutant of Sake Yeast. Biosci. Biotechnol. Biochem., 64(2): 229-236 (2000).

Ma, M., and Z. L. Liu. Mechanisms of ethanol tolerance in Saccharomyces cerevisiae. Appl. Microbiol. Biotechnol., 87: 829-845 (2010).

Merja Suutari and Siino Laakso, Microbial Fatty Acids and Thermal Adaptation. Critical Reviews in Microbiology, 20(4): 255-328 (1994).
Oh K. S., O. K., Y. W. Oh, M. J. Sohn, S. Jung., Y. K. Kim., M.-G. Kim, S. K. Rhee, G. Gellissen, and Kang H. A. Fabrication of a partial genome microarray of the methylotrophic yeast *Hansenula polymorpha*: optimization and evaluation for transcript profiling. J. Microbiol. Biotechnol., 14: 1239-48 (2004).
Ogawa, N., and K. Mori. Autoregulation of the HAC1 gene is required for sustained activation of the yeast unfolded protein response. Genes Cells, 9: 95-104 (2004).
Park, J. N., M. J. Sohn, D. B. Oh, O. Kwon, S. K. Rhee, C. G. Hur, S. Y. Lee, G. Gellissen, and H. A. Kang. 2007. Identification of the cadmium-inducible *Hansenula polymorpha* SEO1 gene promoter by transcriptome analysis and its application to whole-cell heavy-metal detection systems. Appl Environ Microbiol, 73: 5990-6000 (2007).
Pieler, R., F. Sanchez-Cabo, H. Hackl, G. G. Thallinger, and Z. Trajanoski. ArrayNorm: comprehensive normalization and analysis of microarray data. Bioinformatics, 20: 1971-3 (2004).
Ragauskas, A. J., C. K. Williams, B. H. Davison, G. Britovsek, J. Cairney, C. A. Eckert, W. J. Frederick, Jr., J. P. Hallett, D. J. Leak, C. L. Liotta, J. R. Mielenz, R. Murphy, R. Templer, and T. Tschaplinski. The path forward for biofuels and biomaterials. Science, 311: 484-9 (2006).
Rubin, E. M. Genomics of cellulosic biofuels. Nature, 454: 841-5 (2008).
Sambrook, J. a. D. W. R. Molecular cloning: a laboratory manual, 3rd ed. ed. Cold Spring Harbor Laboratory Press, N.Y. (2001).
Scharlemann, J. P., and W. F. Laurance. Environmental science. How green are biofuels? Science, 319: 43-4 (2008).
Takagi, H., et al., Effect of L-Proline on Sake Brewing and Ethanol Stress in *Saccharomyces cerevisiae*. Applied and Environmental Microbiology, Vol 71(12): 8656-8662 (2005).
Takahashi, T., et al., Identification of genes required for growth under ethanol stress using transposon mutagenesis in *Saccharomyces cerevisiae*. Molecular Genetics and Genomics, Vol 265(6): 1112-1119 (2001).
Teixeira, M C., et al., Genome-Wide Identification of *Saccharomyces cerevisiae* Genes Required for Maximal Tolerance to Ethanol. APPLIED AND ENVIRONMENTAL MICROBIOLOGY, Vol 75(18): 5761-5772 (2009).
Watanabe, M., K. Tamura, J. P. Magbanua, K. Takano, K. Kitamoto, H. Kitagaki, T. Akao, and H. Shimoi. Elevated expression of genes under the control of stress response element (STRE) and Msn2p in an ethanol-tolerance sake yeast Kyokai no. 11. J Biosci Bioeng, 104: 163-70 (2007).
Xu, Q., A. Singh, and M. E. Himmel. Perspectives and new directions for the production of bioethanol using consolidated bioprocessing of lignocellulose. Curr Opin Biotechnol, 20: 364-71 (2009).
Yamamoto, N., Y. Maeda, A. Ikeda, and H. Sakurai. Regulation of thermotolerance by stress-induced transcription factors in *Saccharomyces cerevisiae*. Eukaryot Cell, 7: 783-90 (2008)
Yoshikawa, K., et al., Genome-Wide Analysis of the Effects of Location and Number of Stress Response Elements on Gene Expression in *Saccharomyces cerevisiae*. JOURNAL OF BIOSCIENCE AND BIOENGINEERING, vol 106(5): 507-510 (2008).
Yoshikawa, K., T. Tanaka, C. Furusawa, K. Nagahisa, T. Hirasawa, and H. Shimizu. Comprehensive phenotypic analysis for identification of genes affecting growth under ethanol stress in *Saccharomyces cerevisiae*. FEMS Yeast Res, 9: 32-44 (2009).
You, K. M., et al., Ethanol Tolerance in the Yeast *Saccharomyces cerevisiae* Is Dependent on Cellular Oleic Acid Content. APPLIED AND ENVIRONMENTAL MICROBIOLOGY, Vol 69(3): 1499-1503 (2003).

What is claimed is:

1. An ethanol-tolerant yeast strain transformed with a mutated SPT15 gene, wherein the mutated SPT15 gene is selected from the group consisting of a nucleotide sequence encoding an amino acid sequence consisting of mutations at positions L76 and L175 in the amino acid sequence of wild-type *Saccharomyces cerevisiae* SPT15 gene; a nucleotide sequence encoding an amino acid sequence consisting of mutations at positions S42, C78, S163, and I212 in the amino acid sequence of wild-type *Saccharomyces cerevisiae* SPT15 gene; a nucleotide sequence encoding an amino acid sequence consisting of mutations at positions F10 and M197 in the amino acid sequence of wild-type *Saccharomyces cerevisiae* SPT15 gene; a nucleotide sequence encoding an amino acid sequence consisting of mutations at positions W26 and G192 in the amino acid sequence of wild-type *Saccharomyces cerevisiae* SPT15 gene; and a nucleotide sequence encoding an amino acid sequence consisting of mutations at positions K15, W26 and G192 in the amino acid sequence of wild-type *Saccharomyces cerevisiae* SPT15 gene.

2. The yeast strain according to claim 1, wherein the mutated SPT15 gene is selected from the group consisting of: a nucleotide sequence encoding an amino acid sequence in which an amino acid sequence at position L76 and L175 is mutated to the amino acid sequence at position L76V and L175S in the amino acid sequence of wild-type SPT15 gene (SEQ ID NO: 7); a nucleotide sequence encoding an amino acid sequence in which an amino acid sequence at position S42, C78, S163 and I212 is mutated to the amino acid sequence at position S42N, C78R, S163P and I212N in the amino acid sequence of wild-type SPT15 gene (SEQ ID NO: 8); a nucleotide sequence encoding an amino acid sequence which an amino acid sequence at position F10 and M197 is mutated to the amino acid sequence at position F10S and M197K in the amino acid sequence of wild-type SPT15 gene (SEQ ID NO: 9); and a nucleotide sequence encoding an amino acid sequence which an amino acid sequence at position K15, W26 and G192 is mutated to the amino acid sequence at position K15T, W26C and G192D in the amino acid sequence of wild-type SPT15 gene (SEQ ID NO: 10).

3. The yeast strain according to claim 1, wherein the yeast strain may grow under a culture condition with a concentration of 5-15% ethanol.

4. The yeast strain according to claim 3, wherein the yeast strain may grow under a culture condition with a concentration of 12.5-15% ethanol.

5. An osmo-tolerant yeast strain transformed with a mutated SPT15 gene, wherein the mutated SPT15 gene consists of a nucleotide sequence encoding an amino acid sequence consisting of mutations at positions S42, C78, S163, and I212 in the amino acid sequence of wild-type *Saccharomyces cerevisiae* SPT15 gene.

6. The yeast strain according to claim 5, wherein the mutated SPT15 gene consists of a nucleotide sequence encoding an amino acid sequence which the amino acid sequence at positions position S42, C78, S163 and I212 is mutated to the amino acid sequence at position S42N, C78R, S163P, and I212N in the amino acid sequence of wild-type SPT15 gene (SEQ ID NO: 8).

7. The yeast strain according to claim 5, wherein the yeast strain may grow under a culture condition with a concentration of 30-40% glucose or sucrose.

8. The yeast strain according to claim 5, wherein the yeast strain further has resistance to a concentration of 5-15% ethanol.

9. A method for preparing an ethanol-tolerant yeast strain, comprising the step of transforming a yeast cell with a mutated SPT15 gene, wherein the mutated SPT15 gene is selected from the group consisting of: a nucleotide sequence encoding an amino acid sequence consisting of mutations at positions L76 and L175 in the amino acid sequence of wild-type *Saccharomyces cerevisiae* SPT15 gene; a nucleotide sequence encoding an amino acid sequence consisting of mutations at positions S42, C78, S163, and I212 in the amino acid sequence of wild-type *Saccharomyces cerevisiae* SPT15 gene; a nucleotide sequence encoding an amino acid sequence consisting of mutations at positions F10 and M197 in the amino acid sequence of wild-type *Saccharomyces cerevisiae* SPT15 gene; a nucleotide sequence encoding an amino acid sequence consisting of mutations at positions W26 and G192 in the amino acid sequence of wild-type *Saccharomyces cerevisiae* SPT15 gene; and a nucleotide sequence encoding an amino acid sequence consisting of mutations at positions K15, W26 and G192 in the amino acid sequence of wild-type *Saccharomyces cerevisiae* SPT15 gene.

10. The method according to claim 9, wherein the mutated SPT15 gene is selected from the group consisting of: a nucleotide sequence encoding an amino acid sequence in which an amino acid sequence at position L76 and L175 is mutated to the amino acid sequence at position L76V and L175S in the amino acid sequence of wild-type SPT15 gene (SEQ ID NO: 7); a nucleotide sequence encoding an amino acid sequence in which an amino acid sequence at position S42, C78, S163 and I212 is mutated to the amino acid sequence at position S42N, C78R, S163P and I212N in the amino acid sequence of wild-type SPT15 gene (SEQ ID NO: 8); a nucleotide sequence encoding an amino acid sequence in which an amino acid sequence at position F10 and M197 is mutated to the amino acid sequence at position F10S and M197K in the amino acid sequence of wild-type SPT15 gene (SEQ ID NO: 9); and a nucleotide sequence encoding an amino acid sequence in which an amino acid sequence at position K15, W26 and G192 is mutated to the amino acid sequence at position K15T, W26C and G192D in the amino acid sequence of wild-type SPT15 gene (SEQ ID NO: 10).

* * * * *